(12) United States Patent
Yamada et al.

(10) Patent No.: US 11,819,191 B2
(45) Date of Patent: Nov. 21, 2023

(54) ENDOSCOPE CONNECTOR DEVICE

(71) Applicant: FUJIFILM Corporation, Tokyo (JP)

(72) Inventors: Hideyuki Yamada, Kanagawa (JP); Toshiharu Kuwae, Kanagawa (JP); Nobuyuki Torisawa, Kanagawa (JP); Takumi Dejima, Waltham, MA (US)

(73) Assignee: FUJIFILM Corporation, Tokyo (JP)

( * ) Notice: Subject to any disclaimer, the term of this patent is extended or adjusted under 35 U.S.C. 154(b) by 547 days.

(21) Appl. No.: 16/802,514

(22) Filed: Feb. 26, 2020

(65) Prior Publication Data

US 2020/0187759 A1 Jun. 18, 2020

Related U.S. Application Data

(63) Continuation of application No. PCT/JP2017/039124, filed on Oct. 30, 2017.

(60) Provisional application No. 62/552,399, filed on Aug. 31, 2017.

(51) Int. Cl.
*A61B 1/00* (2006.01)
*A61L 29/02* (2006.01)
*A61B 1/07* (2006.01)

(52) U.S. Cl.
CPC ...... *A61B 1/00128* (2013.01); *A61B 1/00124* (2013.01); *A61B 1/00126* (2013.01); *A61L 29/02* (2013.01); *A61B 1/07* (2013.01)

(58) Field of Classification Search
CPC ............ A61B 1/00112; A61B 1/00124; A61B 1/00126; A61B 1/00128; A61B 29/02; H02G 15/013; H02G 15/117
See application file for complete search history.

(56) References Cited

U.S. PATENT DOCUMENTS 3,158,379 A * 11/1964 Nava .................. H01R 13/5205
174/93
5,216,203 A * 6/1993 Gower .................. H02G 3/088
174/152 G
(Continued)

FOREIGN PATENT DOCUMENTS

CN 101052341 10/2007
CN 101301189 11/2008
(Continued)

OTHER PUBLICATIONS

"Office Action of Japan Counterpart Application", dated Mar. 1, 2022, with English translation thereof, p. 1-p. 8.
(Continued)

*Primary Examiner* — John P Leubecker
*Assistant Examiner* — Li-Ting Song
(74) *Attorney, Agent, or Firm* — JCIPRNET

(57) ABSTRACT

The connector device includes a metal internal member, a metal light guide rod and metal fixing bases and, which are connected to the internal member, a resin sheathing member that accommodates the internal member and includes leading-out holes, which lead the light guide rod and the fixing base to the outside, and fluoro rubber O-rings, which are provided on the light guide rod and the fixing bases, the O-rings being respectively placed in gaps between the light guide rod and the fixing bases and the leading-out holes and sealing the inside of the sheathing member.

10 Claims, 50 Drawing Sheets

(56) References Cited

U.S. PATENT DOCUMENTS

| | | | | |
|---|---|---|---|---|
| 5,574,259 | A * | 11/1996 | Meltsch | H02G 15/013 |
| | | | | 174/91 |
| 5,850,496 | A | 12/1998 | Bellahsene et al. | |
| 6,088,876 | A * | 7/2000 | Daoud | F16L 5/10 |
| | | | | 16/2.2 |
| 6,747,429 | B2 * | 6/2004 | Igarashi | B41J 13/0009 |
| | | | | 271/226 |
| 2002/0066325 | A1 * | 6/2002 | Roither | H02K 7/1166 |
| | | | | 74/425 |
| 2002/0099265 | A1 * | 7/2002 | Wako | A61B 1/07 |
| | | | | 600/132 |
| 2003/0000726 | A1 * | 1/2003 | Miyakoshi | H02G 3/088 |
| | | | | 174/650 |
| 2005/0131392 | A1 * | 6/2005 | Chu | A61F 2/0045 |
| | | | | 606/1 |
| 2008/0281157 | A1 | 11/2008 | Miyagi et al. | |
| 2008/0281158 | A1 | 11/2008 | Miyagi et al. | |
| 2012/0202385 | A1 | 8/2012 | Miyagi et al. | |
| 2013/0146355 | A1 * | 6/2013 | Strasser | H02G 3/0406 |
| | | | | 174/72 A |
| 2015/0378144 | A1 * | 12/2015 | Handte | G02B 23/2484 |
| | | | | 250/208.1 |
| 2016/0287060 | A1 * | 10/2016 | Usuda | A61B 1/051 |
| 2017/0111010 | A1 * | 4/2017 | Kondo | H03B 28/00 |
| 2023/0135724 | A1 * | 5/2023 | Tabe | A61B 1/00016 |
| | | | | 600/173 |

FOREIGN PATENT DOCUMENTS

| | | |
|---|---|---|
| CN | 101308975 | 11/2008 |
| EP | 0726059 | 8/1996 |
| JP | S58195819 | 11/1983 |
| JP | H07184857 | 7/1995 |
| JP | H08211307 | 8/1996 |
| JP | H0910166 | 1/1997 |
| JP | H0966024 | 3/1997 |
| JP | H09173286 | 7/1997 |
| JP | H09253027 | 9/1997 |
| JP | 2002028130 | 1/2002 |
| JP | 2002209846 | 7/2002 |
| JP | 2002214539 | 7/2002 |
| JP | 2007135956 | 6/2007 |
| JP | 2009233186 | 10/2009 |
| WO | 0044276 | 8/2000 |
| WO | 2011052408 | 5/2011 |

OTHER PUBLICATIONS

"Search Report of Europe Counterpart Application", dated Aug. 11, 2020, pp. 1-7.

Office Action of China Counterpart Application, with English translation thereof, dated Nov. 23, 2021, pp. 1-19.

Office Action of Japan Counterpart Application, with English translation thereof, dated Feb. 1, 2021, pp. 1-8.

"International Search Report (Form PCT/ISA/210) of PCT/JP2017/039124," dated Dec. 19, 2017, with English translation thereof, pp. 1-6.

"Written Opinion of the International Searching Authority (Form PCT/ISA/237) of PCT/ JP2017/039124," dated Dec. 19, 2017, with English translation thereof, pp. 1-13.

* cited by examiner

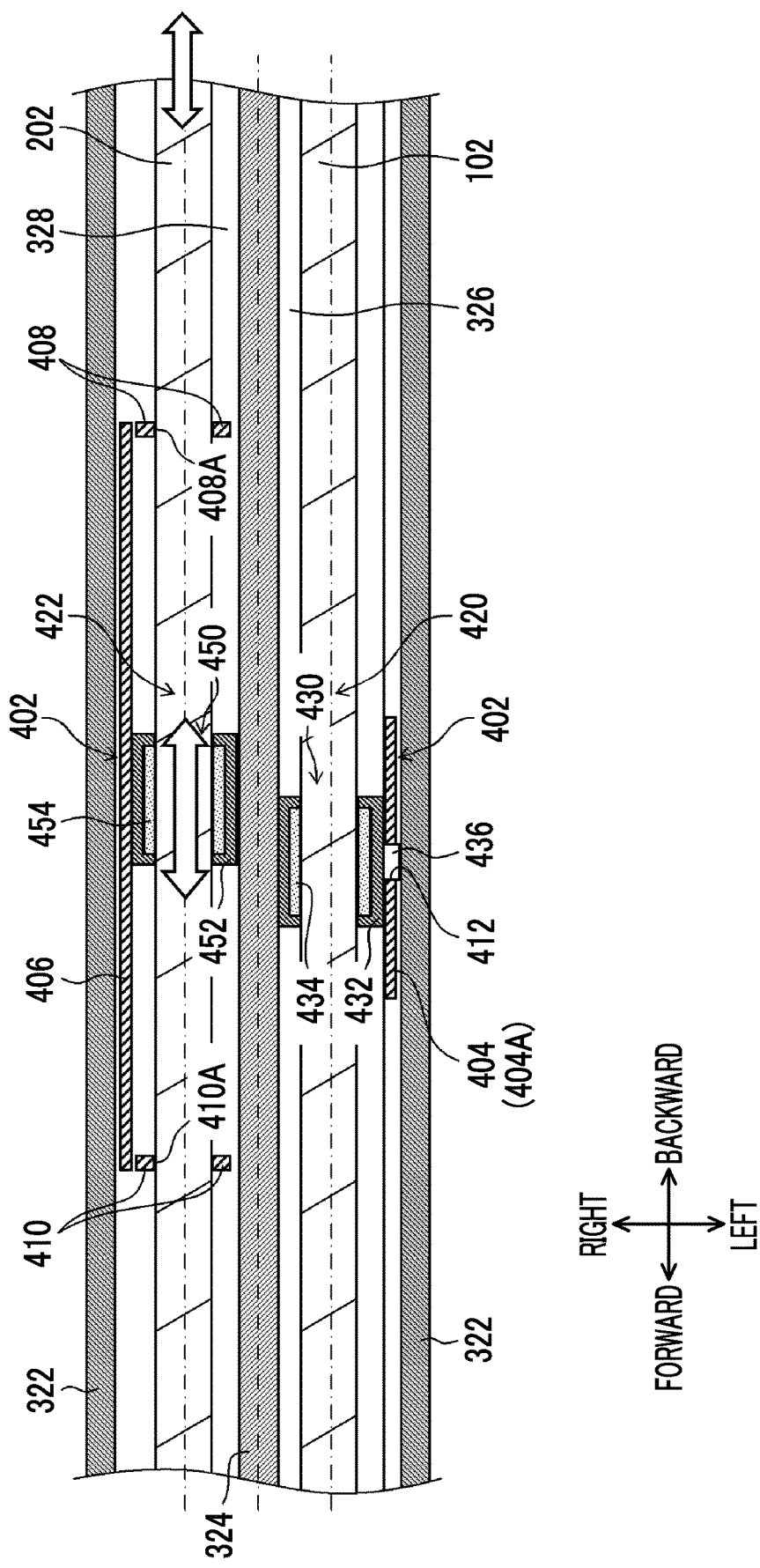

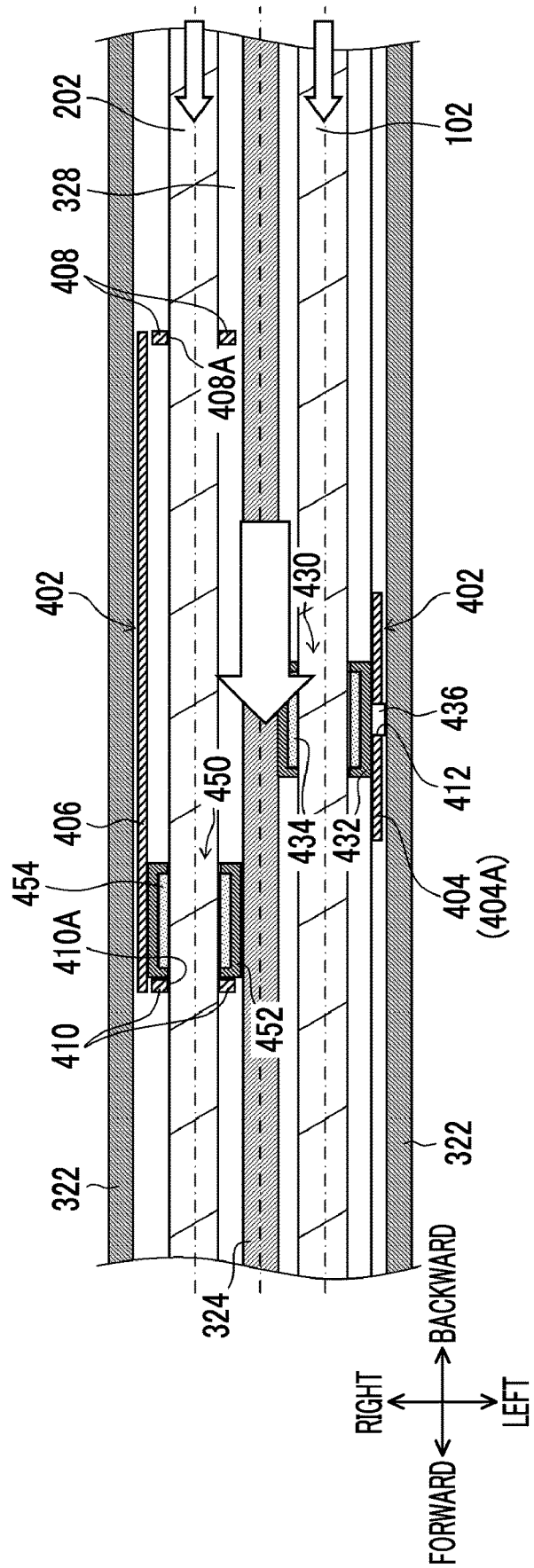

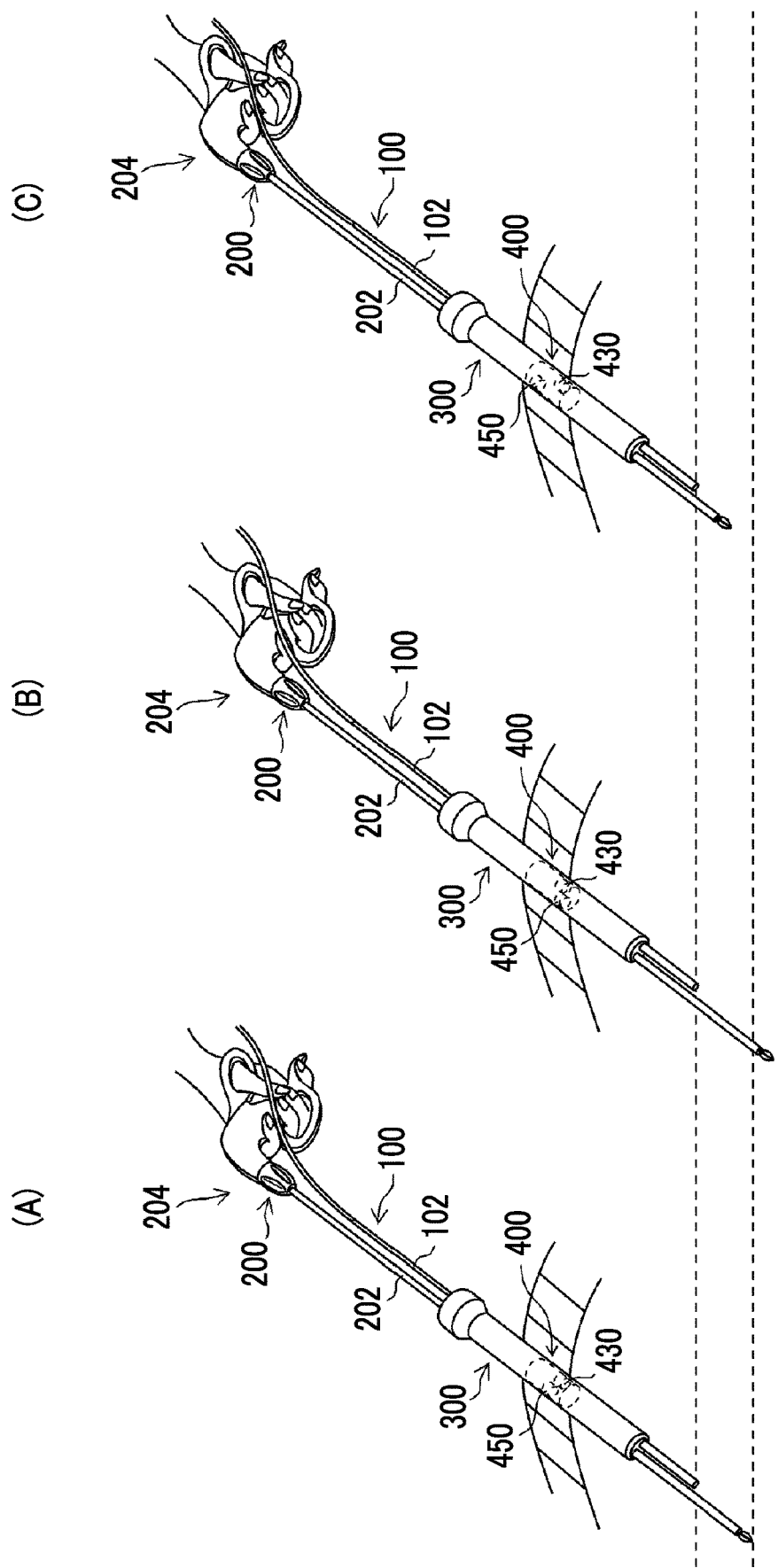

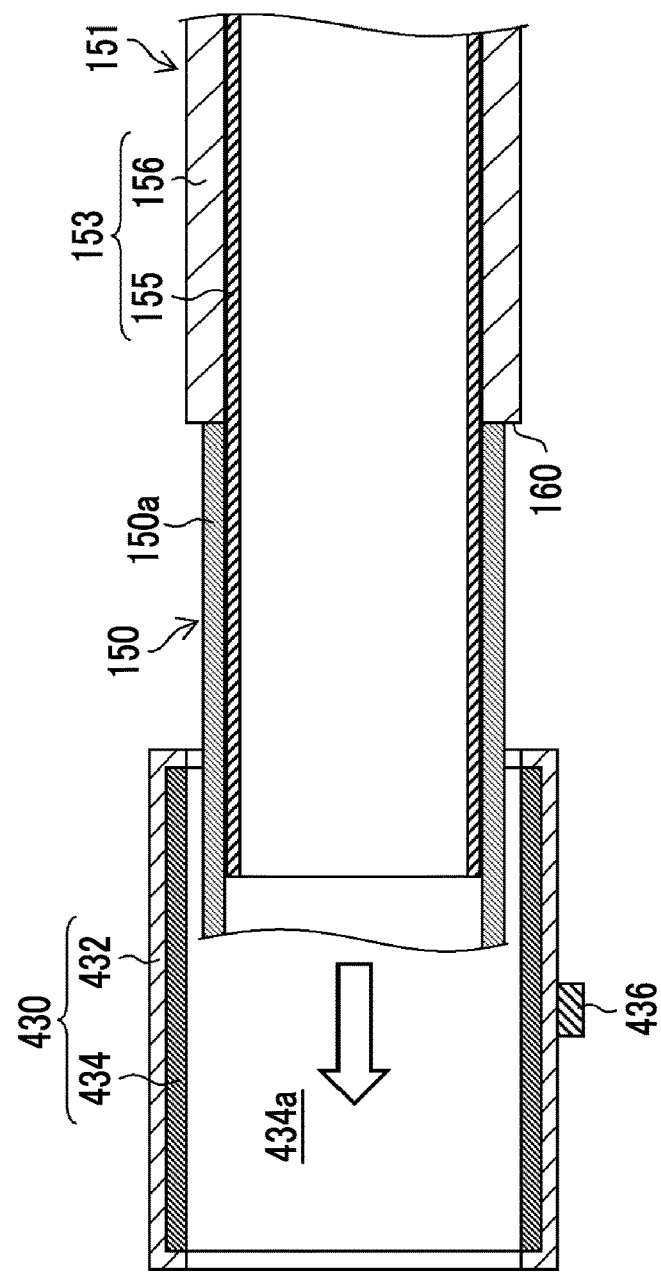

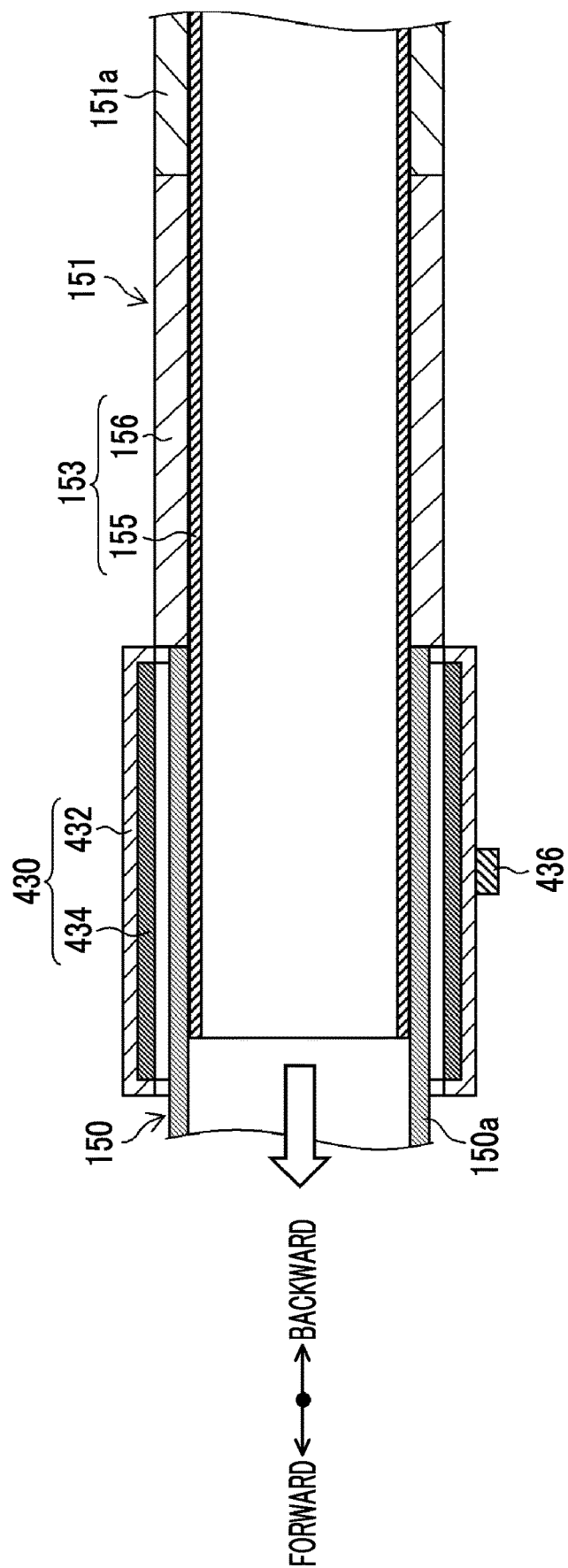

FIG. 43
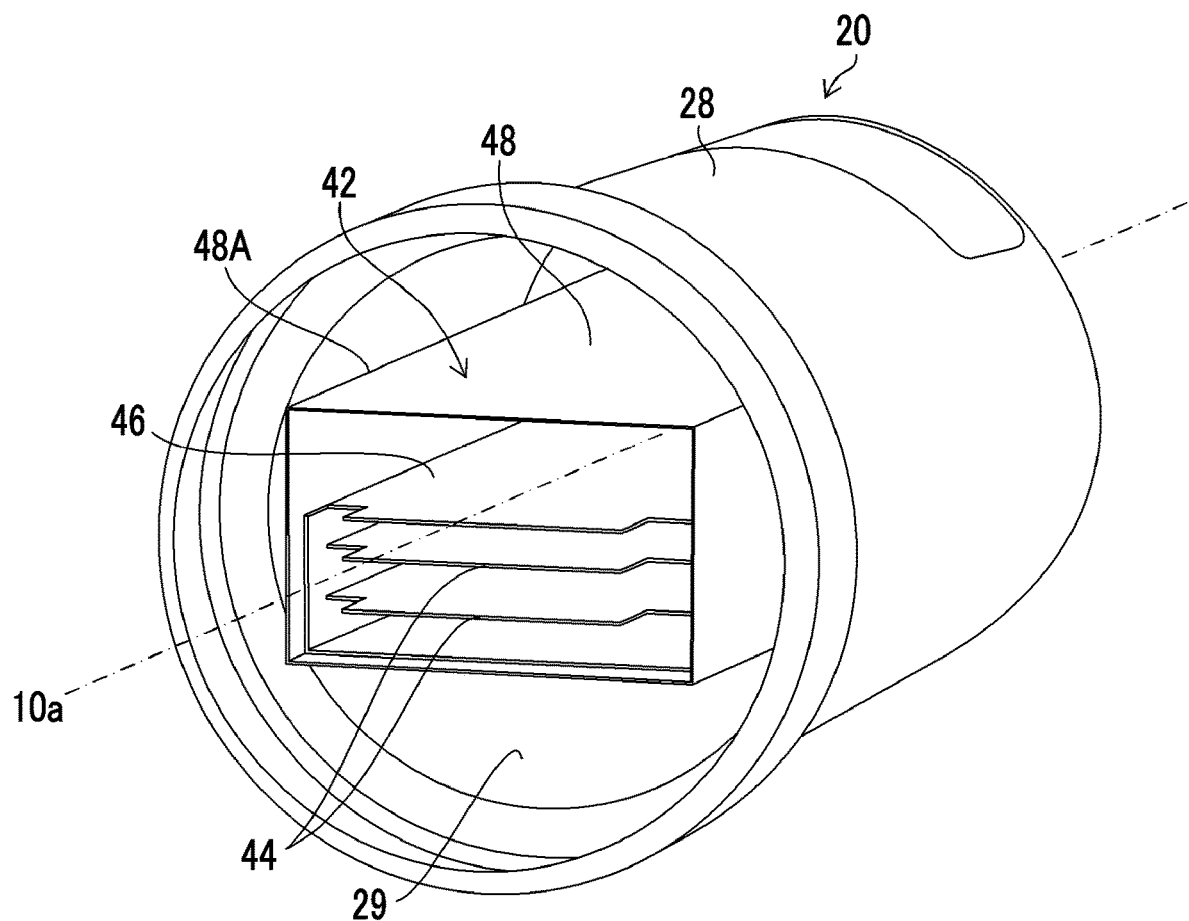
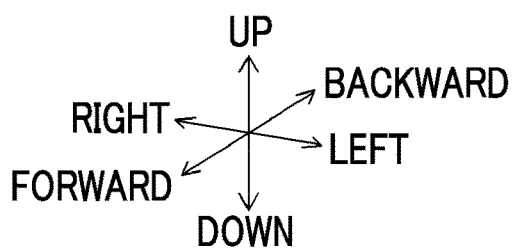

ENDOSCOPE CONNECTOR DEVICE

CROSS-REFERENCE TO RELATED APPLICATIONS

The present application is a Continuation of PCT International Application No. PCT/JP2017/039124 filed on Oct. 30, 2017 claiming priority under 35 U.S.C § 119(a) to U.S. Provisional Application No. 62/552,399 filed on Aug. 31, 2017. Each of the above applications is hereby expressly incorporated by reference, in its entirety, into the present application.

BACKGROUND OF THE INVENTION

1. Field of the Invention

The present invention relates to an endoscope connector device, and particularly to an endoscope connector device that comprises a light guide rod which is provided at a distal end part of a universal cable of an endoscope and is connected to a light source device.

2. Description of the Related Art

An endoscope called as an electronic endoscope, out of various endoscopes, radiates an observed part by a light guide transmitting light radiated from a light source device, and picks up an image of the observed part with a solid image pickup element. Then, a processor performs image processing on an electrical signal output from the solid image pickup element, and a monitor TV displays an observation image. In such an electronic endoscope, a universal cable extends from a hand operation part of the electronic endoscope, and a connector device is provided at a distal end part of the universal cable. A light guide rod connected to the light source device and a video cable connected to a processor device extend in the connector device. An electrical connector connected to the processor device is provided at a distal end part of the video cable.

An endoscope connector device disclosed in JP1997-066024A (JP-H9-066024A) has a case formed by a resin case body and a resin base part. A body frame is disposed in the case body, and the body frame is fixed to the base part by a screw and a nut. In addition, a light guide end is disposed to protrude from the base part. In addition, an attaching ring for disposing two cables is attached to the body frame, and two attaching holes for allowing the two cables to pass therethrough and fixing the case body to the body frame are formed in the case body. The case body is fixed to the body frame by screwing a fixing ring with the attaching ring of the body frame.

In addition, an endoscope power supply connector disclosed in JP2007-135956A has a casing. The casing comprises a first fixing part case to which a distal end part of a universal cord is connected and a second fixing part case in which an electrical cord is pulled out. The second fixing part case is screwed and inserted in the first fixing part case. In addition, the casing is provided with a connector body, and a light guide rod projects on the connector body. In addition, a relay substrate coupled to the second fixing part case is arranged in a space part between the second fixing part case and the connector body, and a signal cable inserted in the universal cord is connected to the relay substrate. In addition, wiring is pulled out from the relay substrate, and the wiring is inserted in the electrical cord.

SUMMARY OF THE INVENTION

In a case where even a small amount of moisture such as mist infiltrates into a sheathing member, condensation occurs in an internal member accommodated in the sheathing member in the endoscope connector device. Thus, there is a possibility that a defect occurs in an electrical circuit component configuring the internal member.

The resin sheathing member and a metal extension member, which configure the endoscope connector device, have different thermal expansion factors due to a difference in a linear expansion coefficiency. For this reason, when a high-pressure steam sterilizer performs autoclave sterilization processing of sterilizing the connector device together with the endoscope while pressurizing and depressurizing, there is a possibility that moisture infiltrates into the sheathing member. Accordingly, there is a possibility that condensation occurs in the internal member.

Since a case, which is the sheathing member, is made of a resin and the light guide end, which is an extending member, is made of a metal, in the connector device disclosed in JP1997-066024A (JP-H9-066024A), there is a possibility of moisture infiltration described above. That is, in the connector device of JP1997-066024A (JP-H9-066024A), the fixing ring is screwed with the attaching ring, or the body frame is screwed with the base part in order to fix the body frame to the case. Due to a difference in a linear expansion coefficiency described above, stress is applied to the case and thereby the case bends. Accordingly, in the connector device of JP1997-066024A (JP-H9-066024A), a gap among a connecting portion between the case body and the base part, a leading-out portion of the light guide, and a leading-out portion of two cable inner tubes is generated, and thus water tightness cannot be secured. In autoclave sterilization, steam infiltrates into the case.

A difference in a thermal expansion factor between the resin sheathing member and the metal extension member causes infiltration of moisture into the sheathing member. However, a method of preventing the infiltration in view of the difference is not mentioned in the connector device of JP1997-066024A (JP-H9-066024A). In addition, the same also applies to the connector device disclosed in JP2007-135956A.

In light of such circumstances, an object of the present invention is to provide an endoscope connector device that can prevent infiltration of moisture into a sheathing member, which occurs due to a difference in a thermal expansion factor between the resin sheathing member and a metal extension member.

According to an aspect of the present invention, in order to achieve the object of the present invention, there is provided an endoscope connector device comprising a metal internal member, a metal extension member that is connected to the internal member, a resin sheathing member that accommodates the internal member and comprises a leading-out hole which leads the extension member to the outside, and an elastic sealing member that is provided on the extension member, and placed in a gap between the extension member and the leading-out hole to seal the inside of the sheathing member.

In the aspect of the present invention, it is preferable that the internal member is disposed to be spaced apart from an inner surface of the sheathing member by being held by the sheathing member via only the sealing member.

In the aspect of the present invention, it is preferable that the sealing member is an O-ring fitted to an outer peripheral surface of the extension member.

In the aspect of the present invention, it is preferable that the internal member has a case member accommodating a substrate or a shield case in which the substrate is disposed, and the endoscope connector device further comprises a light guide rod and a first fixing base for a universal cable connected to an endoscope as the extension member.

In the aspect of the present invention, it is preferable that the endoscope connector device further comprises a second fixing base for a video cable connected to an electrical connector as the extension member.

In the aspect of the present invention, it is preferable that the light guide rod is connected to one end of the case member, and the first fixing base and the second fixing base are connected to the other end of the case member.

In the aspect of the present invention, it is preferable that the sheathing member comprises a plug that holds the light guide rod, and a connector sheathing case that is connected to the plug and accommodates the case member, and the sealing member comprises a first sealing member that causes the plug to hold the light guide rod, a second sealing member that causes the connector sheathing case to hold the first fixing base, and a third sealing member that causes the connector sheathing case to hold the second fixing base.

In the aspect of the present invention, it is preferable that the connector sheathing case is formed in a cylindrical shape, the case member is formed in a rectangular parallelepiped shape, and the case member is accommodated in the connector sheathing case in a posture where a long side of the case member follows an axis of the cylindrical connector sheathing case.

In the aspect of the present invention, it is preferable that the case member comprises a fixing board that fixes the first fixing base and the second fixing base, the fixing board comprises a first attaching hole to which the first fixing base is attached and a second attaching hole to which the second fixing base is attached, and in one fixing base of the first fixing base or the second fixing base and one attaching hole of the first attaching hole or the second attaching hole, to which the one fixing base is attached, an outer surface of the one fixing base has two straight line portions provided to face each other, an inner surface of the one attaching hole has two straight line portions provided to face each other so as to receive the two straight line portions of the one fixing base, and the straight line portions of the one attaching hole are longer than the straight line portions of the one fixing base.

In the aspect of the present invention, it is preferable that the outer surface of the one fixing base has two arc portions provided to face each other so as to connect the two straight line portions of the one fixing base, and the inner surface of the one attaching hole has two arc portions provided to face each other so as to receive the two arc portions of the one fixing base.

In the aspect of the present invention, it is preferable that the one fixing base is the second fixing base.

In the present invention, infiltration of moisture into the sheathing member, which occurs due to a difference in a thermal expansion factor between the resin sheathing member and the metal extension member, can be prevented.

BRIEF DESCRIPTION OF THE DRAWINGS

FIG. 10 is an explanatory view for illustrating anonsensing region of the coupling ring.
FIG. 11A is an explanatory view for illustrating a sensing region of the coupling ring.
FIG. 12 is an explanatory view of operation of treating a diseased site in a patient's body cavity by using the surgical system.
FIG. 21A is a view illustrating the holding of the endoscope insertion part by the endoscope fixing tool of the overtube.
FIG. 21B is a view illustrating the holding of the endoscope insertion part by the endoscope fixing tool of the overtube.

FIG. 43 is a perspective view of a state where the internal member excluding the light guide rod is accommodated in the connector sheathing case.

DESCRIPTION OF THE PREFERRED EMBODIMENTS

Hereinafter, an endoscope connector device according to an embodiment of the present invention will be described with reference to the accompanying drawings.

Figure 1:
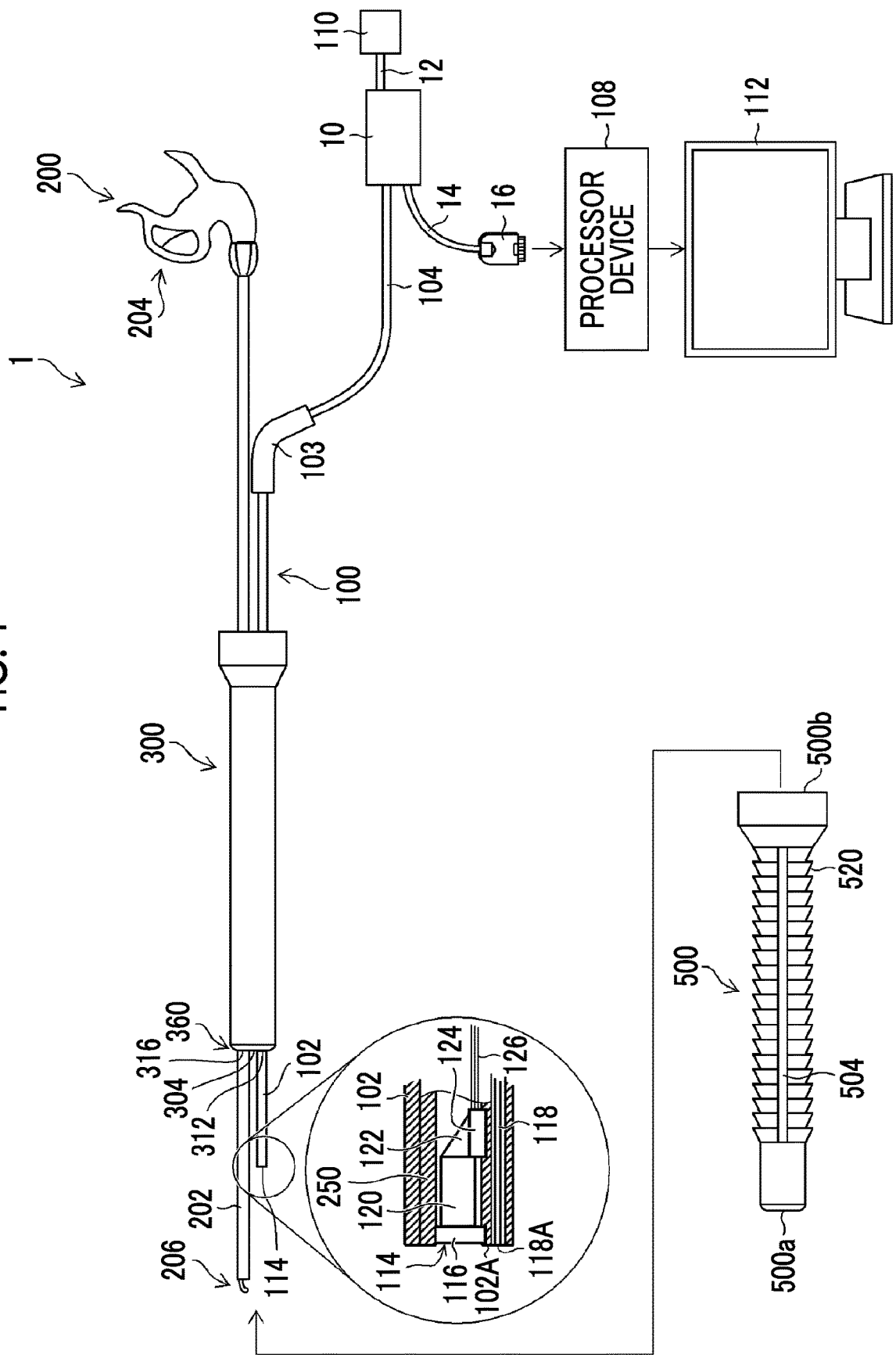
FIG. 1 is a schematic configuration view of a surgical system.

FIG. 1 is a schematic configuration view of a surgical system 1. The surgical system 1 comprises an endoscope 100, a treatment tool 200, an overtube 300, and an outer sheath 500 (also referred to as a sheathing tube), and is used in observation and treatment of a patient's body cavity.

The endoscope 100 is, for example, a hard endoscope such as a laparoscope, and is inserted into the body cavity to observe the inside of the body cavity. The endoscope 100 comprises an elongated hard endoscope insertion part 102 that is inserted into the body cavity, an L-shaped grip part 103 that is consecutively installed on a proximal end part of the endoscope insertion part 102, and a flexible universal cable 104 that has a proximal end part connected to the endoscope insertion part 102 via the grip part 103.

A connector device 10 of the embodiment is provided on a distal end part of the universal cable 104, and a processor device 108 and a light source device 110 are attachably and detachably connected to the endoscope 100 via the connector device 10. In addition, a monitor 112 is connected to the processor device 108. The connector device 10 of the embodiment will be described below.

Figure 2:
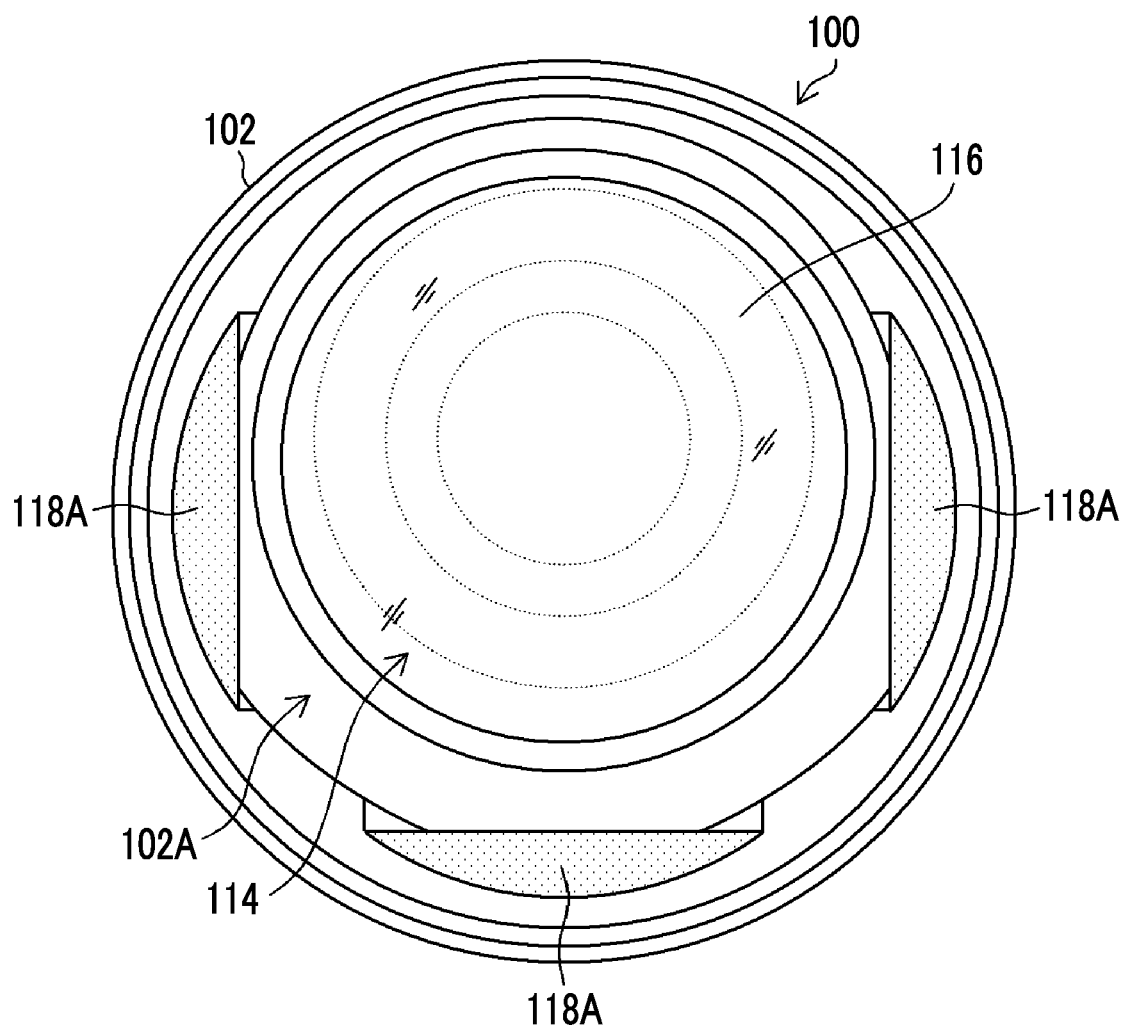
FIG. 2 is a front view of a distal end part of an endoscope insertion part.

FIG. 2 is a front view of the distal end part of the endoscope insertion part 102. FIG. 1 illustrates an enlarged cross section of important parts of the distal end part of the endoscope insertion part 102.

As in FIGS. 1 and 2, an observation part 114 is provided on a distal end surface 102A of the endoscope insertion part 102. The observation part 114 comprises an observation window 116, emission ends 118A, which are distal end parts of light guides 118 disposed in the vicinity of the observation window 116, an image pick-up lens group 120 and a prism 122, which are disposed in a rear part of the observation window 116, and a solid image pickup element 124. As the solid image pickup element 124, a charge coupled device (CCD) image sensor or a complementary metal oxide semiconductor (CMOS) image sensor can be used.

A proximal end part of the light guide 118 is inserted into the endoscope insertion part 102, the grip part 103, and the universal cable 104 so as to be connected to a light guide rod 12 of the connector device 10, and is connected to the light source device 110 via the light guide rod 12. Accordingly, illumination light radiated from the light source device 110 is transmitted via the light guide 118, and is radiated to the front of the endoscope insertion part 102 from the three emission ends 118A of the light guides 118. Accordingly, the inside of the patient's body cavity is illuminated.

Subject light picked up from the observation window 116 is formed as an image onto an imaging surface of the solid image pickup element 124 via the image pick-up lens group 120 and the prism 122, and is converted to an image pickup signal by the solid image pickup element 124. A distal end part of each of signal lines 126 is connected to the solid image pickup element 124 via a base substrate 128 (refer to FIG. 23). A proximal end part of each of the signal lines 126 is inserted into the endoscope insertion part 102, the grip part 103, and the universal cable 104 so as to be connected to the connector device 10. Then, the signal lines 126 are accommodated in a video cable 14 of the connector device 10, and are connected to a flat connector 16 linked to a distal end part of the video cable 14. By the flat connector 16 being connected to the processor device 108, the processor device 108 causes the monitor 112 to display an endoscopic image based on the image pickup signal input from the solid image pickup element 124.

The treatment tool 200 illustrated in FIG. 1 is, for example, a high frequency forcep, and is inserted into the body cavity to treat a diseased site in the body cavity. The treatment tool 200 comprises an elongated treatment tool insertion part 202 inserted into the body cavity, an operating part 204 that is provided on a proximal end side of the treatment tool insertion part 202 and is gripped by an operator, and a treatment part 206 that is provided at a distal end of the treatment tool insertion part 202 and generates a high frequency current by the operation of the operating part 204. Since a structure of an electric scalpel is a known technique, specific description thereof will be omitted.

Without being limited to the electric scalpel, the treatment tool 200 may be other treatment tools, for example, a forcep, a laser probe, a suture device, a needle holder, an ultrasonic device, an aspirator, and the like.

The overtube 300 allows the endoscope insertion part 102 and the treatment tool insertion part 202 to be inserted therein from the proximal end side and to be delivered from the distal end side. By inserting the overtube 300 into a body wall and having the proximal end side thereof disposed outside the body and the distal end side thereof disposed within the body cavity, the endoscope insertion part 102 and the treatment tool insertion part 202 are guided into the body cavity with one overtube 300. In addition, as will be described below in detail, the overtube 300 has an interlocking function of moving the endoscope insertion part 102 and the treatment tool insertion part 202 forward and backward in an interlocking manner. Accordingly, for example, the endoscope insertion part 102 can also be moved forward and backward by the forward and backward movement operation of only the treatment tool insertion part 202, and a suitable endoscopic image can be obtained without performing the forward and backward movement operation of the endoscope insertion part 102.

The outer sheath 500 is formed in a tubular shape, and has a distal end opening 500a, a proximal end opening 500b, and an insertion passage (not illustrated) into which the overtube 300 is inserted rotatably about a longitudinal axis from the proximal end opening 500b toward the distal end opening 500a. In an outer peripheral part of the outer sheath 500, multiple horizontal grooves 520 are provided along a circumferential direction thereof, and vertical grooves 504 along a longitudinal axial direction thereof are provided at a plurality of parts in the circumferential direction of the outer sheath 500. Accordingly, in a state where the overtube 300 is inserted in the body wall together with the outer sheath 500, the horizontal grooves 520 each restrict forward and backward movement of the outer sheath 500 with respect to the body wall, and the vertical grooves 504 each restrict rotation of the outer sheath 500 in the circumferential direction with respect to the body wall. Hence, unintended rotation and forward and backward movement of the overtube 300, which is inserted in the outer sheath 500, with respect to the body wall can be prevented. Accordingly, it is possible to prevent a position of a distal end of the endoscope insertion part 102 from fluctuating and an observation visual field from unintentionally fluctuating.

Next, a configuration of the overtube 300 will be described.

Figure 3:
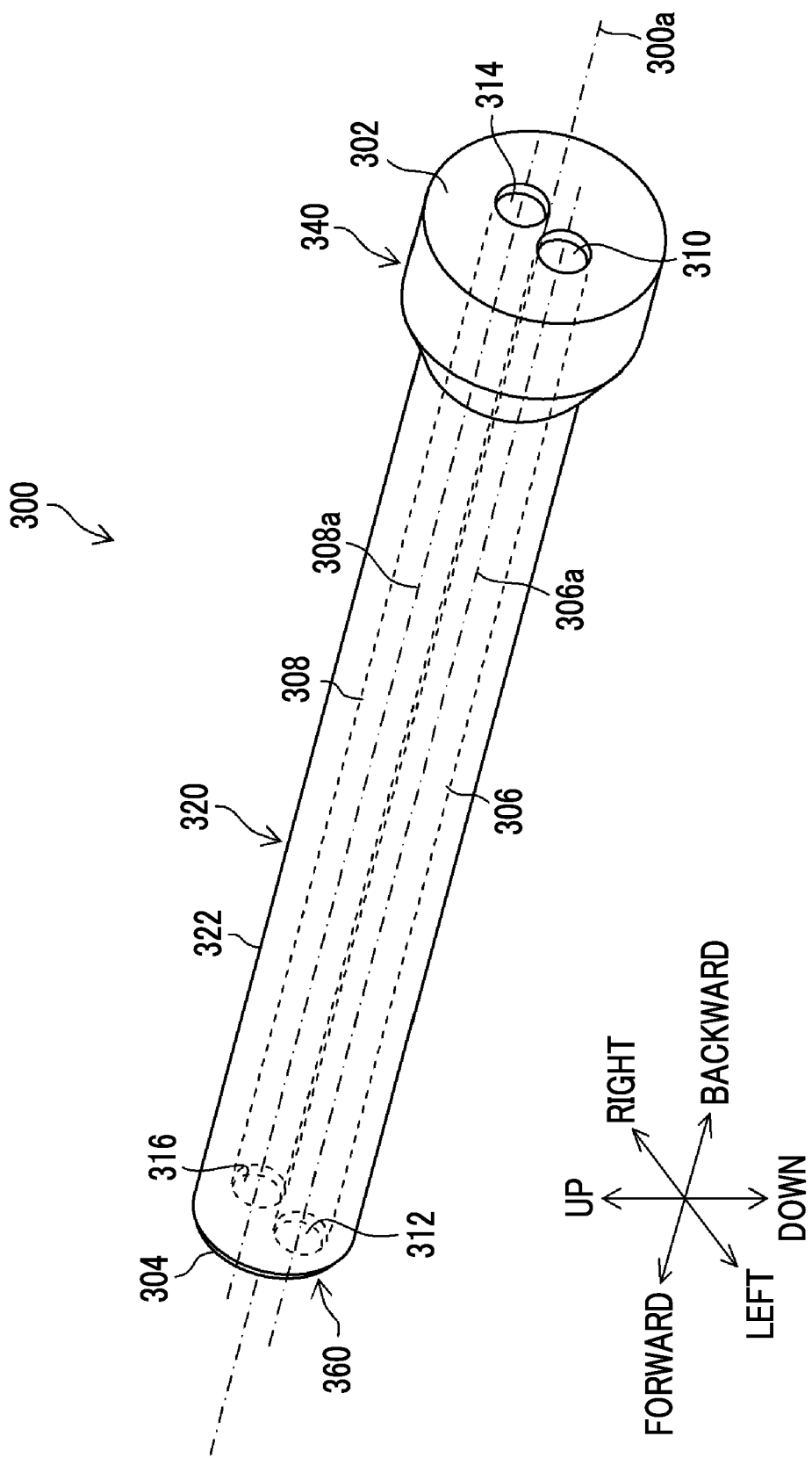
FIG. 3 is an external perspective view of an overtube.

FIG. 3 is an external perspective view of the overtube 300. The overtube 300 has an elongated cylindrical shape as a whole, and has a distal end, a proximal end, and a longitudinal axis 300a. The overtube 300 has, along the longitudinal axis 300a, an endoscope insertion passage 306 into which the endoscope insertion part 102 (refer to FIG. 1) is inserted so as to be movable forward and backward and a treatment tool insertion passage 308 into which the treatment tool insertion part 202 is inserted so as to be movable forward and backward. The endoscope insertion passage 306 and the treatment tool insertion passage 308 are disposed to be parallel to each other, and are parallel to the longitudinal axis 300a.

The reference sign "306a" in FIG. 3 is an endoscope insertion axis that corresponds to a central axis of the endoscope insertion passage 306. In addition, the reference sign "308a" in FIG. 3 is a treatment tool insertion axis that corresponds to a central axis of the treatment tool insertion passage 308. Although the longitudinal axis 300a, the endoscope insertion axis 306a, and the treatment tool insertion axis 308a are disposed on the same plane in the embodiment, a configuration of being disposed on the same plane does not necessarily have to be adopted.

Regarding the position and orientation of a space where the overtube 300 is disposed, terms called "forward", "backward", "left", "right", "up", and "down" are used with an orientation from the proximal end surface 302 to a distal end surface 304 in a direction along the longitudinal axis 300a defined as forward and with an orientation from the longitudinal axis 300a to the treatment tool insertion axis 308a defined as the right.

A first proximal end opening 310 through which the endoscope insertion part 102 is inserted into the endoscope insertion passage 306 and a second proximal end opening 314 through which the treatment tool insertion part 202 is inserted into the treatment tool insertion passage 308 are provided in the proximal end surface 302 of the overtube 300. In addition, a first distal end opening 312 that allows the endoscope insertion part 102 inserted in the endoscope insertion passage 306 to be delivered forward and a second distal end opening 316 that allows the treatment tool insertion part 202 inserted in the treatment tool insertion passage 308 to be delivered forward are provided in the distal end surface 304 of the overtube 300.

In addition, the overtube 300 is configured by an overtube long tubular part 320 that has a shape extending along the longitudinal axis 300a, a proximal end cap 340 attached to a proximal end of the overtube long tubular part 320, and a distal end cap 360 attached to a distal end of the overtube long tubular part 320.

The proximal end cap 340 is formed of a hard resin, a metal, or the like in a cylindrical shape of which a diameter is larger than an outer diameter of the overtube long tubular part 320, and a rear end surface thereof configures the proximal end surface 302. In addition, the distal end cap 360 is formed of a hard resin, a metal, or the like, and a front end surface thereof configures the distal end surface 304.

The overtube long tubular part 320 has a long tubular body 322 formed of a hard resin, a metal, or the like in an elongated cylindrical shape of which a central axis is the longitudinal axis 300a. In addition, the overtube long tubular part 320 has, in the long tubular body 322, the endoscope insertion passage 306, the treatment tool insertion passage 308, and a slider 400 (refer to FIGS. 4A and 4B) that interlocks the endoscope insertion part 102 and the treatment tool insertion part 202 and moves the endoscope insertion part and the treatment tool insertion part forward and backward in a direction of the longitudinal axis 300a.

Figure 4A:
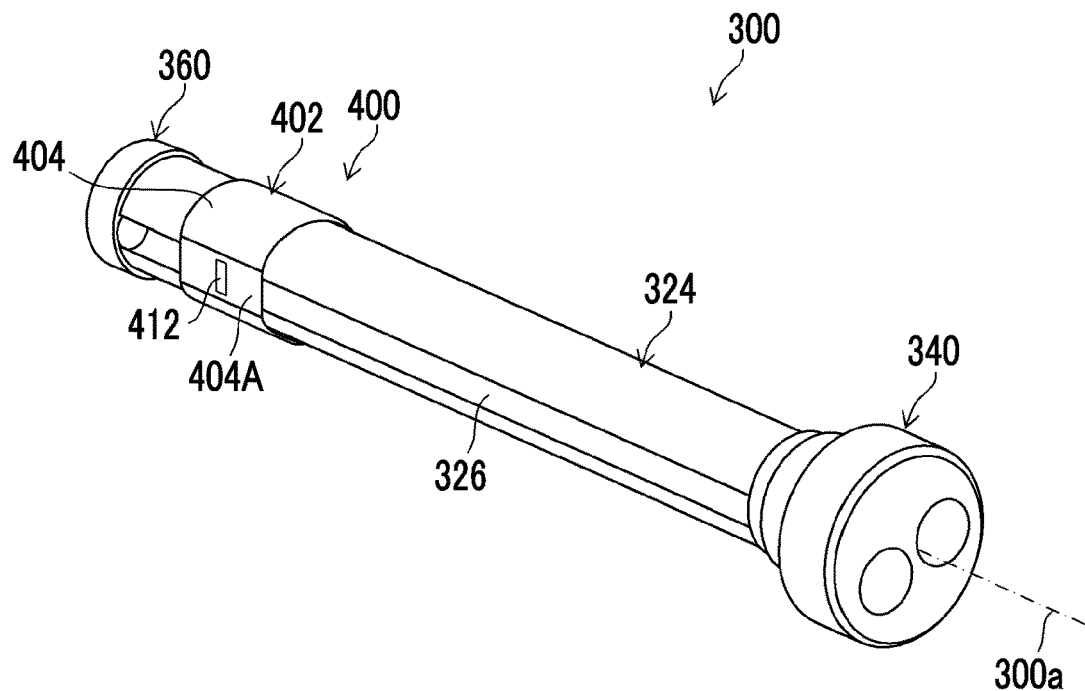
FIG. 4A is an external perspective view illustrated without a long tubular body of an overtube long tubular part.
Figure 4B:
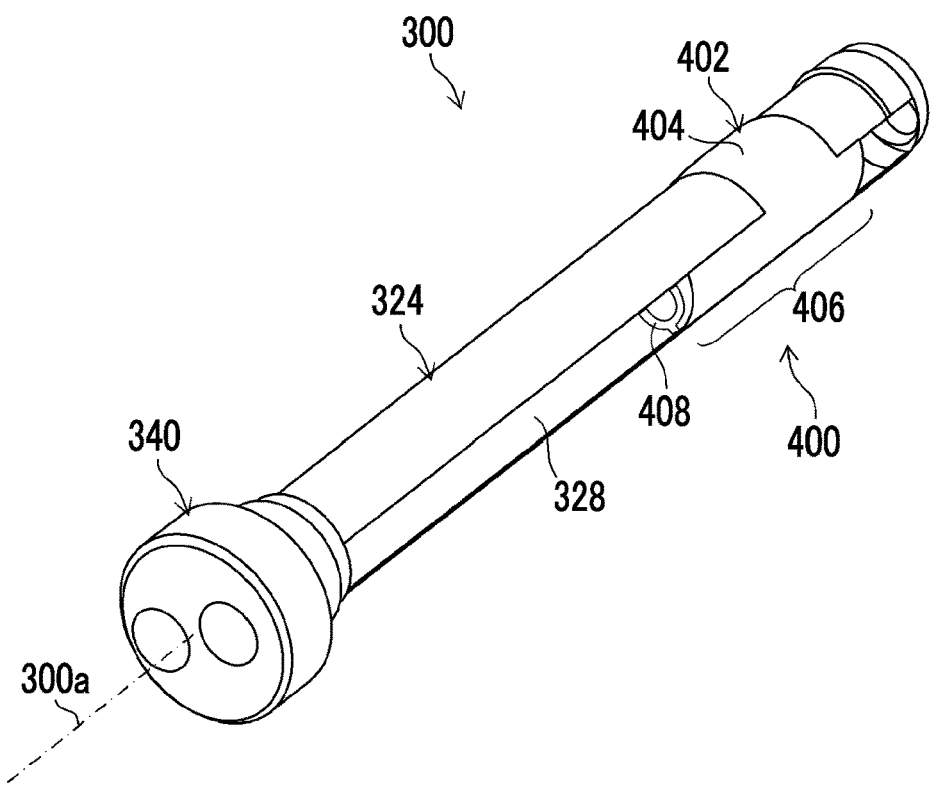
FIG. 4B is an external perspective view illustrated without the long tubular body of the overtube long tubular part.

FIGS. 4A and 4B are external perspective views illustrating the overtube 300 with the long tubular body 322 of the overtube long tubular part 320 omitted. As illustrated in FIGS. 4A and 4B, a partition wall member 324 having a substantially cylindrical shape extending along the longitudinal axis 300a and the slider 400 that is guided by the partition wall member 324 and is movable forward and backward in a forward-backward direction are provided in the long tubular body 322.

Figure 5:
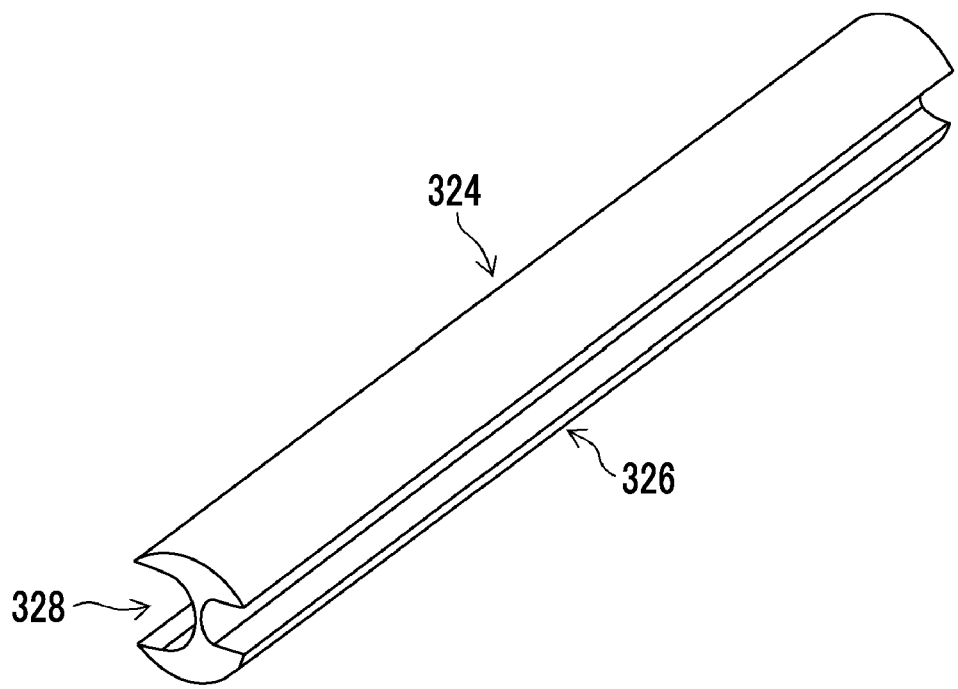
FIG. 5 is an external perspective view of a partition wall member.

FIG. 5 is an external perspective view of the partition wall member 324. The partition wall member 324 is a solid insulator formed of, for example, a resin, and extends from the proximal end cap 340 to the distal end cap 360 inside the long tubular body 322 of FIG. 3. As in FIG. 5, in a side surface of the partition wall member 324, each of an endoscope guide groove 326 and a treatment tool guide groove 328, which extends parallel to the longitudinal axis 300a from a proximal end to a distal end of the partition wall member 324, is formed. The endoscope guide groove 326 forms a part of the endoscope insertion passage 306 (refer to FIG. 3), and the treatment tool guide groove 328 forms a part of the treatment tool insertion passage 308. In addition, the partition wall member 324 forms a partition wall between the endoscope insertion passage 306 and the treatment tool insertion passage 308.

By virtue of the partition wall member 324, the endoscope insertion part 102 and the treatment tool insertion part 202 inserted in the overtube 300 reliably proceed through the inside of the insertion passages without falling out of regions of the endoscope insertion passage 306 and the treatment tool insertion passage 308 corresponding thereto, respectively. For this reason, an insertion task of the endoscope insertion part 102 and the treatment tool insertion part 202 with respect to the overtube 300 becomes easy. In addition, contact between the endoscope insertion part 102 and the treatment tool insertion part 202 inside the overtube 300 is prevented.

Referring back to FIGS. 4A and 4B, the slider 400 is externally fitted to an outer peripheral part of the partition wall member 324 inside the long tubular body 322 of FIG. 3, and is a ring-shaped moving body that moves forward and backward with respect to the partition wall member 324 along the direction of the longitudinal axis 300a.

Figure 6:
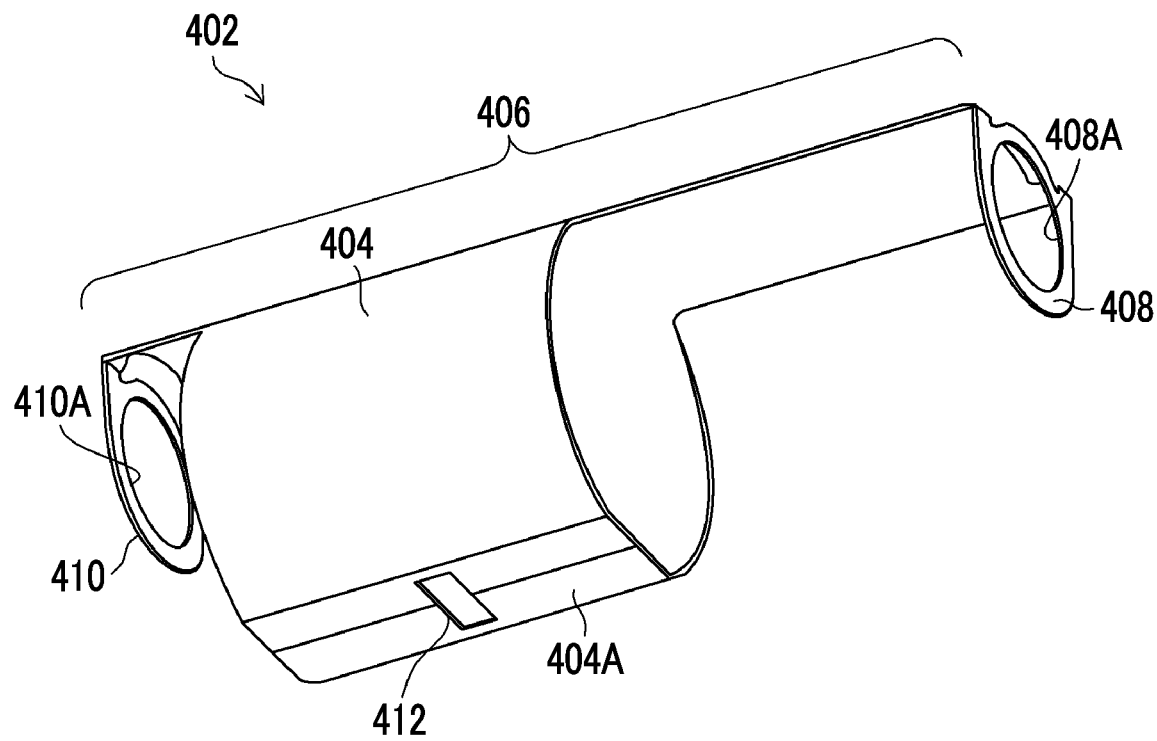
FIG. 6 is an external perspective view of a coupling ring configuring a part of a slider.
Figure 7:
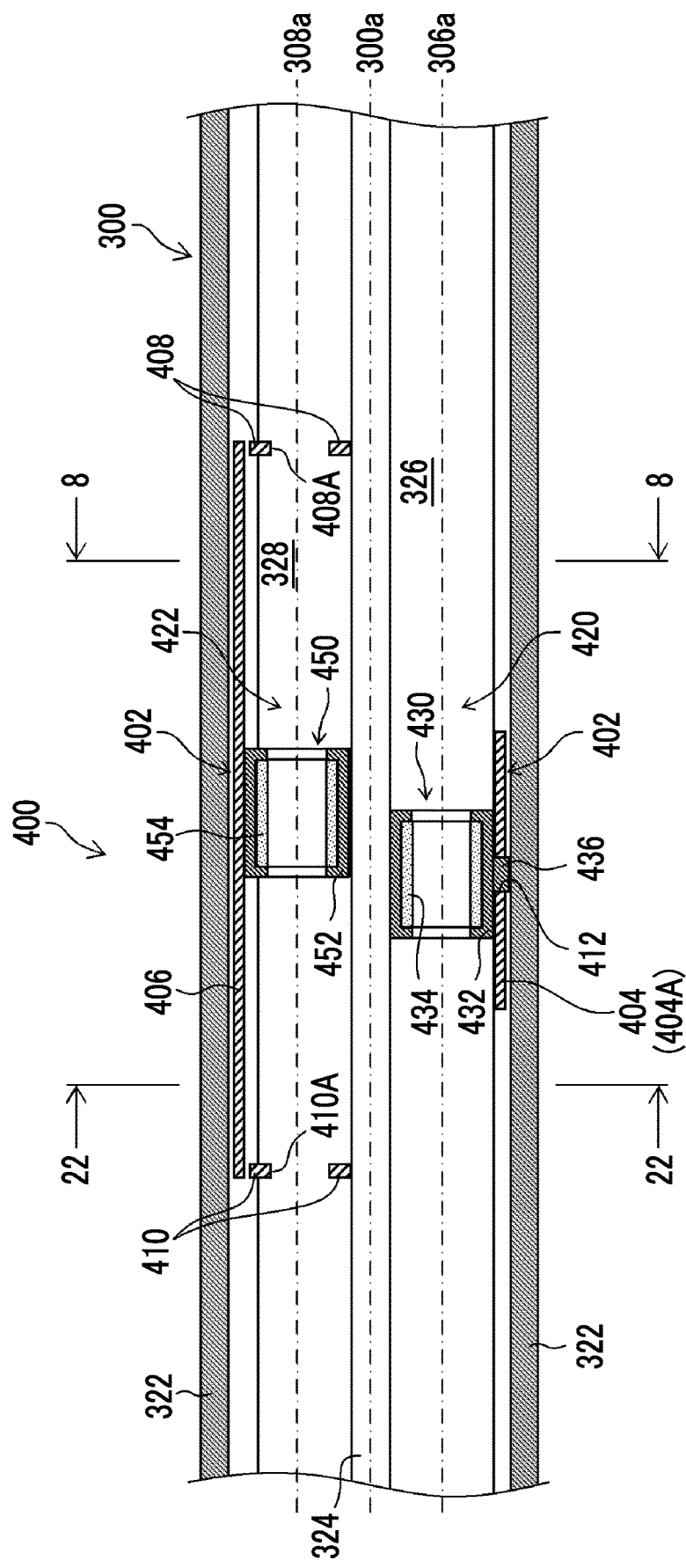
FIG. 7 is a cross-sectional view of the overtube and the slider taken along a horizontal plane orthogonal to an upward-downward direction.

FIG. 6 is an external perspective view of a coupling ring 402 configuring a part of the slider 400. In addition, FIG. 7 is a cross-sectional view of the overtube 300 and the slider 400 taken along a horizontal plane that includes the longitudinal axis 300a and is orthogonal to an upward-downward direction.

As illustrated in FIGS. 4A, 4B, 6, and 7, the slider 400 has an endoscope coupling part 420 disposed inside the endoscope guide groove 326, a treatment tool coupling part 422 disposed inside the treatment tool guide groove 328, and the metal coupling ring 402 that integrally interlocks the endoscope coupling part 420 and the treatment tool coupling part 422.

As in FIG. 6, the coupling ring 402 has a tubular ring part 404, which surrounds an outer periphery of the partition wall member 324 in a circumferential direction, and an arm part 406. The ring part 404 comes into contact with or approaches a portion of an outer peripheral surface of the partition wall member 324 other than the endoscope guide groove 326 and the treatment tool guide groove 328. In addition, the arm part 406 extends from a portion of the ring part 404 facing the treatment tool guide groove 328 in the forward-backward direction along the treatment tool guide groove 328.

A rear restriction end 408 and a front restriction end 410 that are disposed to be inserted inside the treatment tool guide groove 328 are provided at a distal end and a proximal end of the arm part 406, respectively. An opening 408A and an opening 410A into which the treatment tool insertion part 202 is inserted are provided in the rear restriction end 408 and the front restriction end 410, respectively. Thus, the rear restriction end 408 and the front restriction end 410 restrict forward and backward movement of the treatment tool coupling part 422 (treatment tool fixing tool 450 to be described below), which is disposed therebetween inside the treatment tool guide groove 328, in the forward-backward direction.

A flat first engaging part 404A that is parallel to an opening of the endoscope guide groove 326 and extends in the forward-backward direction is formed in a portion of the ring part 404 facing the endoscope guide groove 326. The rotation of the coupling ring 402 around the longitudinal axis 300a (hereinafter, abbreviated to around the longitudinal axis) with respect to the partition wall member 324 is restricted by the first engaging part 404A, the rear restriction end 408, and the front restriction end 410. In addition, an engagement hole 412 to be described below is formed in the first engaging part 404A.

The coupling ring 402 is supported by the partition wall member 324 so as to be movable forward and backward in the forward-backward direction, and is supported by the partition wall member 324 in a state where movement in the upward-downward direction and in a leftward-rightward direction and rotation in all directions are restricted. In addition, the coupling ring 402 moves forward and backward within a movable range having a position where the rear restriction end 408 of the coupling ring 402 abuts against the proximal end cap 340 as a rear end and having a position where the front restriction end 410 of the coupling ring 402 abuts against the distal end cap 360 as a front end.

Figure 8:
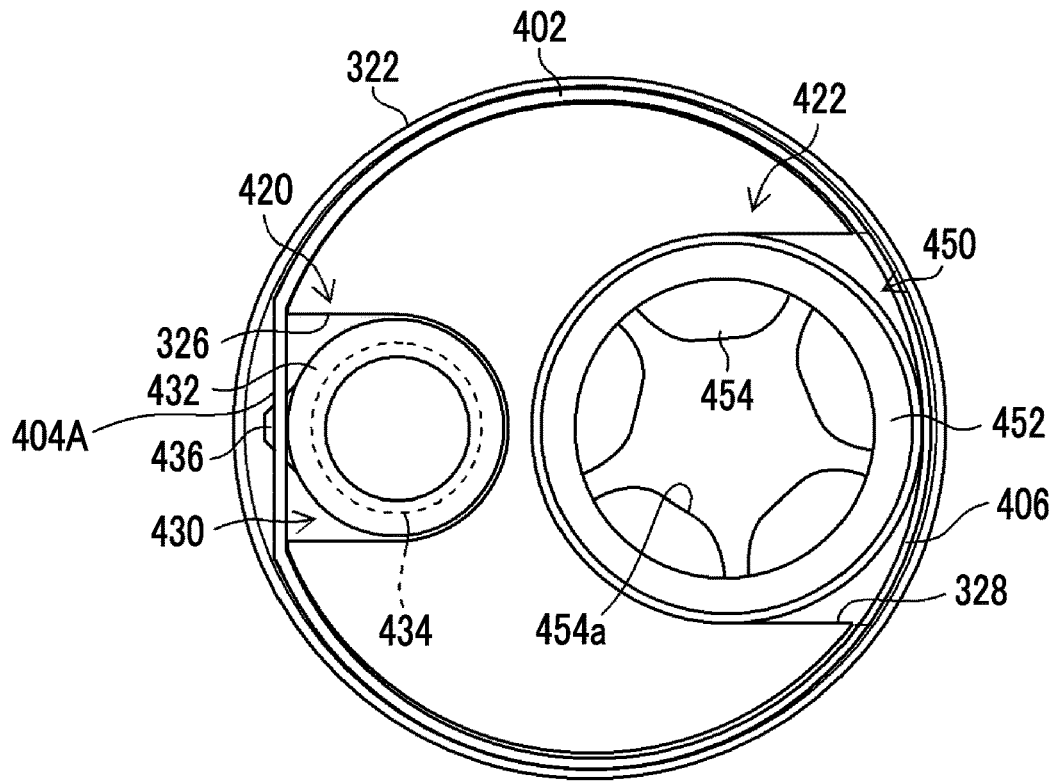
FIG. 8 is a cross-sectional view taken along line "8-8" in FIG. 7.
Figure 9A:
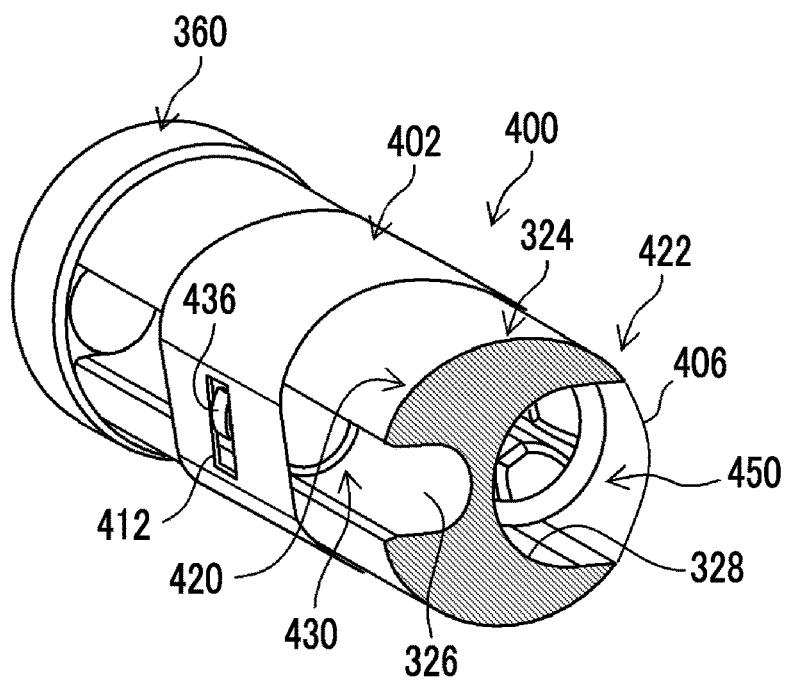
FIG. 9A is a perspective view illustrating the overtube in FIG. 4A, which is taken along a plane perpendicular to a longitudinal axis.
Figure 9B:
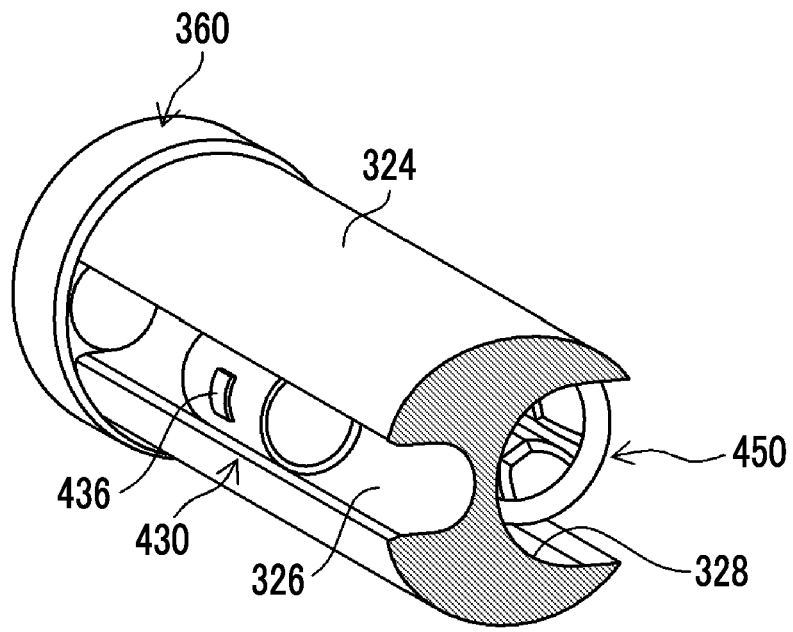
FIG. 9B is a perspective view illustrated with the coupling ring in FIG. 9A omitted.
Figure 9C:
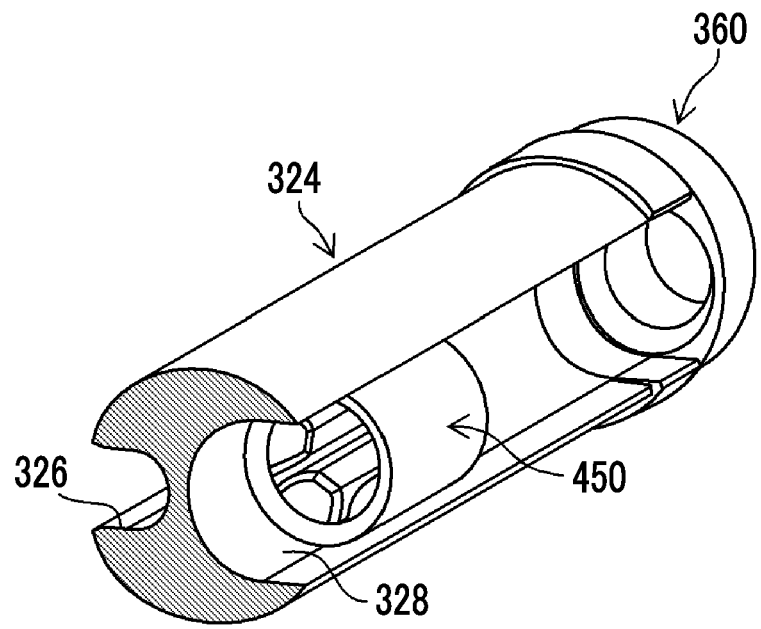
FIG. 9C is a perspective view of the overtube of FIG. 9B seen from a different direction.

FIG. 8 is a cross-sectional view taken along line "8-8" in FIG. 7. FIG. 9A is a perspective view illustrating the overtube 300 that is cut along a plane perpendicular to the longitudinal axis 300a at a position orthogonal to the arm part 406 extending further to the proximal end side than the ring part 404 does in FIG. 4A. FIG. 9B is a perspective view illustrated with the coupling ring 402 in FIG. 9A omitted. FIG. 9C is a perspective view of the overtube 300 of FIG. 9B seen from a different direction.

As illustrated in FIGS. 7 and 8 and FIGS. 9A to 9C, the endoscope coupling part 420 is disposed in the endoscope guide groove 326, and is coupled to the endoscope insertion part 102 inserted in the endoscope guide groove 326. In addition, the treatment tool coupling part 422 is disposed in the treatment tool guide groove 328, and is coupled to the treatment tool insertion part 202 inserted in the treatment tool guide groove 328.

The endoscope coupling part 420 is disposed inside the endoscope guide groove 326, and has an endoscope fixing tool 430 that moves forward and backward in the forward-backward direction along the endoscope insertion passage 306 formed by the endoscope guide groove 326. The endoscope fixing tool 430 holds the endoscope insertion part 102 in the slider 400. The endoscope fixing tool 430 is configured by a metal tubular holding frame 432, which approaches or comes into contact with an inner wall surface of the endoscope guide groove 326, and a tubular endoscope elastic holding body 434, such as an O-ring which is fixed inside the holding frame 432 and is formed of an elastic material, such as elastic rubber.

Since the holding frame 432 has a shape that makes it impossible to move (rotate) in a direction around an axis inside the endoscope guide groove 326, only forward and backward movement in the forward-backward direction is allowed for the endoscope fixing tool 430 in the endoscope guide groove 326. In addition, a cross section of an inner peripheral surface of the holding frame 432, which is taken along the forward-backward direction, is formed in a recessed shape over an entire inner periphery. The endoscope elastic holding body 434 is fitted and fixed to a recessed part of the inner peripheral surface of the holding frame 432. Accordingly, even in a case where the endoscope elastic holding body 434 contains oil and cannot be fixed to the holding frame 432 with an adhesive, the endoscope elastic holding body 434 can be fixed inside the holding frame 432. For this reason, a part of the holding frame 432 (end part in the forward-backward direction) comes into contact with an outer peripheral surface of the endoscope insertion part 102.

At a position facing the opening of the endoscope guide groove 326 on an outer peripheral surface of the holding frame 432, a protrusion 436 that protrudes toward the outside of the opening is provided. The protrusion 436 is inserted into the engagement hole 412 formed in the first engaging part 404A, and is locked in the forward-backward direction. That is, the first engaging part 404A having the engagement hole 412 is engaged with the holding frame 432 via the protrusion 436. Accordingly, relative forward and backward movement of the endoscope fixing tool 430 in the forward-backward direction with respect to the coupling ring 402 is restricted. Hence, the coupling ring 402 and the endoscope fixing tool 430 integrally move forward and backward in the forward-backward direction.

The endoscope elastic holding body 434 elastically holds the endoscope insertion part 102 by being brought into pressure contact with the outer peripheral surface of the endoscope insertion part 102 inserted therein. Accordingly, an endoscope longitudinal axis 100a, which is a longitudinal axis of the endoscope insertion part 102, is disposed substantially coaxially with the endoscope insertion axis 306a. Since an endoscope holding surface 434a is brought into pressure contact with the outer peripheral surface of the endoscope insertion part 102 by an elastic force, the rotation of the endoscope 100 in the circumferential direction of which a center is the endoscope longitudinal axis 100a is allowed. In addition, the endoscope elastic holding body 434 can freely adjust a holding position of the endoscope insertion part 102 in the forward-backward direction.

The treatment tool coupling part 422 has the treatment tool fixing tool 450 disposed between the rear restriction end 408 and the front restriction end 410 of the arm part 406, which are inside the treatment tool guide groove 328. The treatment tool fixing tool 450 holds the treatment tool insertion part 202 in the slider 400. In other words, the treatment tool 200 is locked to the slider 400 by means of the treatment tool fixing tool 450. The treatment tool fixing tool 450 is movable forward and backward in the forward-backward direction between the rear restriction end 408 and the front restriction end 410 along the treatment tool guide groove 328.

The treatment tool fixing tool 450 is configured by a metal tubular frame 452, which approaches or comes into contact with an inner wall surface of the treatment tool guide groove 328, and a tubular treatment tool elastic holding body 454, such as an O-ring which is fixed inside the frame 452 and is formed of an elastic material, such as elastic rubber. An inner peripheral surface of the treatment tool elastic holding body 454 is formed in a shape in which unevenness is repeated with respect to the circumferential direction so as to be capable of being suitably engaged with a plurality of types of treatment tool insertion parts 202 having diameters different from each other.

The treatment tool elastic holding body 454 has a treatment tool holding surface 454a that elastically holds the treatment tool insertion part 202 by being brought into pressure contact with the outer peripheral surface of the treatment tool insertion part 202 inserted therein. Accordingly, a central axis (longitudinal axis) of the treatment tool insertion part 202 is disposed substantially coaxially with the treatment tool insertion axis 308a. Since the treatment tool holding surface 454a comes into pressure contact with the outer peripheral surface of the treatment tool insertion part 202 by the elastic force, a holding position of the treatment tool insertion part 202 in the forward-backward direction by the treatment tool holding surface 454a can be freely adjusted.

The treatment tool fixing tool 450 integrally moves forward and backward in an interlocking manner with the forward and backward movement of the treatment tool insertion part 202 in the forward-backward direction. In this case, as described above, the treatment tool fixing tool 450 is movable forward and backward in the forward-backward direction between the rear restriction end 408 and the front restriction end 410 along the treatment tool guide groove 328. That is, the arm part 406 allows the forward and backward movement of the treatment tool fixing tool 450 in the forward-backward direction with respect to the coupling ring 402 in a range from a position where the treatment tool fixing tool 450 abuts against the rear restriction end 408 to a position where the treatment tool fixing tool abuts against the front restriction end 410, and restricts the forward and backward movement to the range.

In addition, the treatment tool fixing tool 450 rotates inside the treatment tool guide groove 328 in an interlocking manner with the rotation of the treatment tool insertion part 202 around the longitudinal axis.

FIG. 10 is an explanatory view for illustrating a non-sensing region of the coupling ring 402. In a case where a range where the endoscope fixing tool 430 is movable forward and backward with respect to the coupling ring 402 is set as a first range and a range where the treatment tool fixing tool 450 is movable forward and backward with respect to the coupling ring 402 is set as a second range, the first range becomes zero since the forward and backward movement of the endoscope fixing tool 430 in the forward-backward direction with respect to the first engaging part 404A of the coupling ring 402 is restricted. On the contrary, the second range is a range between the rear restriction end 408 and the front restriction end 410 as described above. Accordingly, the coupling ring 402 has a non-sensing region where the forward and backward movement of any one of the treatment tool fixing tool 450 or the endoscope fixing tool 430 is not interlocked with the forward and backward movement of the other.

Since the endoscope 100 does not move forward and backward with respect to forward and backward movement operation in the non-sensing region (forward and backward movement in a range where the treatment tool fixing tool 450 and the rear restriction end 408 or the front restriction end 410 do not abut against each other), a range of an observation site, such as a distal end site of the treatment tool 200 and a body cavity inner site, which is to be displayed on the monitor 112 as an endoscopic image, does not vary, and the size of an image of the observation site can be prevented from fluctuating according to minute displacement of the treatment tool 200. Accordingly, a sense of perspective can be suitably maintained, and a stable endoscopic image can be obtained.

Figure 11B:
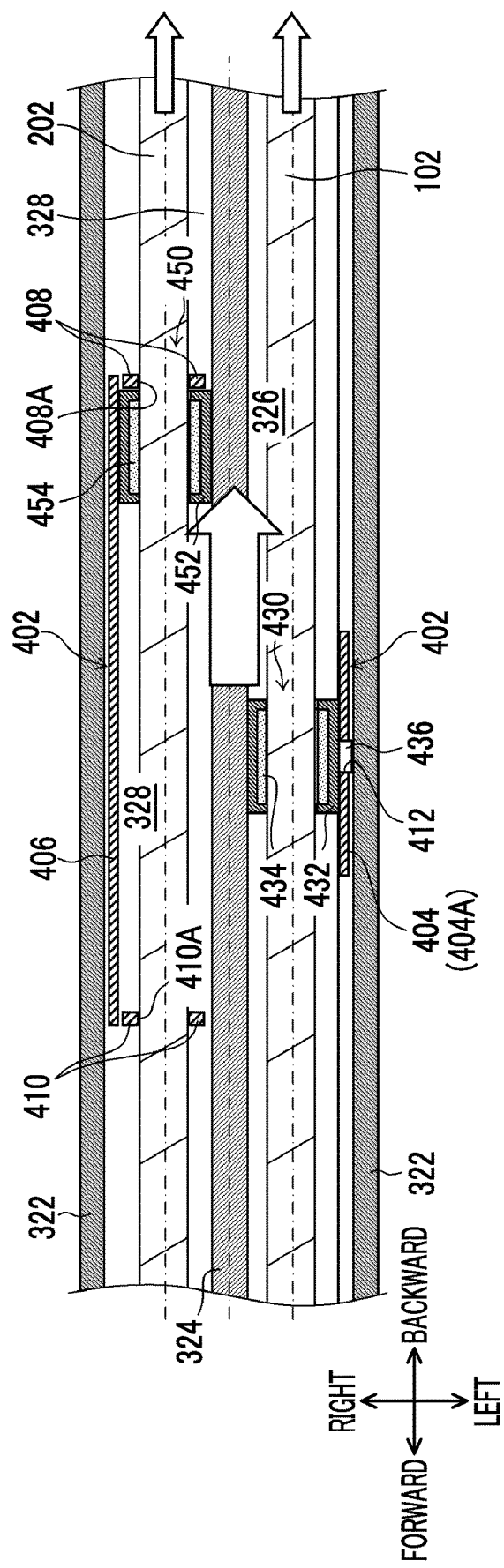
FIG. 11B is an explanatory view for illustrating the sensing region of the coupling ring.

FIGS. 11A and 11B are explanatory views for illustrating a sensing region of the coupling ring 402. In a case where the treatment tool fixing tool 450 has moved forward and backward in the forward-backward direction, or in a case where the coupling ring 402 has moved forward and backward in the forward-backward direction along with the endoscope fixing tool 430, the treatment tool fixing tool 450 abuts against the rear restriction end 408 or the front restriction end 410. In this state, the coupling ring 402 has a sensing region where the forward and backward movement of any one of the endoscope fixing tool 430 or the treatment tool fixing tool 450 (the forward and backward movement in a direction where the treatment tool fixing tool 450 and the rear restriction end 408 or the front restriction end 410 are not spaced apart from each other) is interlocked with forward and backward movement of the other.

Since the endoscope 100 moves forward and backward with respect to forward and backward movement operation in the sensing region, a range of an observation site that appears in an endoscopic image displayed on the monitor 112 is continuously changed so as to follow the forward and backward movement of the treatment tool 200. Accordingly, since the sizes of images of observation sites other than the distal end site of the treatment tool 200 that appears in the endoscopic image and the size of the range of the observation site vary according to the operation of the treatment tool 200, an operator can simply obtain a desired image.

As described above, the slider 400 has the non-sensing region where the forward and backward movement of any one of the endoscope insertion part 102 coupled to the endoscope fixing tool 430 or the treatment tool insertion part 202 coupled to the treatment tool fixing tool 450 in the forward-backward direction (axial direction) is not interlocked with the forward and backward movement of the other and the sensing region where the forward and backward movement of any one of the endoscope insertion part or the treatment tool insertion part is interlocked with the forward and backward movement of the other. That is, the endoscope insertion part 102 is interlocked with the forward and backward movement of the treatment tool insertion part 202 in the axial direction at a distance by the slider 400.

The working of the overtube 300 configured as described above will be described.

First, in a state where an inner needle (not illustrated) is inserted in the overtube 300, the overtube 300 is inserted into the patient's body wall and the inner needle is removed. After then, a pneumoperitoneum gas is injected into the body cavity. After then, as illustrated in (A) of FIG. 12, the endoscope insertion part 102 and the treatment tool insertion part 202 are mounted onto the overtube 300 by inserting the endoscope insertion part 102 and the treatment tool insertion part 202 into the endoscope insertion passage 306 and the treatment tool insertion passage 308 of the overtube 300, respectively. Although detailed description of the inner needle is omitted, the inner needle has two shaft-like needle parts corresponding to the endoscope insertion passage 306 and the treatment tool insertion passage 308 of the overtube 300, respectively, and distal ends of the two needle parts each are provided with an edge part.

At this time, the endoscope insertion part 102 is reliably guided to a position, at which the endoscope fixing tool 430 of the slider 400 is inserted, by the endoscope guide groove 326 of the partition wall member 324, and is coupled to the endoscope fixing tool 430. Similarly, the treatment tool insertion part 202 is guided reliably to a position, at which the treatment tool fixing tool 450 of the slider 400 is inserted, by the treatment tool guide groove 328 of the partition wall member 324, and is coupled to the treatment tool fixing tool 450.

Figure 13:
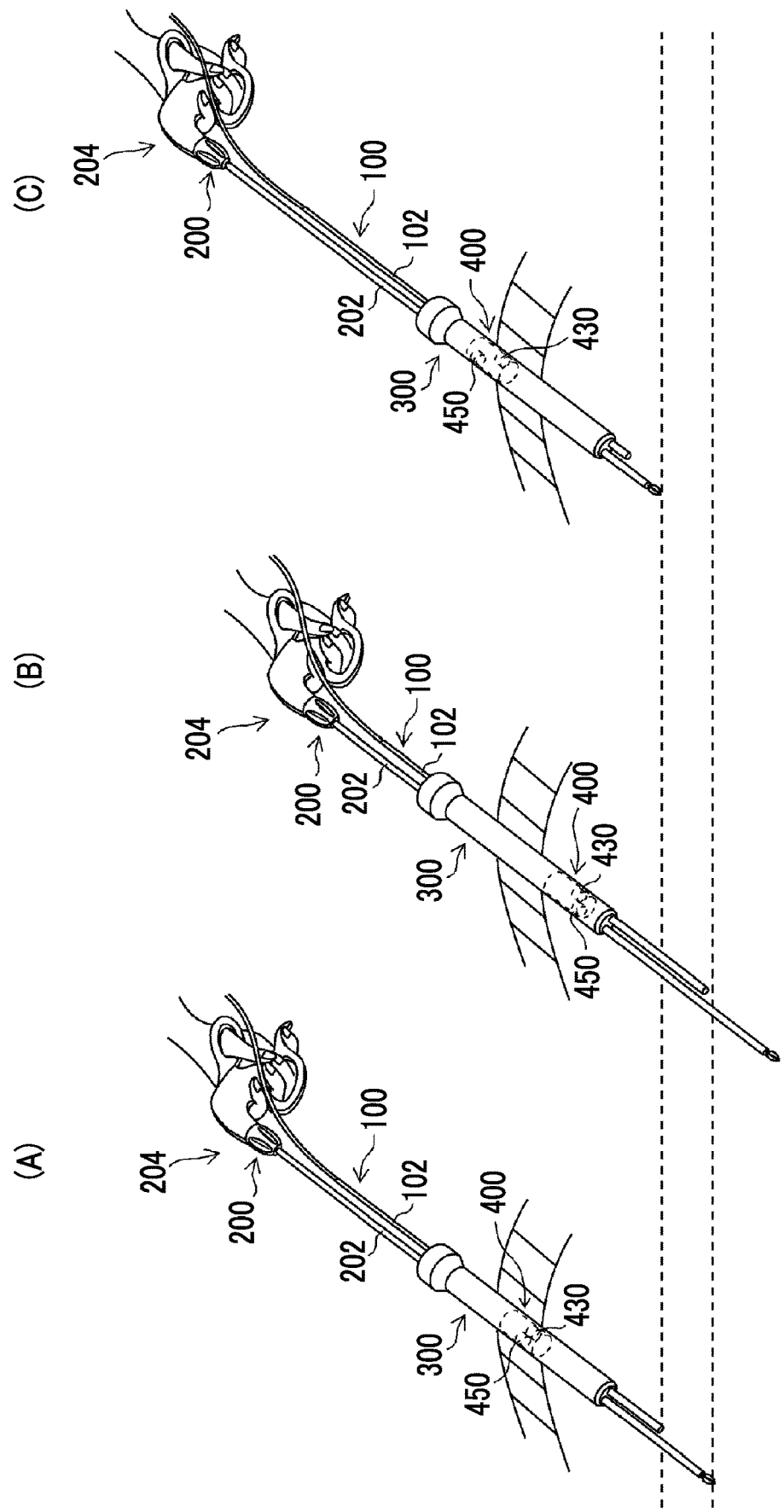
FIG. 13 is an explanatory view of the operation of treating the diseased site in the patient's body cavity by using the surgical system.

In FIG. 12 and FIG. 13, which is to be described below, the outer sheath 500 illustrated in FIG. 1 is fitted to the overtube 300 although the outer sheath 500 is not illustrated. However, it is also possible to use the overtube 300 without the outer sheath 500 fitted thereto.

The state of (A) of FIG. 12 is a state illustrated in FIG. 10. FIG. 10 is a cross-sectional view illustrating a state of the slider 400 coupled to the endoscope insertion part 102 and the treatment tool insertion part 202, and illustrates a state where the treatment tool fixing tool 450 has not reached any one of the front end or the rear end of the movable range with respect to the coupling ring 402 (arm part 406). That is, a state where the treatment tool fixing tool 450 has not reached any one of the rear restriction end 408 or the front restriction end 410 is illustrated.

At this time, in a case where the operator minutely moves the treatment tool insertion part 202 forward with his/her hand that is gripping the operating part 204 of the treatment tool 200, only the treatment tool fixing tool 450 moves forward within the movable range thereof with respect to the coupling ring 402, and the coupling ring 402 does not move with respect to the overtube 300 (overtube long tubular part 320).

For that reason, with respect to the forward movement of the treatment tool insertion part 202 until the treatment tool fixing tool 450 reaches the front end (front restriction end 410) of the movable range thereof with respect to the coupling ring 402, as illustrated in (B) of FIG. 12, only the treatment tool insertion part 202 moves forward in a state where the endoscope insertion part 102 is stationary. That is, the slider 400 has the non-sensing region where the endoscope insertion part 102 is not interlocked with the forward and backward movement of the treatment tool insertion part 202, and the forward movement operation of the treatment tool 200 at this time becomes forward and backward movement operation of the slider 400 in the non-sensing region.

Similarly, in a case where the operator minutely moves the treatment tool insertion part 202 backward with his/her hand that is gripping the operating part 204 of the treatment tool 200 in the state illustrated in FIG. 10, only the treatment tool fixing tool 450 moves backward within the movable range thereof with respect to the coupling ring 402, and the coupling ring 402 does not move with respect to the overtube 300 (overtube long tubular part 320).

For that reason, with respect to the backward movement of the treatment tool insertion part 202 until the treatment tool fixing tool 450 reaches the rear end (rear restriction end 408) of the movable range thereof with respect to the coupling ring 402, as illustrated in (C) of FIG. 12, only the treatment tool insertion part 202 moves backward in a state where the endoscope insertion part 102 is stationary. That is, the backward movement operation of the treatment tool 200 of this time becomes the backward movement operation of the slider 400 in the non-sensing region.

Hence, since the endoscope 100 does not move forward and backward with respect to the minute forward and backward movement operation of the treatment tool 200, that is, the forward and backward movement operation thereof in the non-sensing region, the range of an observation site, such as the distal end site of the treatment tool 200 or the body cavity inner site, to be displayed on the monitor 112 as an endoscopic image does not vary, and the size of an image of the observation site can be prevented from fluctuating according to minute displacement of the treatment tool 200. Accordingly, a sense of perspective can be suitably maintained, and a stable endoscopic image can be obtained.

Meanwhile, in a case where the operator greatly moves the treatment tool insertion part 202 forward with his/her hand that is gripping the operating part 204 of the treatment tool 200 in the state illustrated in FIG. 10, a state where the treatment tool fixing tool 450 has reached the front end (front restriction end 410) of the movable range thereof with respect to the coupling ring 402 as illustrated in FIG. 11A is brought about after the forward movement of the treatment tool fixing tool 450 of the slider 400 in the non-sensing region until it abuts against the front end (front restriction end 410) of the movable range. Then, in a case where the treatment tool insertion part 202 further moves forward, the treatment tool fixing tool 450 and the coupling ring 402 move forward with respect to the overtube long tubular part 320 together with the treatment tool insertion part 202. Then, the endoscope fixing tool 430 moves forward together with the coupling ring 402, and the endoscope insertion part 102 moves forward together with the endoscope fixing tool 430. Hence, the endoscope insertion part 102 moves forward in an interlocking manner with the treatment tool insertion part 202.

For that reason, with respect to the forward movement of the treatment tool insertion part 202 after the treatment tool fixing tool 450 has reached the front end (front restriction end 410) of the movable range thereof with respect to the coupling ring 402, the endoscope insertion part 102 moves forward in an interlocking manner with the treatment tool insertion part 202 as illustrated in (B) of FIG. 13, from the state of (A) of FIG. 13 which illustrated the same state as (A) of FIG. 12. That is, the slider 400 has the sensing region where the endoscope insertion part 102 is interlocked with the forward and backward movement of the treatment tool insertion part 202, and the forward movement operation of the treatment tool 200 at this time becomes the forward movement operation of the slider 400 in the sensing region.

Similarly, in a case where the operator greatly moves the treatment tool insertion part 202 backward with his/her hand that is gripping the operating part 204 of the treatment tool 200 in the state illustrated in FIG. 10, a state where the treatment tool fixing tool 450 has reached the rear end (rear restriction end 408) of the movable range thereof with respect to the coupling ring 402 as illustrated in FIG. 11B is brought about after the backward movement of the treatment tool fixing tool 450 of the slider 400 in the non-sensing region until it abuts against the rear end (rear restriction end 408) of the movable range. Then, in a case where the treatment tool insertion part 202 further moves backward, the treatment tool fixing tool 450 and the coupling ring 402 move backward with respect to the overtube long tubular part 320 together with the treatment tool insertion part 202. Then, the endoscope fixing tool 430 moves backward together with the coupling ring 402, and the endoscope insertion part 102 moves backward together with the endoscope fixing tool 430. Hence, the endoscope insertion part 102 moves backward in an interlocking manner with the treatment tool insertion part 202.

For that reason, with respect to the backward movement of the treatment tool insertion part 202 after the treatment tool fixing tool 450 has reached the rear end (rear restriction end 408) of the movable range thereof with respect to the coupling ring 402, as illustrated in (C) of FIG. 13, the endoscope insertion part 102 moves backward in an interlocking manner with the treatment tool insertion part 202.

That is, the backward movement operation of the treatment tool 200 of this time becomes the backward movement operation of the slider 400 in the sensing region.

Hence, since the endoscope 100 moves forward and backward with respect to large forward and backward movement operation of the treatment tool 200, that is, the forward and backward movement operation thereof in the sensing region, the range of an observation site that appears in an endoscopic image displayed on the monitor 112 is continuously changed so as to follow the forward and backward movement of the treatment tool 200. Accordingly, since the sizes of images of observation sites other than the distal end site of the treatment tool 200 that appears in the endoscopic image and the size of the range of the observation site vary according to the operation of the treatment tool 200, an operator can simply obtain a desired image.

Although the endoscope insertion axis 306a, which is the central axis of the endoscope insertion passage 306, and the treatment tool insertion axis 308a, which is the central axis of the treatment tool insertion passage 308, are parallel to the longitudinal axis 300a and the endoscope insertion axis 306a and the treatment tool insertion axis 308a are parallel to each other in the embodiment, the endoscope insertion axis and the treatment tool insertion axis may not necessarily be parallel to each other.

For example, a form in which the treatment tool insertion passage 308 is disposed to be parallel to the longitudinal axis 300a as in the embodiment and the endoscope insertion passage 306 is disposed to obliquely intersect the longitudinal axis 300a may be adopted. An overtube of this form will be specifically described as a modification example of the overtube 300 of the embodiment. In an embodiment to be described below as the modification example, configuration elements which have the same or similar working to the configuration elements of the embodiment will be assigned with the same reference signs.

Figure 14:
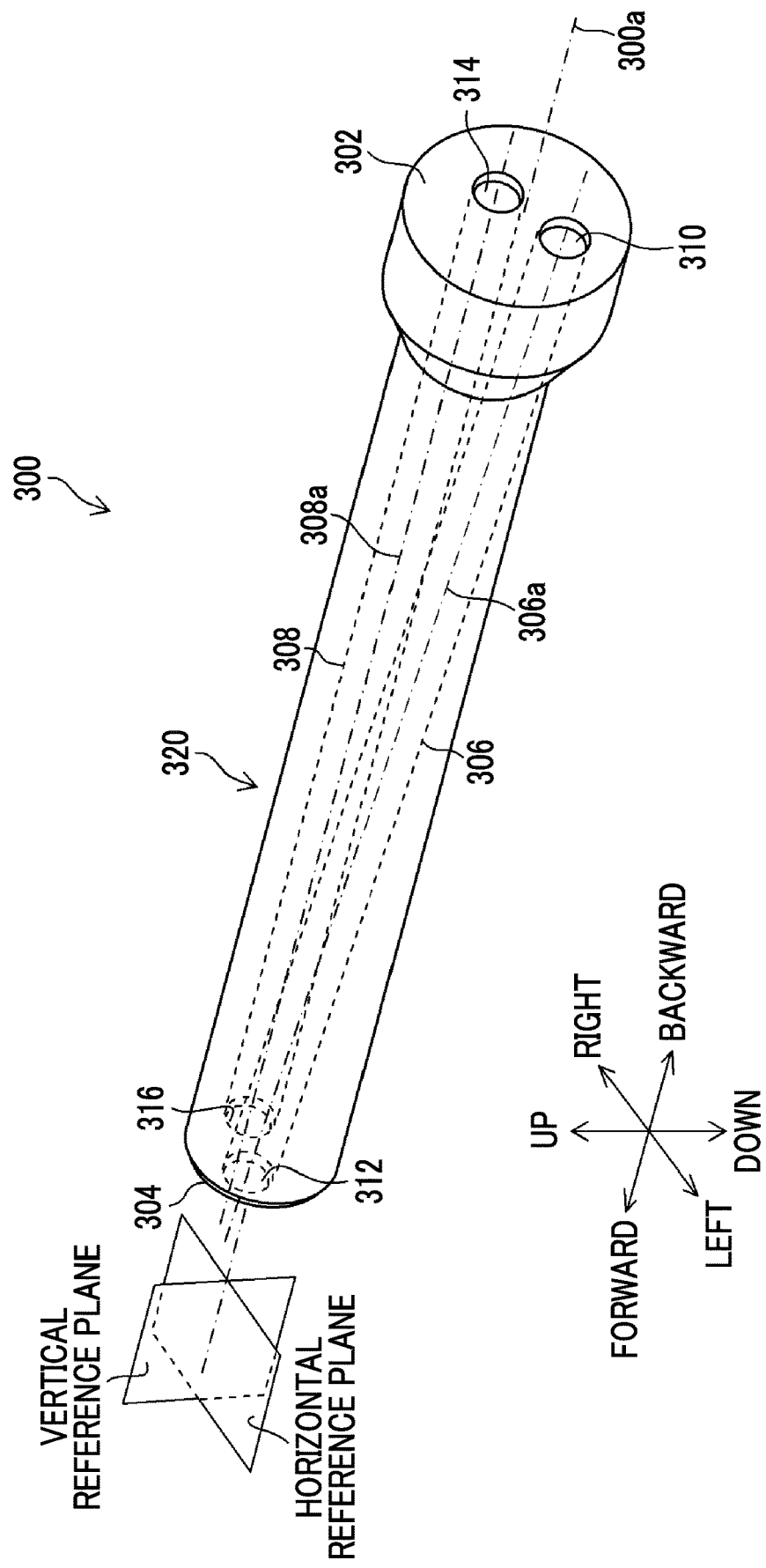
FIG. 14 is an external perspective view according to another embodiment of the overtube.

FIG. 14 is an external perspective view of the overtube 300 of the modification example.

In FIG. 14, the treatment tool insertion axis 308a of the treatment tool insertion passage 308 is disposed to be parallel to the longitudinal axis 300a of the overtube 300, and the endoscope insertion axis 306a of the endoscope insertion passage 306 is disposed to obliquely intersect the longitudinal axis 300a of the overtube 300. That is, in a case where a plane along an upward-downward direction including the longitudinal axis 300a is referred to as a vertical reference plane and a plane along the leftward-rightward direction including the longitudinal axis 300a is referred to as a horizontal reference plane, the treatment tool insertion axis 308a is parallel to both of the horizontal reference plane and the vertical reference plane.

On the other hand, the endoscope insertion axis 306a is parallel to the vertical reference plane, is not parallel to the horizontal reference plane, and is obliquely inclined with respect to the horizontal reference plane. In addition, the endoscope insertion axis 306a is inclined from a rear lower side toward a front upper side, and for example, intersects the horizontal reference plane at a substantially intermediate position of the overtube 300 in a forward-backward direction.

Figure 15:
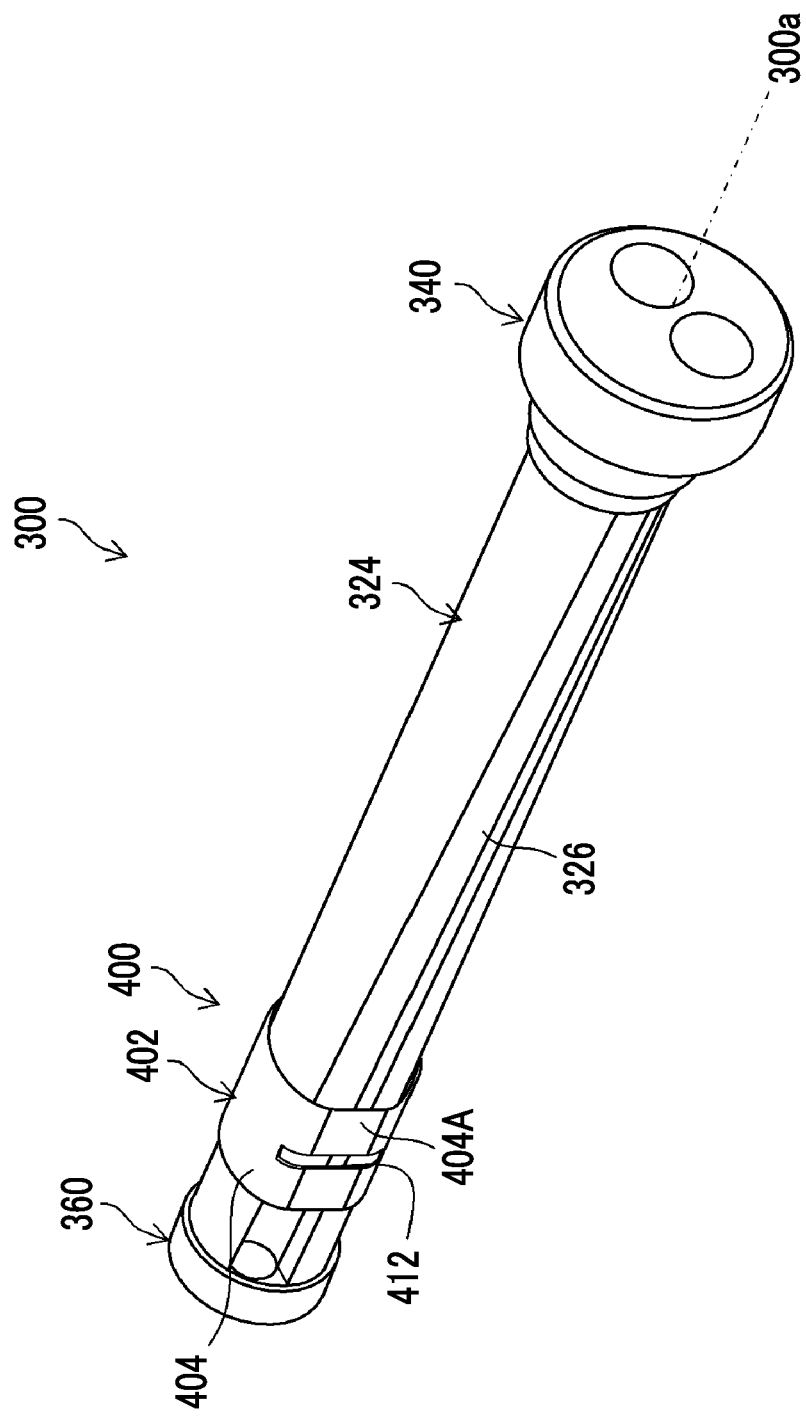
FIG. 15 is a perspective view illustrating the overtube of FIG. 14 with the long tubular body of the overtube long tubular part omitted.
Figure 16:
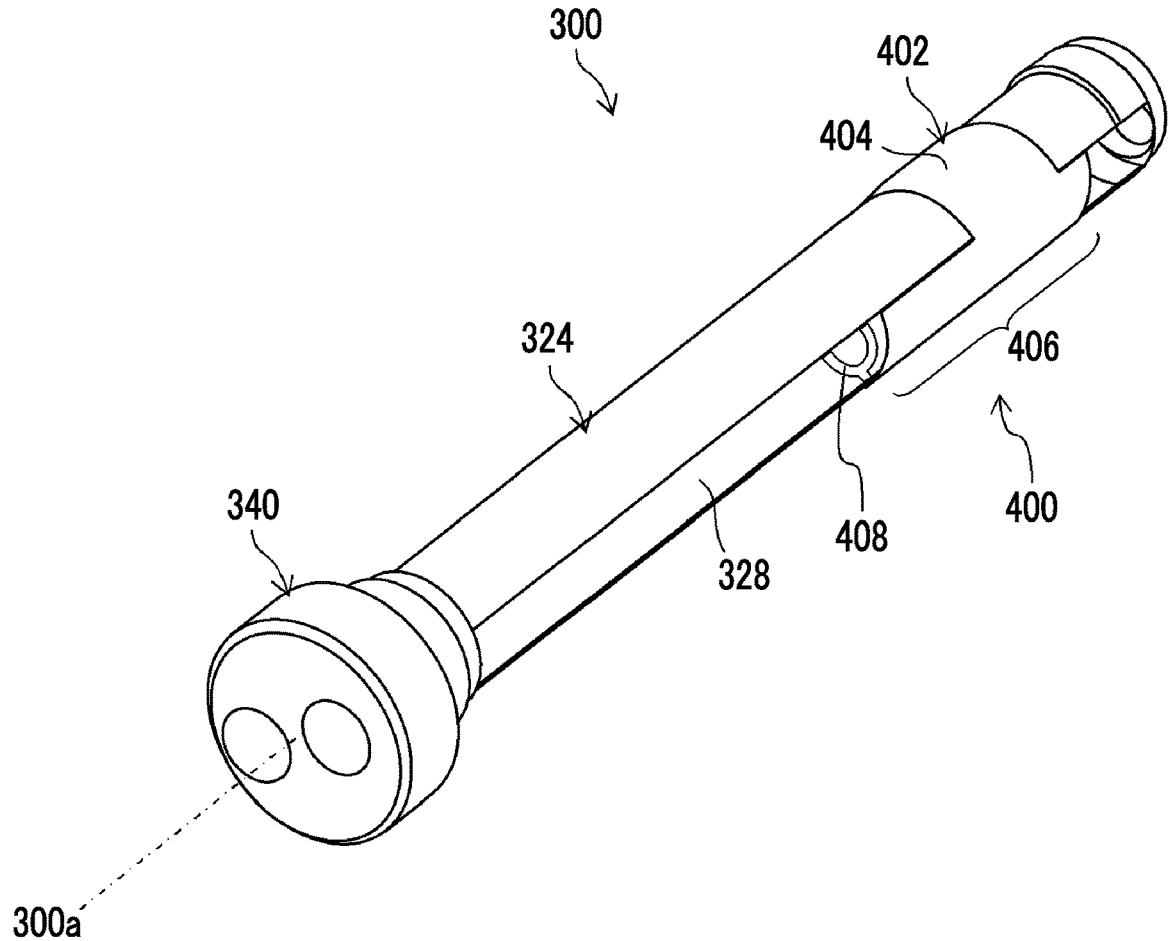
FIG. 16 is a perspective view illustrating the overtube of FIG. 14 with the long tubular body of the overtube long tubular part omitted.

The overtube 300 illustrated in FIG. 14 has the overtube long tubular part 320, the partition wall member 324 illustrated in FIGS. 15 and 16, and the slider 400 illustrated in FIGS. 15 and 16.

FIGS. 15 and 16 are perspective views illustrating the partition wall member 324 and the slider 400 of the overtube long tubular part 320 in a case of configuring the overtube 300 of FIG. 14. As illustrated in FIG. 16, the treatment tool guide groove 328 of the partition wall member 324 is formed along the treatment tool insertion axis 308a parallel to the longitudinal axis 300a as in the embodiment.

On the contrary, the endoscope guide groove 326 of the partition wall member 324 illustrated in FIG. 15 is formed along the endoscope insertion axis 306a which is not parallel to the longitudinal axis 300a and is oblique with respect to the horizontal reference plane.

In addition, since the endoscope fixing tool 430 (refer to FIG. 17) disposed inside the endoscope guide groove 326 moves forward and backward in the forward-backward direction, and moves also in the upward-downward direction with respect to the partition wall member 324 and the coupling ring 402, also the protrusion 436 formed on an outer peripheral part of the endoscope fixing tool 430 moves in the upward-downward direction with respect to the coupling ring 402 according to a position of the endoscope fixing tool 430 in the forward-backward direction.

Figure 17:
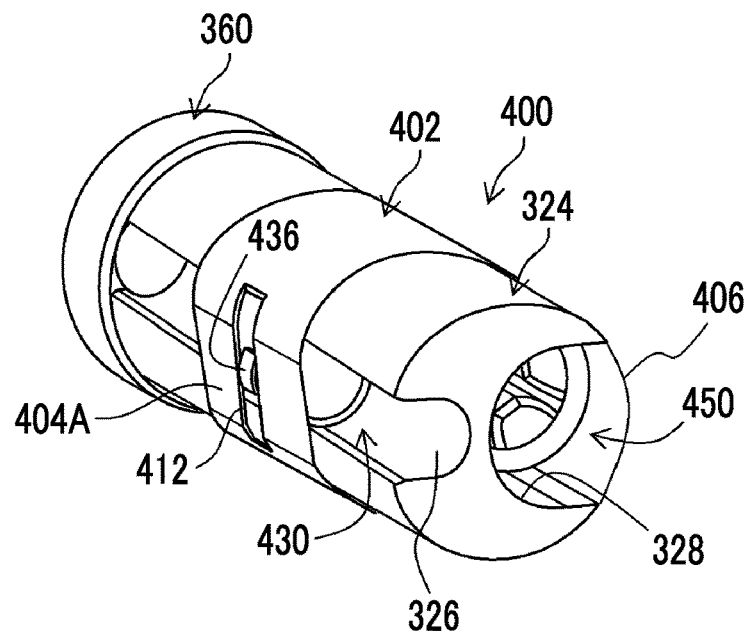
FIG. 17 is a perspective view illustrating a part of the overtube of FIG. 14.

Thus, the engagement hole 412 formed in the flat first engaging part 404A of the coupling ring 402 is formed as an elongated hole extending in the circumferential direction (upward-downward direction) beyond the range of the first engaging part 404A illustrated in the enlarged view of FIG. 17 so as to be engaged at any position in the movement range of the protrusion 436 in the upward-downward direction.

In addition, since the first engaging part 404A of the coupling ring 402 is a flat surface orthogonal to the leftward-rightward direction, a distance between an outer peripheral surface of the endoscope fixing tool 430 and the first engaging part 404A is uniformly maintained regardless of the movement of the endoscope fixing tool 430 in the upward-downward direction with respect to the coupling ring 402. For that reason, the amount of protrusion of the protrusion 436 can be reduced, and the diameter of the overtube long tubular part 320 can be reduced.

In a case where the endoscope guide groove 326 is obliquely formed, the opening of the endoscope guide groove 326 deviates from a position facing the first engaging part 404A. Thus, a range of the partition wall member 324 through which the first engaging part 404A passes due to the movement of the coupling ring 402 in the forward-backward direction is cut out along the flat surface so as not to interfere with the first engaging part 404A.

In such an overtube 300, the distal end of the endoscope insertion part 102 and a distal end of the treatment tool insertion part 202, which are inserted in the overtube 300, can be spaced apart from each other even in a case where an interval between the endoscope insertion passage 306 and the treatment tool insertion passage 308 in the overtube 300 is narrowed for diameter reduction. Thus, there is an advantage that it is easy to observe a state of a distal end (treatment part 206) of the treatment tool 200 with the endoscope 100.

Next, the endoscope 100 illustrated in FIG. 1 will be described.

Figure 18:
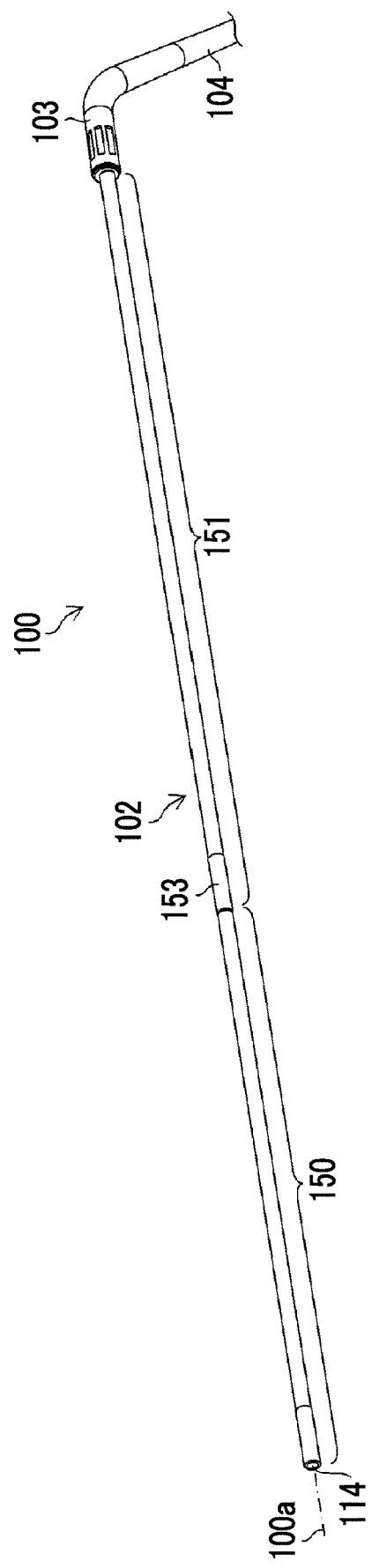
FIG. 18 is a perspective view of an endoscope.

FIG. 18 is an external perspective view of the endoscope insertion part 102 of the endoscope 100. The endoscope insertion part 102 comprises a first insertion part 150 and a second insertion part 151. The first insertion part 150 is provided on the distal end side of the endoscope insertion part 102, and has the observation part 114. The second insertion part 151 is provided on a proximal end side of the first insertion part 150 so as to be connected to the grip part 103, and has an outer diameter larger than the first insertion part 150. In addition, a held part 153 that is held by the endoscope fixing tool 430 (refer to FIG. 7) is provided in the second insertion part 151.

Figure 19:
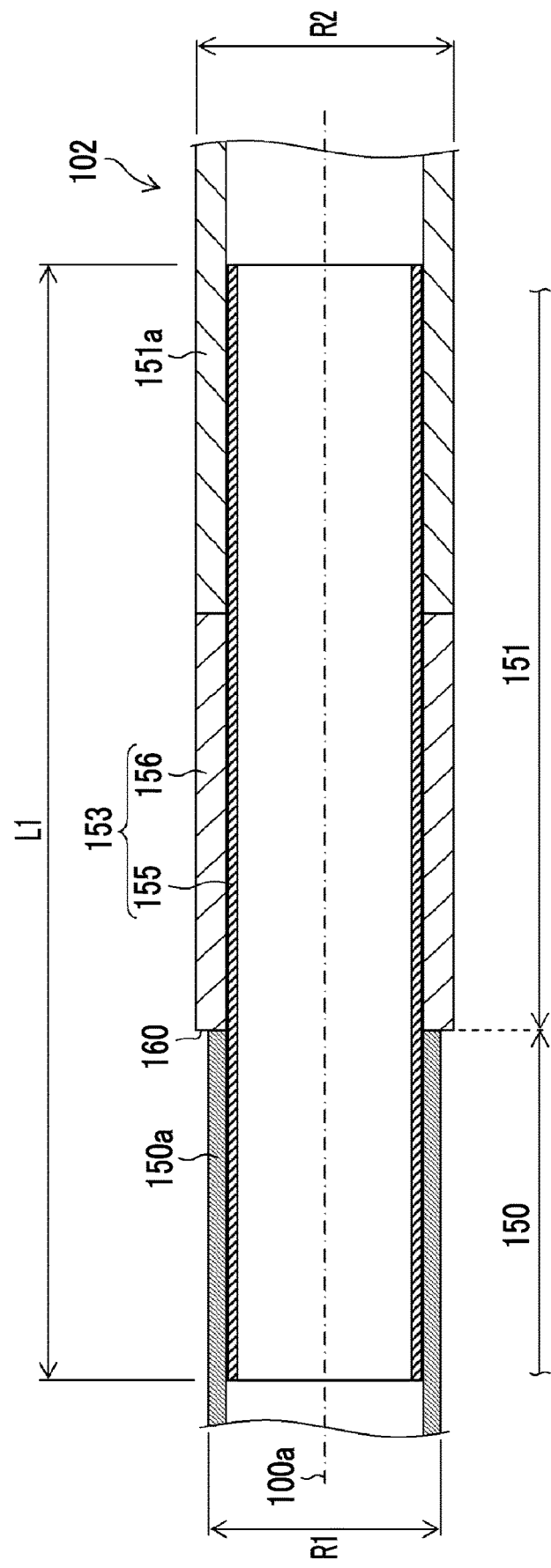
FIG. 19 is a cross-sectional view of a held part of the endoscope insertion part taken along an endoscope longitudinal axis.

FIG. 19 is a cross-sectional view of the held part 153 of the endoscope insertion part 102 taken along the endoscope longitudinal axis 100a. In order to prevent the drawing from becoming complicated, the illustration of the light guide 118 (refer to FIG. 1), the signal lines 126, and the like which are inserted in the endoscope insertion part 102 is omitted in FIG. 19. The light guide 118 and the signal lines 126 will be described below.

As illustrated in FIG. 19, the first insertion part 150 has a metal tubular body 150a extending in a direction parallel to the endoscope longitudinal axis 100a. The image pick-up lens group 120, the prism 122, and the solid image pickup element 124, which configure the observation part described above, are provided in the tubular body 150a, and the light guide 118 and the signal lines 126 are inserted in the tubular body. An outer diameter R1 of the first insertion part 150 is smaller than an inner diameter of the endoscope fixing tool 430 (refer to FIG. 7) by one size, that is, the first insertion part 150 is formed to have a size that rarely causes resistance in a case of being inserted into an inner periphery of the endoscope fixing tool 430.

The second insertion part 151 has a metal tubular body 151a, which extends in the direction parallel to the endoscope longitudinal axis 100a and allows the light guide 118 and the signal lines 126 to be inserted therein. The second insertion part 151 (including the held part 153) is formed to have an outer diameter R2 (R2>R1) having a size that matches the inner diameter of the endoscope fixing tool 430 (refer to FIG. 7), that is, a size that allows the second insertion part to be fitted to the inner periphery of the endoscope fixing tool 430. For example, the outer diameter R1 is 3.7 mm, and the outer diameter R2 is 3.8 mm.

The held part 153 has a metal tubular body 155 which extends in the direction parallel to the endoscope longitudinal axis 100a and allows the light guide 118 and the signal lines 126 to be inserted therein and an insulating pipe-like member 156 externally fitted onto an outer peripheral surface of a center part of the tubular body 155.

A distal end part of the tubular body 155 extends forward more than a distal end of the pipe-like member 156 does, and has a shape and an outer diameter which allow the distal end part of the tubular body 155 to be fitted to an inner periphery of the tubular body 150a of the first insertion part 150. In addition, a proximal end part of the tubular body 155 extends backward more than a proximal end of the pipe-like member 156 does, and has a shape and an outer diameter which allow the proximal end part of the tubular body 155 to be fitted to an inner periphery of the tubular body 151a of the second insertion part 151. For example, a length L1 in a direction of the endoscope longitudinal axis 100a of the tubular body 155 is 40 mm.

By the distal end part of the tubular body 155 being fitted to the inner periphery of the tubular body 150a and the proximal end part of the tubular body 155 being fitted to the inner periphery of the tubular body 151a, the second insertion part 151 is provided to be installed consecutively from the first insertion part 150 via the held part 153. In addition, the held part 153 is provided from a distal end toward a proximal end side of the second insertion part 151.

The pipe-like member 156 has the outer diameter R2 and an outer peripheral surface thereof is a held surface held by the endoscope fixing tool 430 (refer to FIG. 7). The pipe-like member 156 is formed of an insulating member such as an insulating resin and insulating ceramics. Since the outer diameter R2 of the pipe-like member 156 is larger than the outer diameter R1 of the first insertion part 150, a step part 160 is formed in a boundary between the first insertion part 150 and the held part 153 on the outer peripheral surface of the endoscope insertion part 102.

Figure 20:
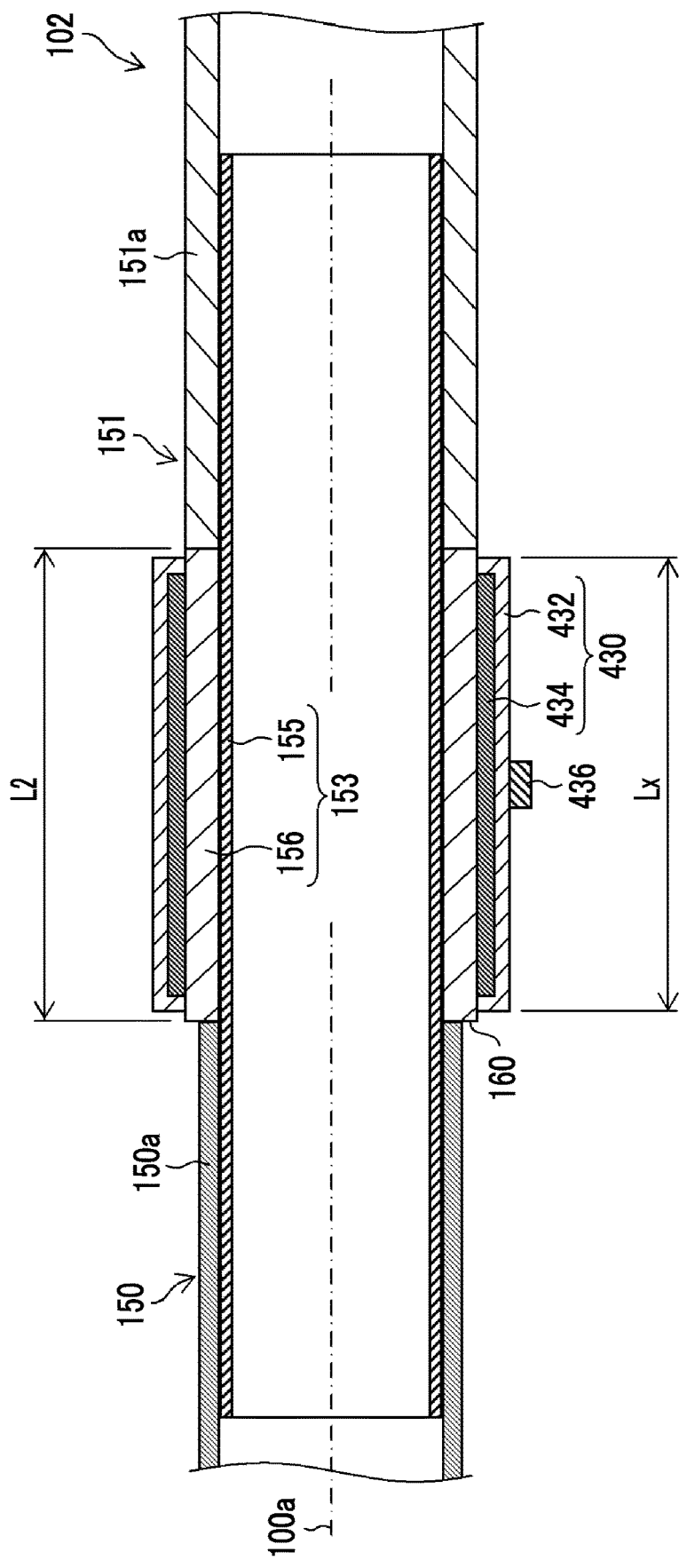
FIG. 20 is a cross-sectional view of an endoscope fixing tool and the held part, which is taken along the endoscope longitudinal axis.

FIG. 20 is a cross-sectional view of the endoscope fixing tool 430 and the held part 153, which is taken along the endoscope longitudinal axis 100a. In a case where a length of the endoscope fixing tool 430 in the direction of the endoscope longitudinal axis 100a is set as Lx, the pipe-like member 156 is formed to have a length L2 which is equal to or larger than at least the length Lx from the step part 160 to the proximal end side. The length L2 is, for example, 12 mm. Accordingly, the metal holding frame 432 of the endoscope fixing tool 430 is prevented from coming into contact with a part other than the pipe-like member 156 of the endoscope insertion part 102.

FIGS. 21A and 21B are explanatory views illustrating the holding of the endoscope insertion part 102 by the endoscope fixing tool 430 of the overtube 300. After the overtube 300 is inserted in the patient's body wall together with the outer sheath 500, the operator inserts the endoscope insertion part 102 into the endoscope insertion passage 306 from the first proximal end opening 310 (refer to FIG. 3) of the proximal end cap 340. After a distal end of the first insertion part 150 of the endoscope insertion part 102 proceeds along the endoscope insertion passage 306 and is inserted in the inner periphery of the endoscope fixing tool 430, the distal end protrudes from the first distal end opening 312 in the patient's body cavity.

In this case, since the outer diameter R1 (refer to FIG. 19) of the first insertion part 150 is smaller than the inner diameter of the endoscope fixing tool 430 by one size as illustrated in FIG. 21A, resistance rarely occurs even in a case where the first insertion part 150 is inserted in the inner periphery of the endoscope fixing tool 430. In a case where the operator continues insertion operation of the endoscope insertion part 102 into the endoscope insertion passage 306, the step part 160 formed by the held part 153 of the second insertion part 151 reaches an opening part in the inner periphery of the endoscope fixing tool 430 as illustrated in FIG. 21B. Since the outer diameter R2 (refer to FIG. 19) of the held part 153 is larger than the outer diameter R1, a resistance force against insertion operation occurs in a case where the step part 160 reaches the opening part in the inner periphery of the endoscope fixing tool 430. For this reason, the operator can determine that the step part 160 has reached the endoscope fixing tool 430 in the endoscope insertion passage 306 simply with the feeling in the hand performing insertion operation.

Next, in a case where the operator continues the insertion operation against the resistance force, the pipe-like member 156 of the held part 153 is fitted to the inner periphery of the endoscope fixing tool 430, and the held part 153 is held by the endoscope fixing tool 430 (refer to FIG. 20). By making the outer diameter R2 of the held part 153 larger than the outer diameter R1 of the first insertion part 150 as described above, the operator can simply have the endoscope fixing tool 430 hold the held part 153 of the endoscope insertion part 102 only with the feeling in the hand even in a case where the operator cannot see inside the overtube 300.

Figure 22:
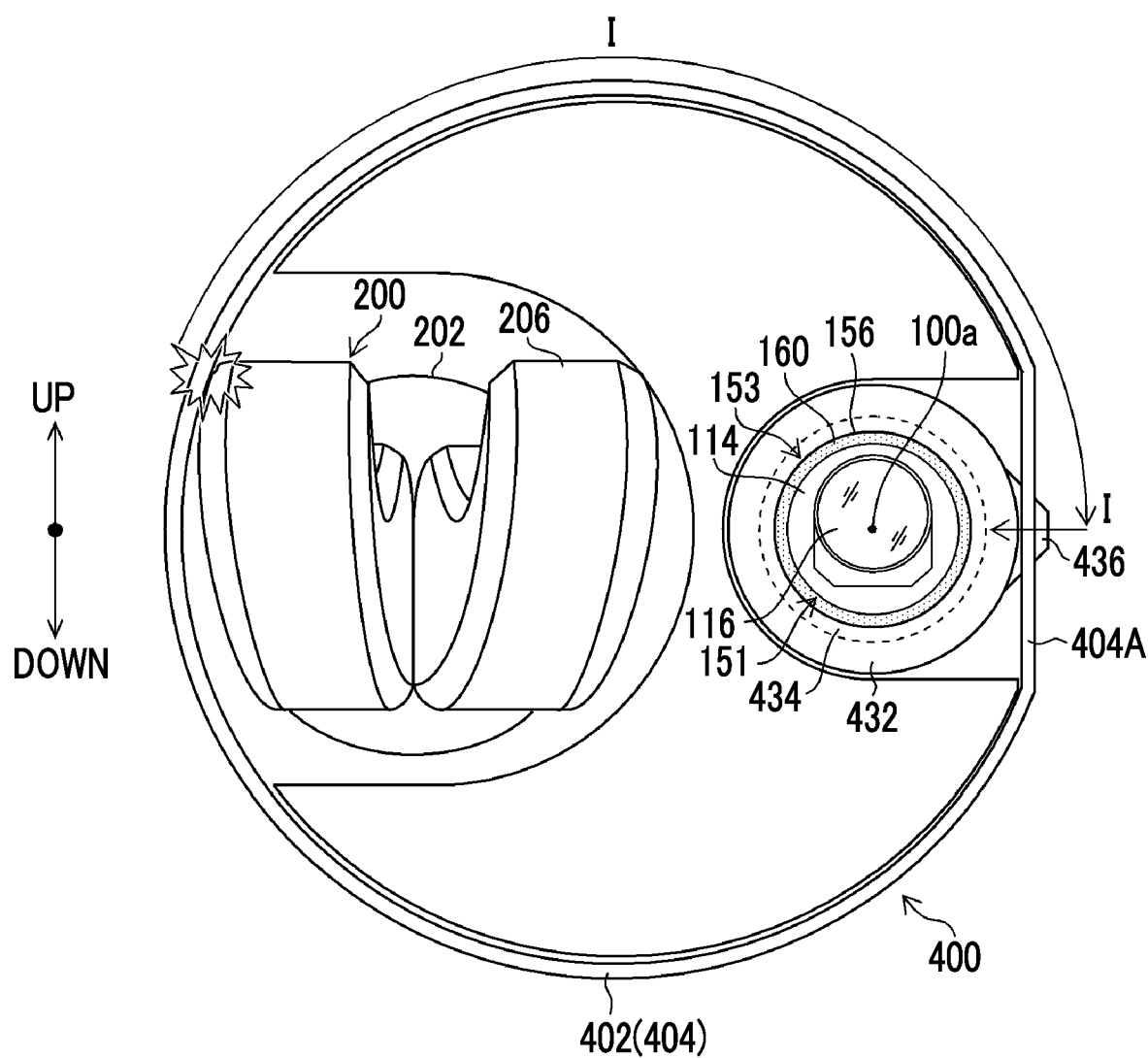
FIG. 22 is a cross-sectional view taken along line "22-22" in FIG. 7.

FIG. 22 is a cross-sectional view taken along line "22-22" in FIG. 7.

In a case of inserting the treatment tool 200 from the second proximal end opening 314 (refer to FIG. 3) along the treatment tool insertion passage 308 as illustrated in FIG. 22, or in a case of removing the treatment tool 200 from the treatment tool insertion passage 308, there is a possibility that the treatment part 206 that generates a high frequency current I comes into contact with the coupling ring 402 (ring part 404) of the slider 400.

In such a case, in a case where the operator mistakenly energizes the treatment tool 200, the high frequency current I generated from the treatment part 206 flows to the holding frame 432 through the coupling ring 402 (ring part 404), the first engaging part 404A, and the protrusion 436. In this case, since the pipe-like member 156 of the held part 153 of the endoscope 100, which is in contact with a part of the inner peripheral surface of the holding frame 432, has insulating properties, the high frequency current I is prevented from electrically leaking from the holding frame 432 to an endoscope 100 side through the held part 153.

Next, the signal lines 126 inserted into the endoscope insertion part 102 will be described.

Figure 23:
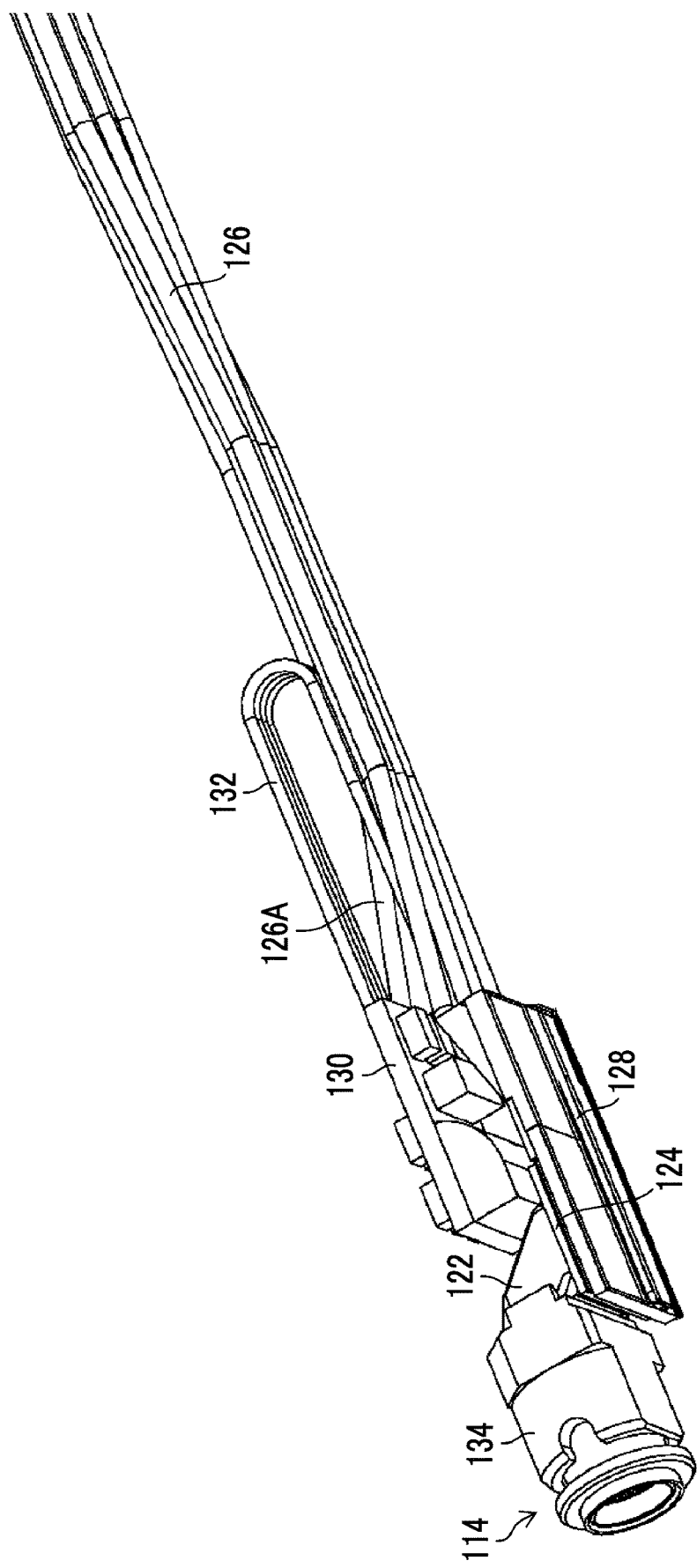
FIG. 23 is a perspective view illustrating a structure around a solid image pickup element disposed at an observation part of the endoscope insertion part.

FIG. 23 is a perspective view illustrating a structure around the solid image pickup element 124 disposed at the observation part 114 of the endoscope insertion part 102. In addition, FIG. 23 illustrates the plurality of signal lines 126 connected to the base substrate 128, on which the solid image pickup element 124 is mounted, and the processor device 108 of FIG. 1.

The signal lines 126 have a signal line that supplies power from the processor device 108 to the solid image pickup element 124 via the connector device 10, a signal line that outputs a control signal, and the like. In addition, the solid image pickup element 124 is mounted on the base substrate 128, and the base substrate 128 and a circuit substrate 130 of the solid image pickup element 124 are connected to each other by a flexible cable 132. A distal end part of an output signal line 126A, which is a part of the signal lines 126, is connected to the circuit substrate 130, and the output signal line 126A is inserted into the endoscope insertion part 102 so as to be connected to the connector device 10.

Figure 24:
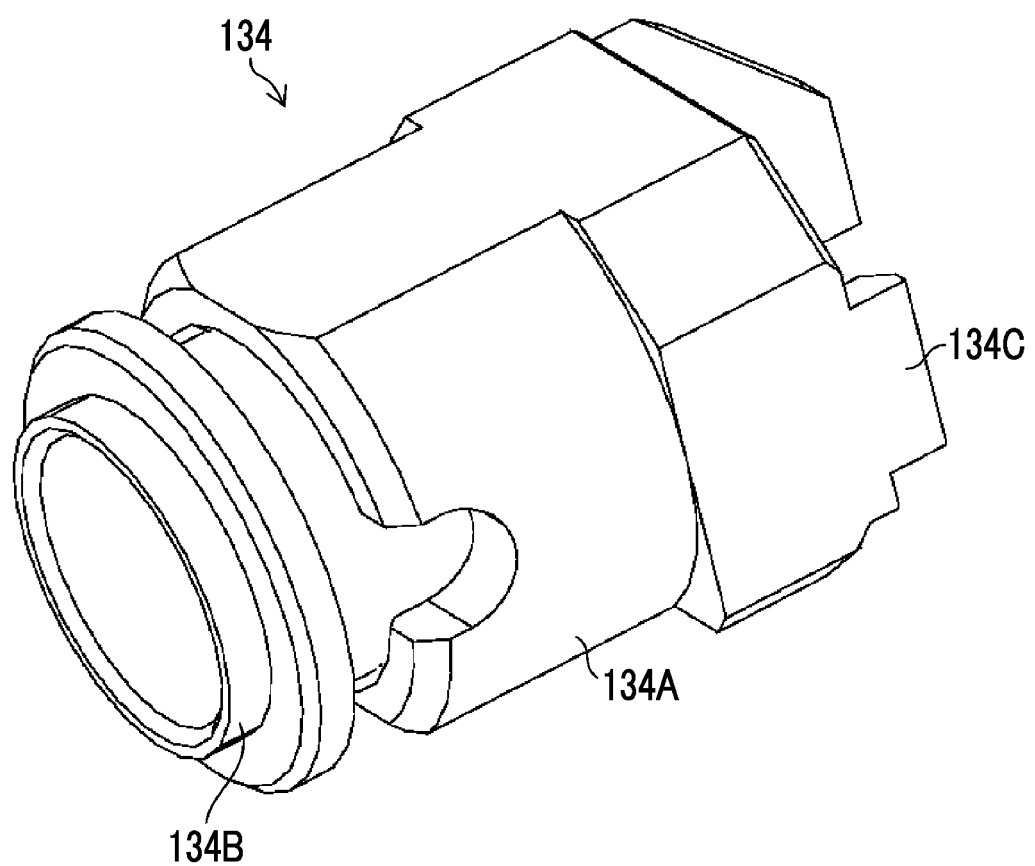
FIG. 24 is an enlarged perspective view of a lens barrel of image pick-up.

The image pick-up lens group 120 illustrated in FIG. 1 is held by a lens barrel 134 illustrated in FIGS. 23 and 24. FIG. 24 is an enlarged perspective view of the lens barrel 134.

The lens barrel 134 comprises a tubular body part 134A held by the image pick-up lens group 120, an annular holding part 134B that is formed at a distal end part of the body part 134A and holds the observation window 116, and a holding part 134C that is formed at a proximal end part of the body part 134A and holds the prism 122.

Figure 25:
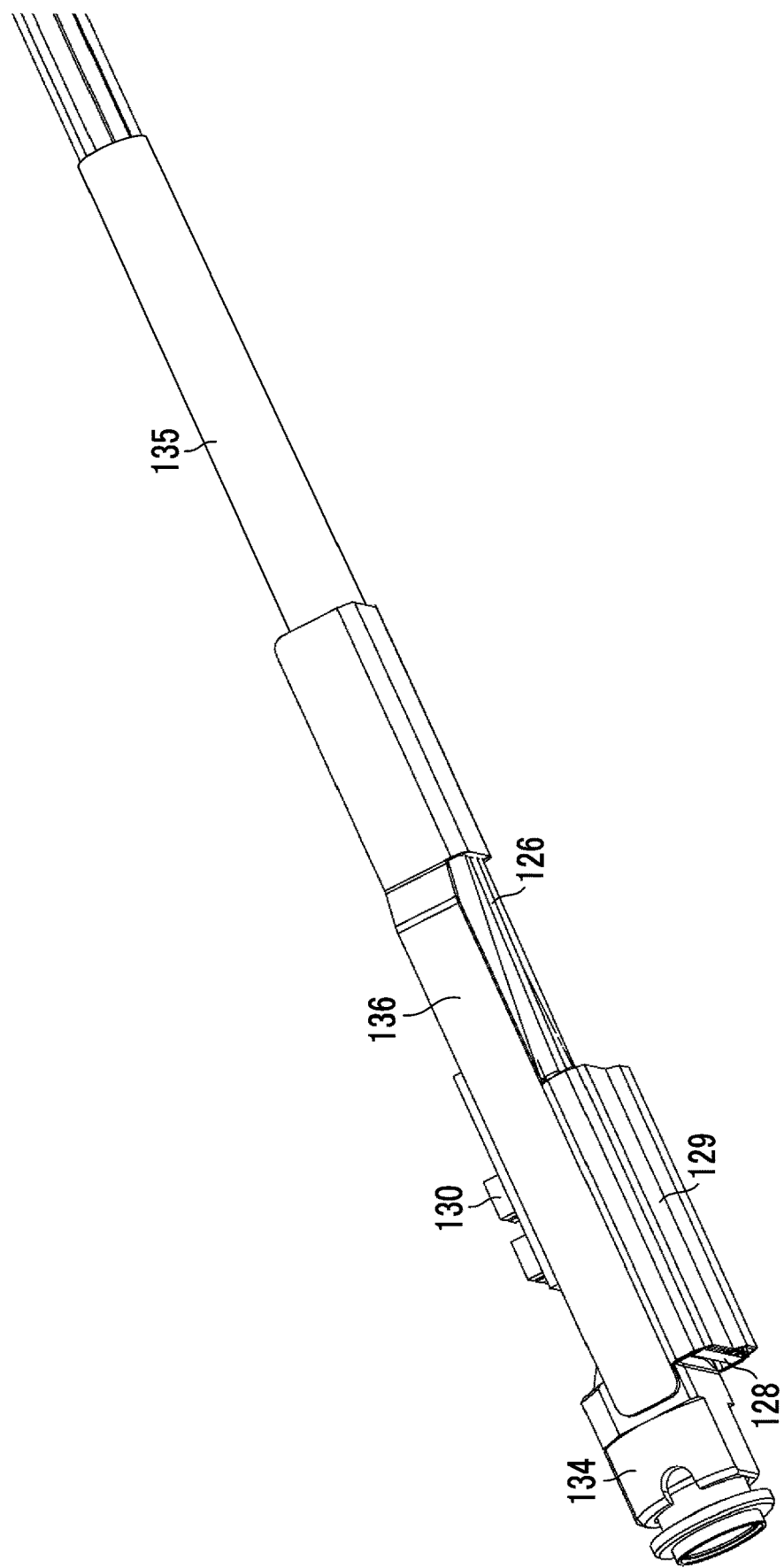
FIG. 25 is an explanatory view of a state where a bracket is mounted compared to FIG. 23.

Although the lens barrel 134, the base substrate 128, and the circuit substrate 130, which are configured in this manner, are integrally held by a bracket 136 illustrated in FIG. 25, the bracket 136 is not an indispensable member. In addition, FIG. 25 is an explanatory view of a state where the bracket 136 is mounted compared to FIG. 23. A distal end side of each of the signal lines 126 and the flexible cable 132, which are illustrated in FIG. 23, are covered with a silicon tube 135 illustrated in FIG. 25. In addition, the base substrate 128 is covered with a polyimide adhesive tape 129.

Figure 26:
FIG. 26 is an explanatory view illustrating a terminal part, which is a relay part for a signal line.

FIG. 26 is an explanatory view illustrating a terminal part 138, which is a relay part for the signal lines 126.

The distal end parts of the signal lines 126 extending from the connector device 10 of FIG. 1 are connected to a proximal end part of the terminal part 138, and the signal lines 126, which are connected to a distal end part of the terminal part 138, are connected to the solid image pickup element 124 via the base substrate 128 (refer to FIG. 23). In addition, a proximal end part of the output signal line 126A extending from the circuit substrate 130 of the solid image pickup element 124 is connected to the distal end part of the terminal part 138, and the distal end part of the output signal line connected to the proximal end part of the terminal part 138 is connected to the connector device 10. The terminal part 138 is disposed, for example, inside the held part 153 illustrated in FIG. 19.

Next, the light guide 118 inserted into the endoscope insertion part 102 will be described.

Figure 27:
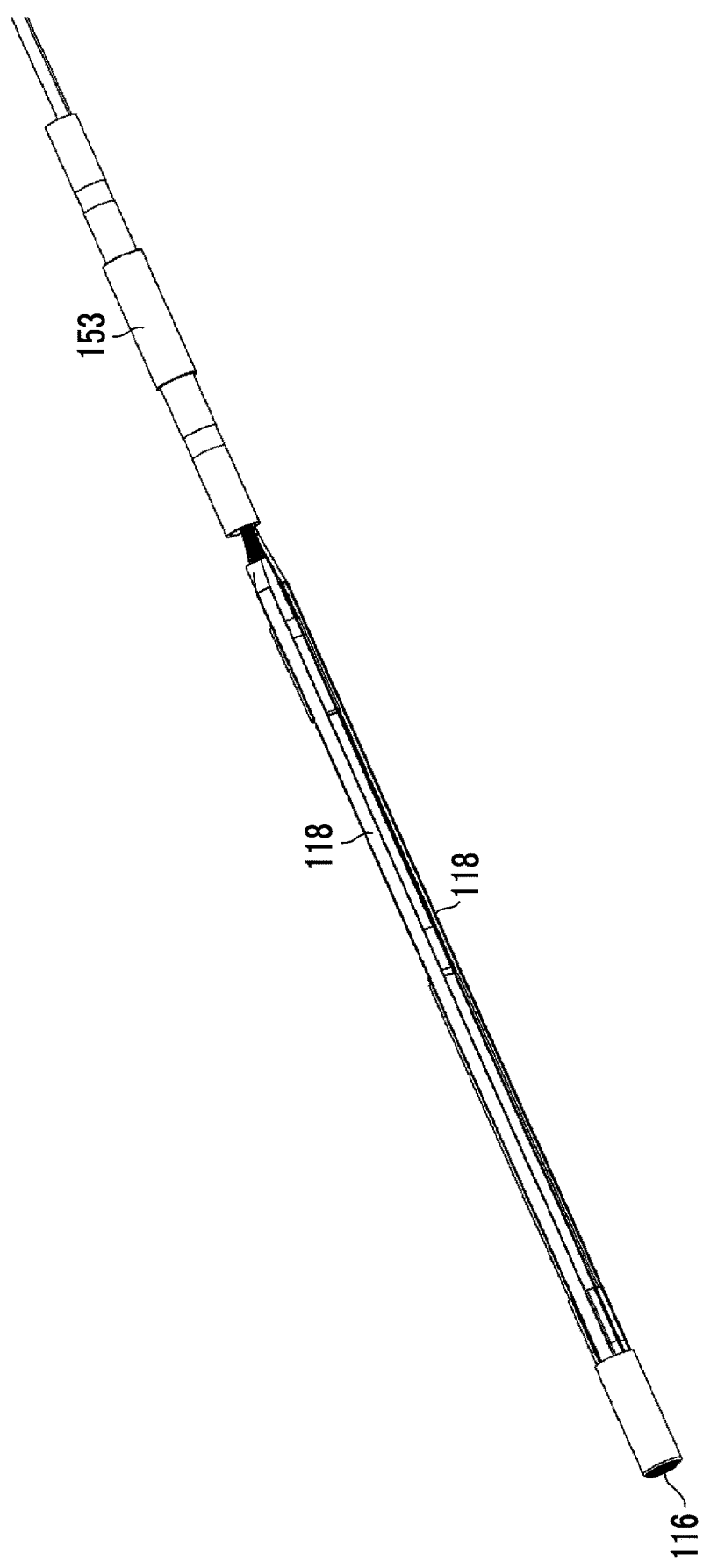
FIG. 27 is an explanatory view of a light guide which is inserted and disposed in a first insertion part of the endoscope insertion part.

FIG. 27 is an explanatory view illustrating an example of the light guide 118 which is inserted and disposed in the first insertion part 150 (refer to FIG. 18) of the endoscope insertion part 102. FIG. 27 is a perspective view of the first insertion part 150.

The light guide 118 inserted from the connector device 10 of FIG. 1 into the second insertion part 151 of the endoscope insertion part 102 is a bundle of light guides obtained by banding a plurality of optical fiber strands together. The light guide 118 is, for example, divided into three light guides 118 and extends to the observation part 114 of the endoscope insertion part 102, inside the held part 153 of FIG. 27. Accordingly, the emission ends 118A of the three light guides 118 are disposed in the vicinity of the observation window 116 as in FIG. 2.

Next, an airtight casing that airtightly holds between the observation part 114 disposed at the distal end of the endoscope insertion part 102 and the terminal part 138 will be described.

Figure 28:
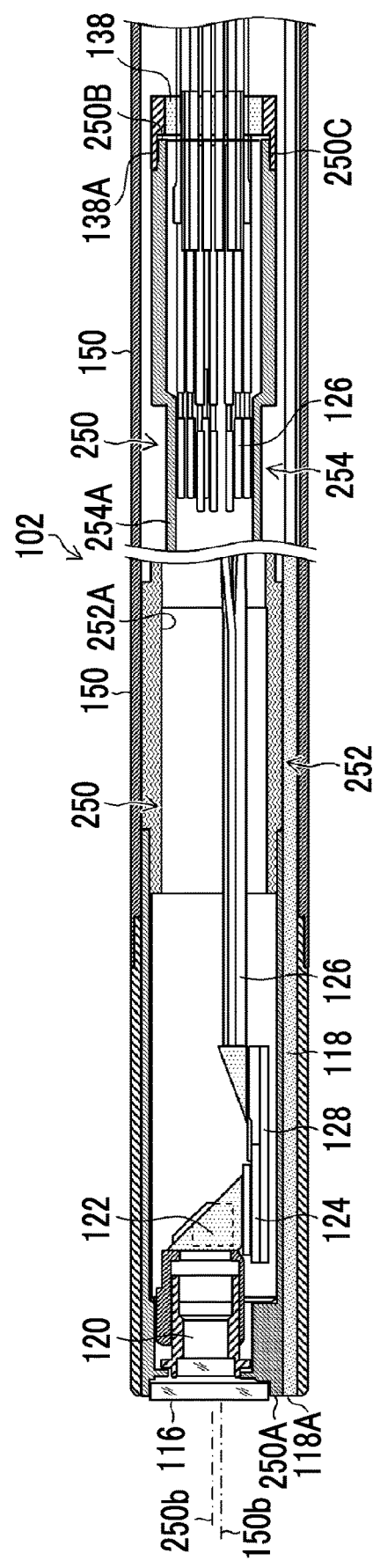
FIG. 28 is a cross-sectional view of important parts, in which a part of the endoscope insertion part is broken.
Figure 29:
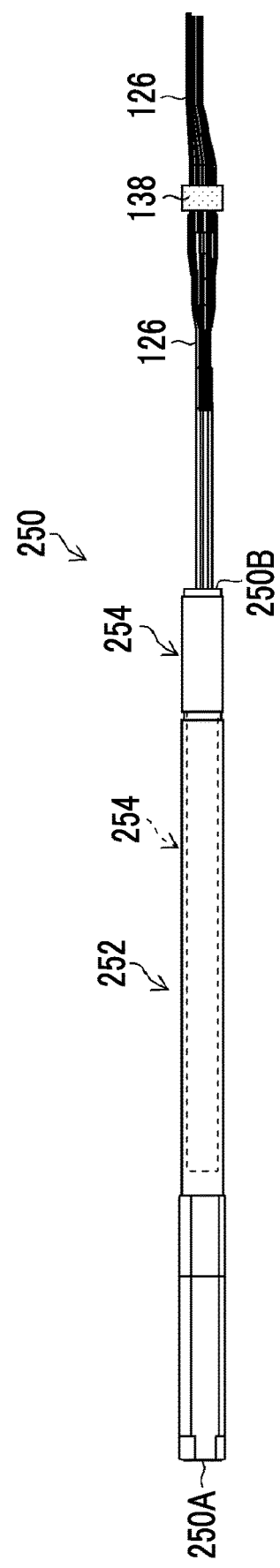
FIG. 29 is an assembly completion view of an airtight casing.

FIG. 28 is a cross-sectional view of important parts of the endoscope insertion part 102, and illustrates a cross section of an airtight casing 250 built in the endoscope insertion part 102. FIG. 29 is an assembly completion view of the airtight casing 250, and FIG. 30 is a view illustrating a form before assembly of the airtight casing 250.

As in FIG. 28, the airtight casing 250 is configured to be inserted and disposed inside the first insertion part 150 of the endoscope insertion part 102 and to have a length in the longitudinal axial direction which is shorter than the first insertion part 150. In addition, the airtight casing 250 is disposed such that a longitudinal axis 250b thereof is parallel to a longitudinal axis 150b of the first insertion part 150, and is disposed at a position eccentric to the longitudinal axis 150b.

Figure 30:
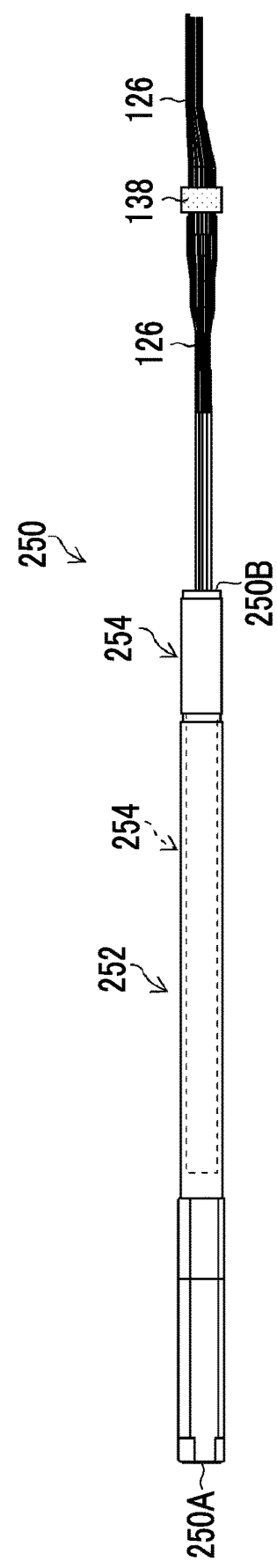
FIG. 30 is an explanatory view illustrating a form of the airtight casing before assembly.

As in FIGS. 29 and 30, the airtight casing 250 has a distal end 250A and a proximal end 250B. In addition, the airtight casing 250 has a tubular shape that is hollow inside, an opening of the distal end 250A is airtightly sealed with the disk-shaped observation window 116 of FIG. 28, and an opening of the proximal end 250B is airtightly sealed with the disk-shaped terminal part 138. Accordingly, an image pick-up lens group 120, the prism 122, the solid image pickup element 124, and the signal lines 126 are accommodated in an airtight state inside the airtight casing 250.

A sealing form, in which metal coating is executed in advance onto a side surface of the observation window 116 and the side surface and an inner peripheral surface of the distal end 250A are fixed to each other by soldering, can be given as an example of a sealing form of the observation window 116 with respect to the distal end 250A. In addition, a sealing form, in which a fitted part 138A included on a distal end side of the terminal part 138 and a fitting part 250C of the proximal end 250B are adhered to each other with an adhesive or welding as in FIG. 28, can be given as an example of a sealing form of the terminal part 138 with respect to the proximal end 250B.

As in FIG. 29, the airtight casing 250 is formed by a first tubular body 252 disposed on the distal end side and a second tubular body 254 disposed on the proximal end side.

An inner diameter D1 of a proximal end side of the first tubular body 252 is configured to be larger than an outer diameter D2 of a distal end side of the second tubular body 254. As in FIG. 28, an outer wall surface 254A of the second tubular body 254 is in sliding contact with an inner wall surface 252A of the first tubular body 252 in a state where airtightness is maintained. Although a state where the outer wall surface 254A is in sliding contact with the inner wall surface 252A is not illustrated in FIG. 28, the outer wall surface 254A is in sliding contact with the inner wall surface 252A on the proximal end side of the first tubular body 252 and the distal end side of the second tubular body 254.

In addition, the first tubular body 252 and the second tubular body 254 are slidably attached to each other so as to be movable forward and backward relatively to each other along the longitudinal axis 250b. Accordingly, as in FIG. 30, the airtight casing 250 before assembly is configured as a double tube structure formed by the first tubular body 252 and the second tubular body 254, and is configured as a telescopic structure that is stretchable in a direction of the longitudinal axis 250b.

When assembling the airtight casing 250, from a form of the double tube structure illustrated in FIG. 30, the second tubular body 254 is pulled out from the first tubular body 252, and a proximal end of the first tubular body 252 and a distal end of the second tubular body 254 are fixed to each other. Accordingly, the airtight casing 250 is assembled as in FIG. 29. A form of fixing the proximal end of the first tubular body 252 and the distal end of the second tubular body 254 may be soldering or may be welding.

Figure 31:
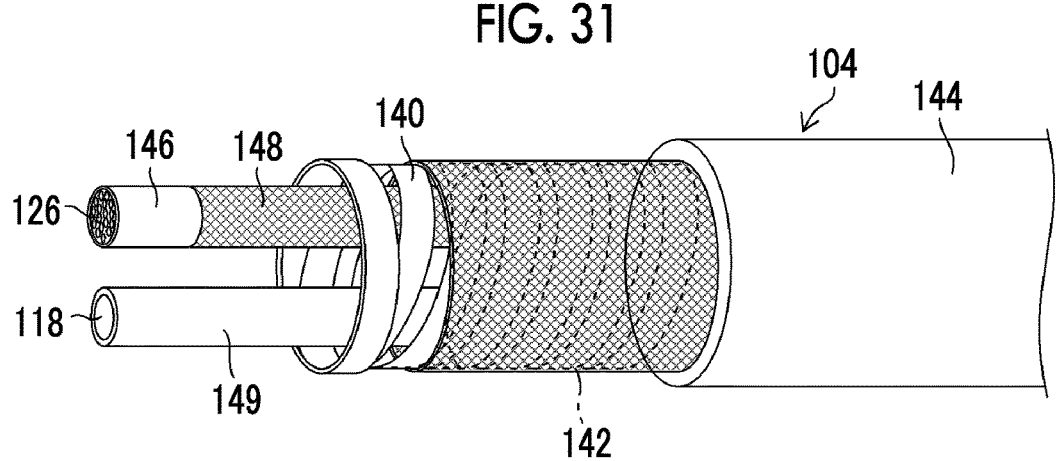
FIG. 31 is a broken view of a universal cable in which the signal line and the light guide are inserted.

The signal lines 126 and the light guide 118, which are described above, are inserted inside the universal cable 104 as in FIG. 31. FIG. 31 is a broken view of the universal cable 104 in which the signal lines 126 and the light guide 118 are inserted.

The universal cable 104 is configured, in order from the inside, by three layers including a spiral tube 140 that protects the signal lines 126 and the light guide 118 while maintaining flexibility, a tubular net 142 that covers an outer peripheral surface of the spiral tube 140, and a tubular skin 144 made of silicon rubber covering the net 142.

The plurality of signal lines 126 are banded with a flexible tube 146 inserted inside the spiral tube 140, and a tubular net 148 covers an outer peripheral surface of the tube 146. Similarly, also the light guide 118 formed with the plurality of optical fiber strands is banded by a flexible tube 149 inserted inside the spiral tube 140.

Figure 32:
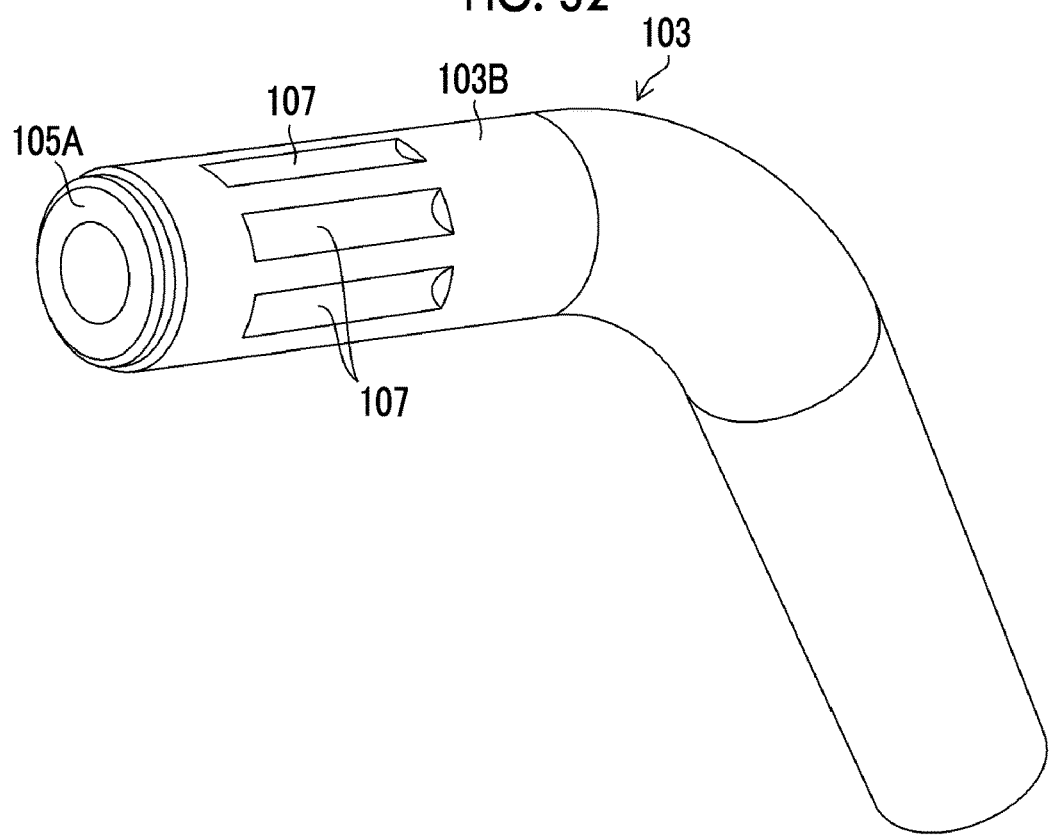
FIG. 32 is an enlarged perspective view of a grip part of the endoscope.
Figure 33:
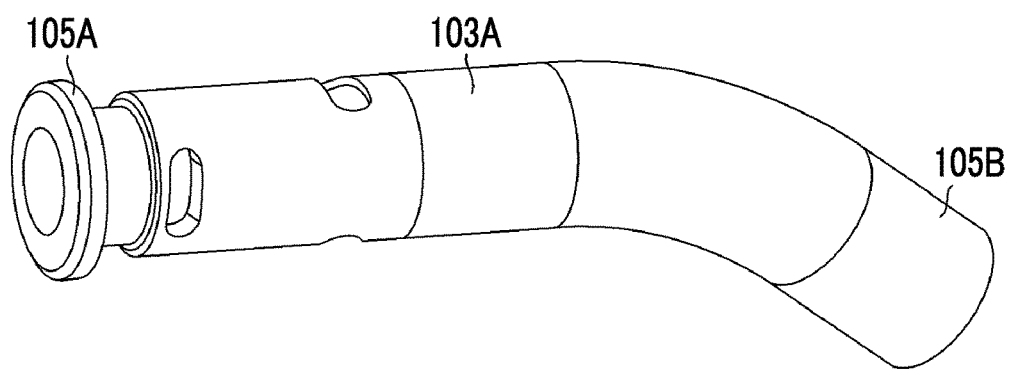
FIG. 33 is a perspective view of a metal body configuring the grip part.

Next, the grip part 103 of the endoscope 100 will be described. FIG. 32 is an enlarged perspective view of the grip part 103. FIG. 33 is a perspective view of a metal body 103A configuring the grip part 103.

The body 103A is configured in a curved tubular shape, an annular part 105A, which is a distal end part, is configured as a connecting part connected to the proximal end part of the endoscope insertion part 102, and a tubular part 105B, which is a proximal end part, is configured as a connecting part connected to the distal end part of the universal cable 104.

The body 103A is covered with a silicon rubber cover 103B illustrated in FIG. 32. Accordingly, the grip part 103 is configured. The cover 103B is formed in a straight rod shape as a single body. In addition, a plurality of grooves 107 that give the operator grip feeling are formed in an outer peripheral surface of a distal end part of the cover 103B along a longitudinal axis of the cover 103B.

Next, the connector device 10 according to the embodiment will be described.

Figure 34:
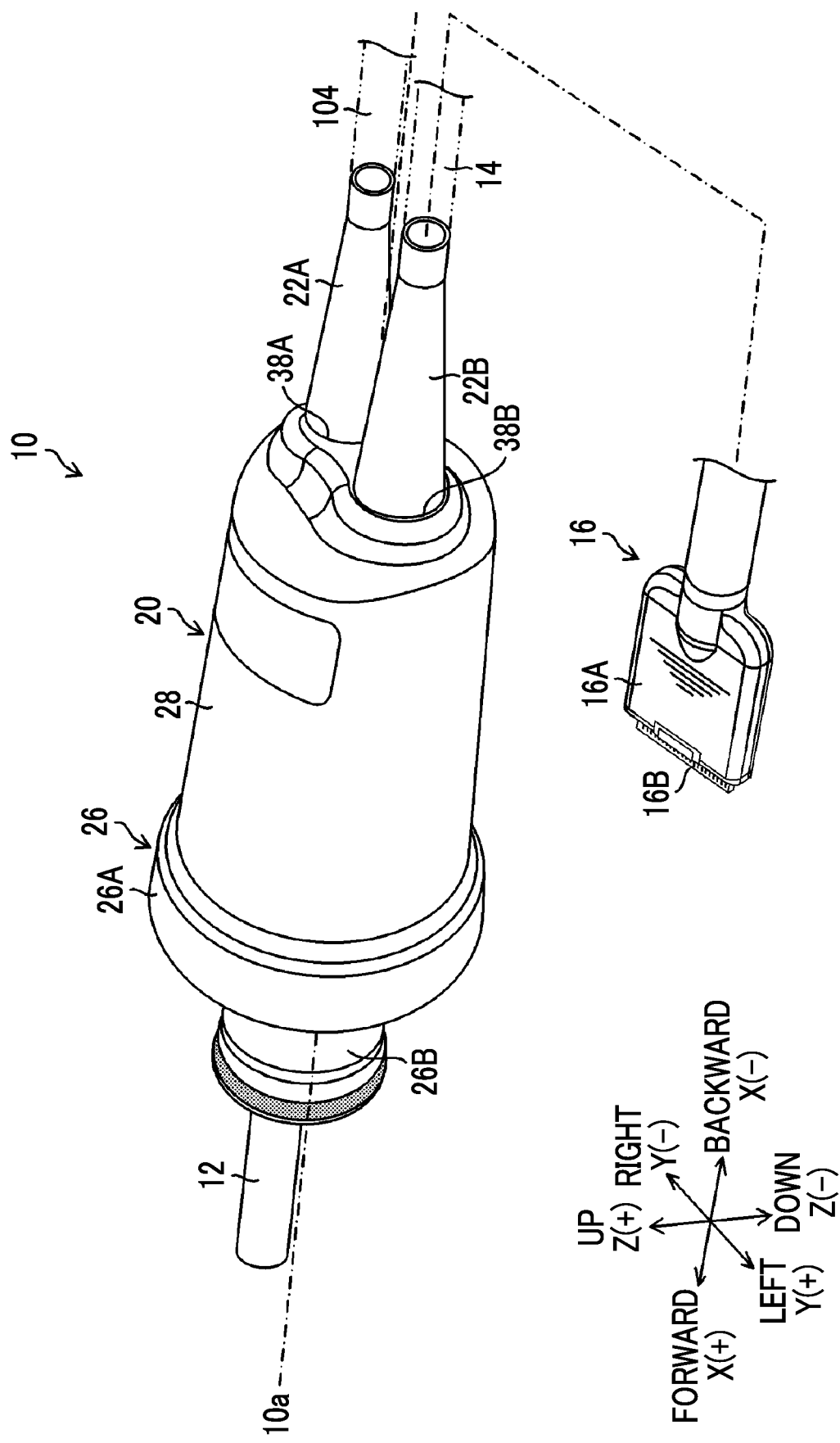
FIG. 34 is an external perspective view of a connector device.

FIG. 34 is an external perspective view of the connector device 10. The connector device 10 has a cylindrical shape as a whole, and has a longitudinal axis 10*a* which is parallel to an axial direction of the straight pipe-like light guide rod 12.

FIG. 34 illustrates the flat connector 16. The flat connector 16 is configured by a flat body part 16A having a proximal end part linked to the distal end part of the video cable 14 and a terminal board 16B protruding outwards from a distal end part of the body part 16A.

Figure 35:
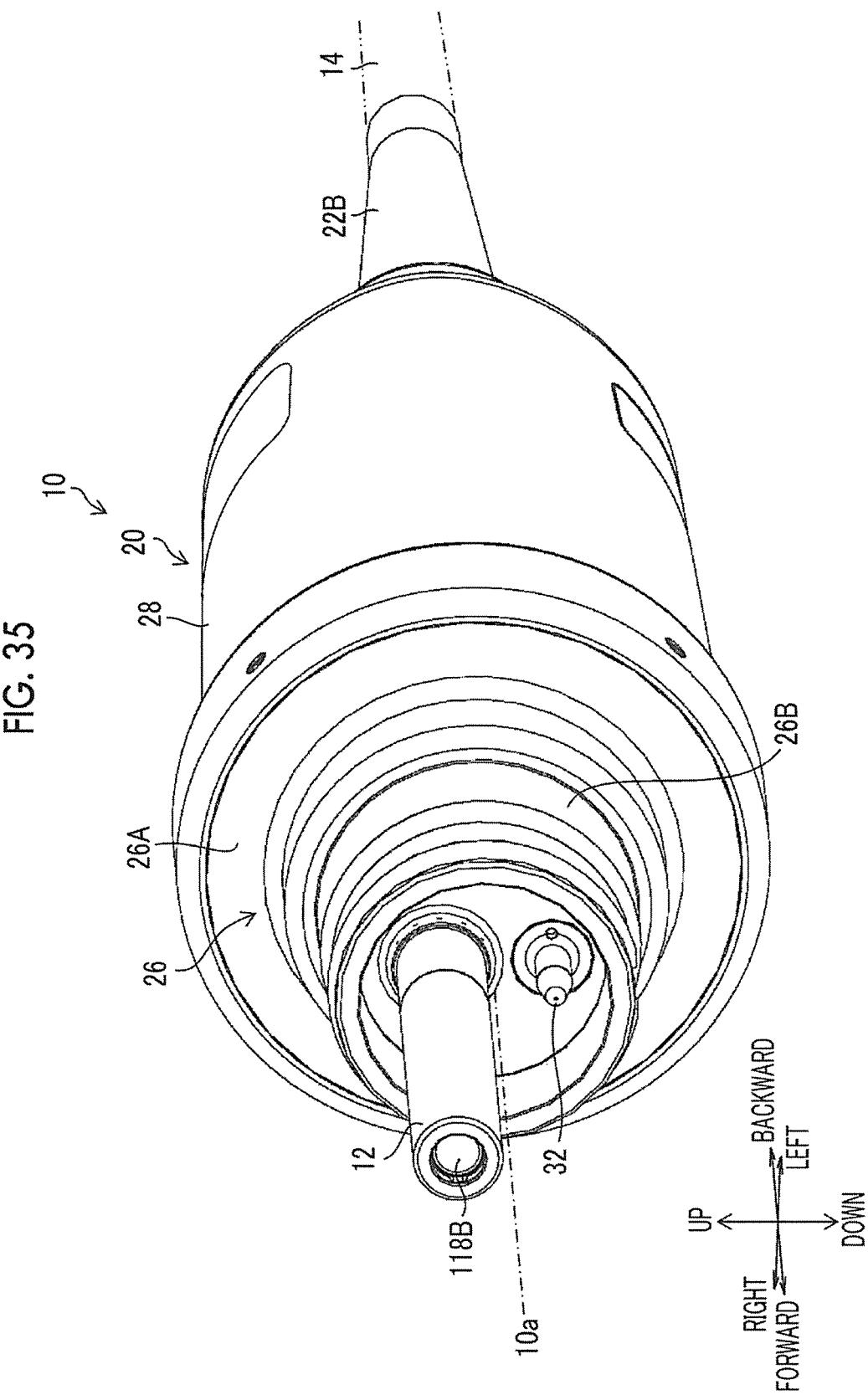
FIG. 35 is an external perspective view of the connector device seen from the front toward the rear.

Regarding the position and orientation of a space where the connector device 10 is disposed, the term "forward" is used for an orientation of an X(+) direction along the longitudinal axis 10*a*, the term "backward" is used for an orientation of an X(−) direction, the term "left" is used for an orientation of a Y(+) direction orthogonal to an X-direction, the term "right" is used for an orientation of a Y(−) direction, the term "up" is used for an orientation of a Z(+) direction orthogonal to the X-direction and a Y-direction, and the term "down" is used for an orientation of a Z(−) direction. FIG. 35 is an external perspective view of the connector device 10 seen from the front toward the rear.

In the external perspective views of FIGS. 34 and 35, the connector device 10 has a sheathing member 20 made of a resin having high heat resistance and chemical resistance, the metal light guide rod 12, and two covers 22A and 22B made of silicon rubber.

Figure 36:
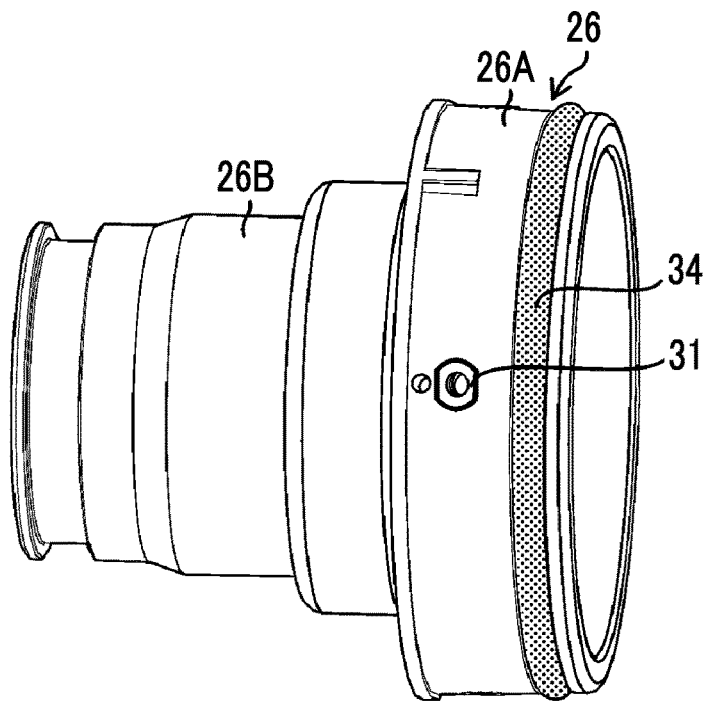
FIG. 36 is a perspective view of a plug configuring a sheathing member.
Figure 37:
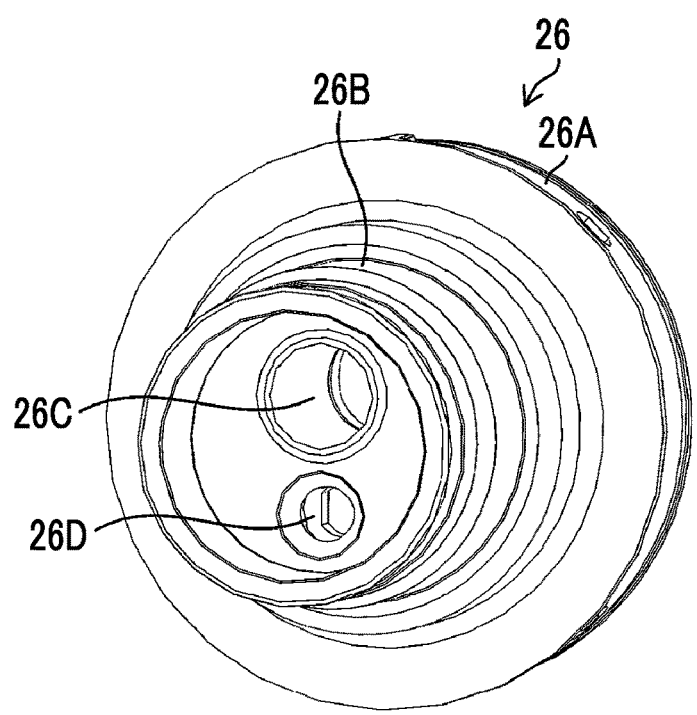
FIG. 37 is a perspective view of the plug seen from the front toward the rear.
Figure 38:
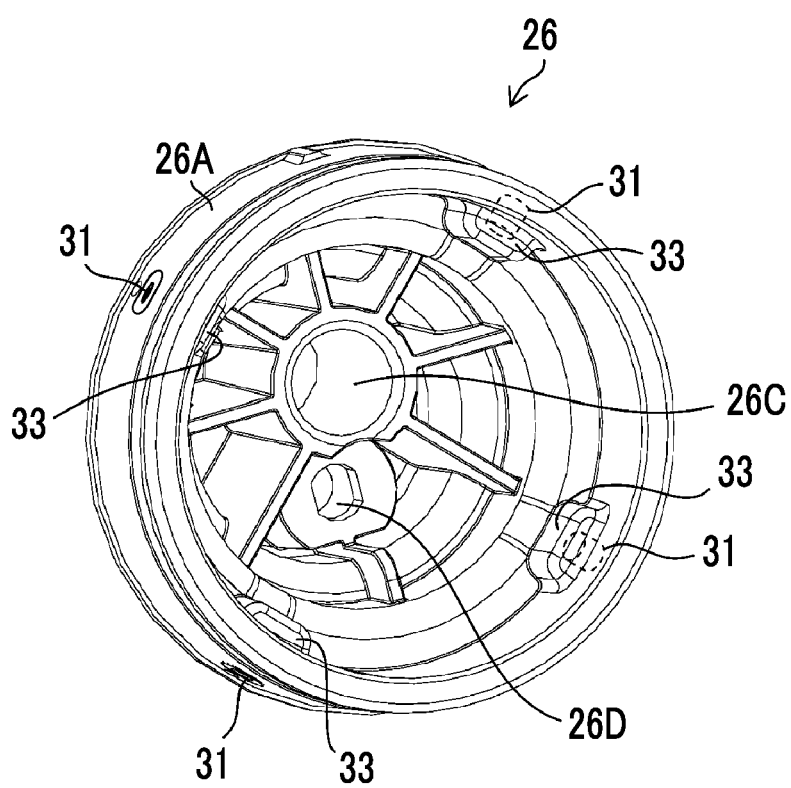
FIG. 38 is a perspective view of the plug seen from the rear toward the front.

FIG. 36 is a perspective view of a plug (stopper) 26 configuring the sheathing member 20. FIG. 37 is a perspective view of the plug 26 seen from the front toward the rear. FIG. 38 is a perspective view of the plug 26 seen from the rear toward the front.

Figure 39:
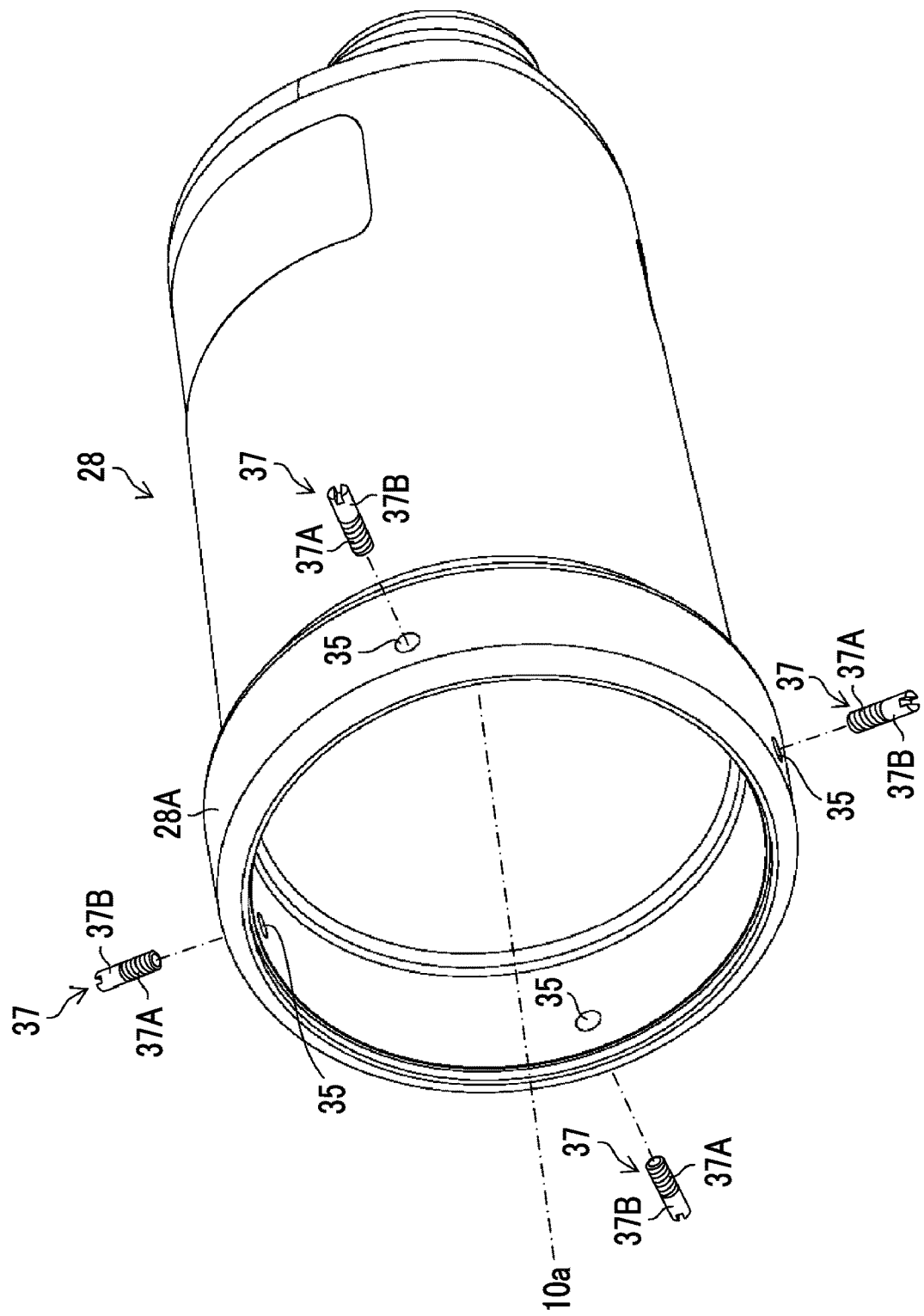
FIG. 39 is a perspective view of a connector sheathing case configuring the sheathing member seen from the front toward the rear.
Figure 40:
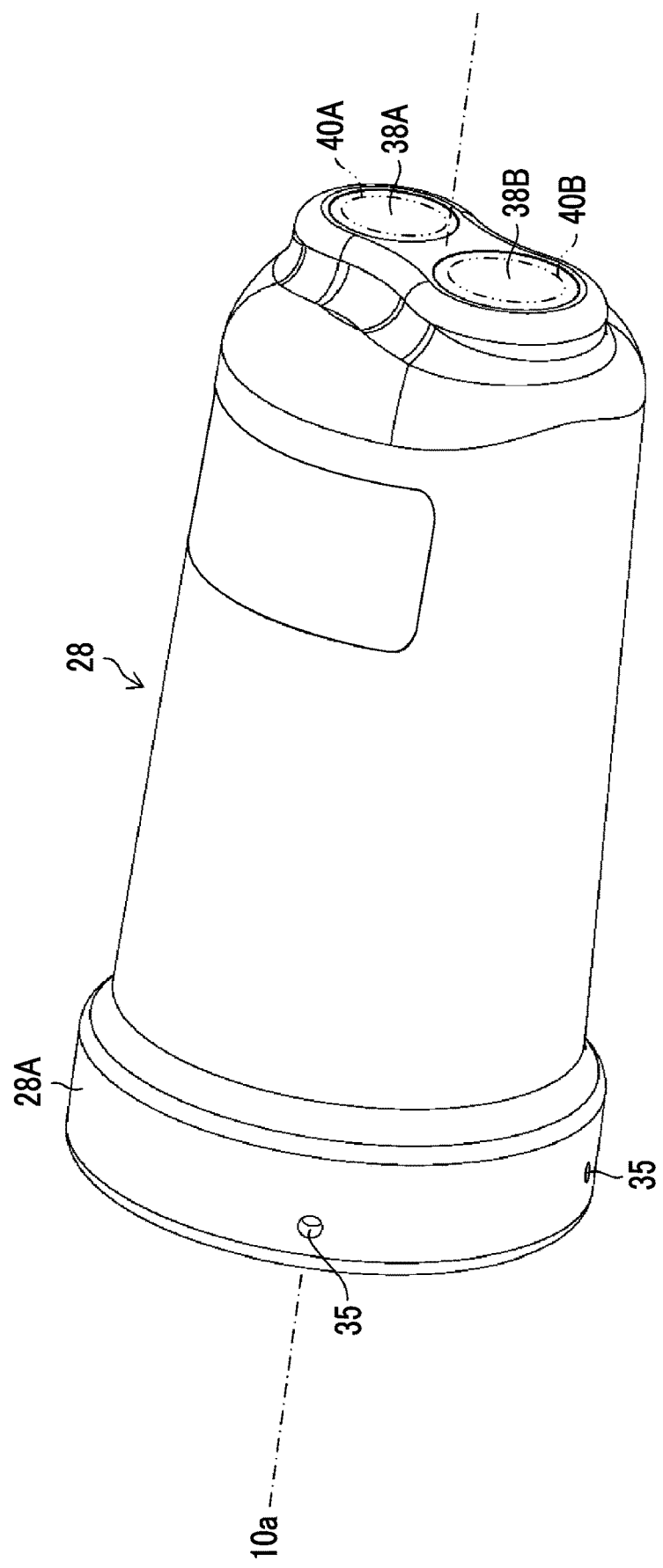
FIG. 40 is a perspective view of the connector sheathing case seen from the rear toward the front.

In addition, FIG. 39 is a perspective view of a connector sheathing case 28 configuring the sheathing member 20 seen from the front toward the rear. FIG. 40 is a perspective view of the connector sheathing case 28 seen from the rear toward the front.

Referring back to FIGS. 34 and 35, the sheathing member 20 illustrated in FIGS. 34 and 35 is configured by connecting the plug 26 illustrated from FIGS. 36 to 38 to the connector sheathing case 28 illustrated in FIGS. 39 and 40.

As illustrated in FIGS. 36 to 38, the plug 26 comprises an annular part 26A having a large diameter and a tubular part 26B that protrudes forward from the annular part 26A and has a small diameter.

As illustrated in FIG. 35, the plug 26 is a member that holds the light guide rod 12, which is an extension member, and comprises, inside the tubular part 26B, a leading-out hole 26C (refer to FIG. 37) that leads the light guide rod 12 to the outside. An incidence end 118B, which is the proximal end part of the light guide 118, is disposed at a front end of the light guide rod 12.

An elastic O-ring 30 (refer to FIG. 41) is fitted to an outer peripheral surface of the light guide rod 12, and the light guide rod 12 is fitted to the leading-out hole 26C via the O-ring 30. That is, the O-ring 30 is configured as a first sealing member that is provided on the light guide rod 12 and seals the inside of the sheathing member 20 by being placed in a gap between the light guide rod 12 and the leading-out hole 26C. In addition, the light guide rod 12 is held by the plug 26 via only the O-ring 30 without going through a member other than the O-ring 30.

A material for the plug 26 and the connector sheathing case 28, which configure the sheathing member 20, is for example, a polyphenylsulfone resin, a material for the light guide rod 12 is, for example, stainless steel, and a material for the O-ring 30 is, for example, fluoro rubber having high heat resistance. In addition, in the plug 26, a through hole 26D (refer to FIG. 37) is formed adjacent to the leading-out hole 26C. A positioning pin 32 (refer to FIG. 35) is mounted onto the through hole 26D via an O-ring (not illustrated). In a case of connecting the light guide rod 12 to the light source device 110 (refer to FIG. 1), the positioning pin 32 is a fitted to a recessed part (not illustrated) provided in the light source device 110. Accordingly, the light guide rod 12 is positioned and connected to the light source device 110.

As illustrated in FIGS. 39 and 40, the connector sheathing case 28 is configured in a cylindrical shape, and has the longitudinal axis 10*a*, which is an axis of the cylinder.

The annular part 26A of the plug 26 illustrated in FIG. 36 is fitted to an annular part 28A, which is a front end of the connector sheathing case 28. An O-ring 34 is provided on an outer peripheral surface of the annular part 26A. Accordingly, the plug 26 is connected to the connector sheathing case 28 via the O-ring 34.

In addition, as in FIG. 38, four nuts 31 are provided at equal intervals toward the inside of the plug 26 in the outer peripheral surface of the annular part 26A of the plug 26. The nuts 31 are formed by insert molding when molding the plug 26. Thick parts 33 for securing lengths of the nuts 31 are formed on an inner peripheral surface of the annular part 26A corresponding to positions of the nuts 31. The nuts 31 do not pass through the thick parts 33. In addition, through holes 35 are formed in the annular part 28A of the connector sheathing case corresponding to the positions of the four nuts 31 as in FIG. 39, and pin-shaped screws 37 are inserted from the through holes 35 and are fastened to the nuts 31 (refer to FIG. 38). Accordingly, the plug 26 connected to the connector sheathing case 28 is fixed via the four screws 37, and the four screws 37 prevent the plug 26 from falling out in a direction of the longitudinal axis 10*a* relatively to the connector sheathing case 28.

In addition, screw grooves 37A of the screws 37 each are formed to have a length by which the screws are fastened to the nuts 31, and portions 37B excluding the screw grooves 37A, that is, the portions 37B inserted into the through holes 35 each are formed in a straight rod shape without the screw grooves 37A. By configuring the screws 37 as described above, the screw grooves 37A of the screws 37 are fastened to the nuts 31 of the plug 26, and the straight rod-shaped portions 37B where the screw grooves 37A are not formed are inserted into the through holes 35 of the connector sheathing case 28. Accordingly, even in a case where the screw grooves 37A of the screws 37 are fastened to the nuts 31, the fastening of the screws 37 does not cause the bending of the connector sheathing case 28. Thus, water tightness between the plug 26 and the connector sheathing case 28 is maintained by the O-ring 34.

In addition, as illustrated in FIG. 40, two leading-out holes 38A and 38B that lead two fixing bases 36A and 36B (refer to FIG. 41), which are metal extension members, to the outside are provided adjacent to each other in a rear end of the connector sheathing case 28.

The fixing base 36A is a first fixing base for the universal cable 104 to be connected to the endoscope 100, and the fixing base 36B is a second fixing base for the video cable 14 to be connected to the flat connector 16, which is an electrical connector.

An elastic O-ring 40A (refer to FIG. 41) is fitted to an outer peripheral surface of the fixing base 36A, and the fixing base 36A is fitted to the leading-out hole 38A via the O-ring 40A. That is, the O-ring 40A is configured as a second sealing member that is provided on the fixing base 36A and seals the inside of the sheathing member 20 by being placed in a gap between the fixing base 36A and the leading-out hole 38A. In addition, the fixing base 36A is held by the connector sheathing case 28 via only the O-ring 40A without going through a member other than the O-ring 40A.

Similarly, an elastic O-ring 40B (refer to FIG. 41) is fitted to an outer peripheral surface of the fixing base 36B, and the fixing base 36B is fitted to the leading-out hole 38B via the O-ring 40B. That is, the O-ring 40B is configured as a third sealing member that is provided on the fixing base 36B and seals the inside of the sheathing member 20 by being placed in a gap between the fixing base 36B and the leading-out hole 38B. In addition, the fixing base 36B is held by the connector sheathing case 28 via only the O-ring 40B without going through a member other than the O-ring 40B.

A material for the fixing bases 36A and 36B is, for example, stainless steel, and a material for the O-rings 40A and 40B is, for example, fluoro rubber.

In the description above, in the connector device 10 of the embodiment, the metal light guide rod 12 is held by the resin plug 26 via the fluoro rubber O-ring 30, and the metal fixing bases 36A and 36B are held by the resin connector sheathing case 28 via the fluoro rubber O-rings 40A and 40B. Although the connector device 10 comprising the two fixing bases 36A and 36B are given as an example in the embodiment, the fixing base 36B is not an indispensable configuration member, and even a connector device comprising only the fixing base 36A can be applied.

Figure 41:
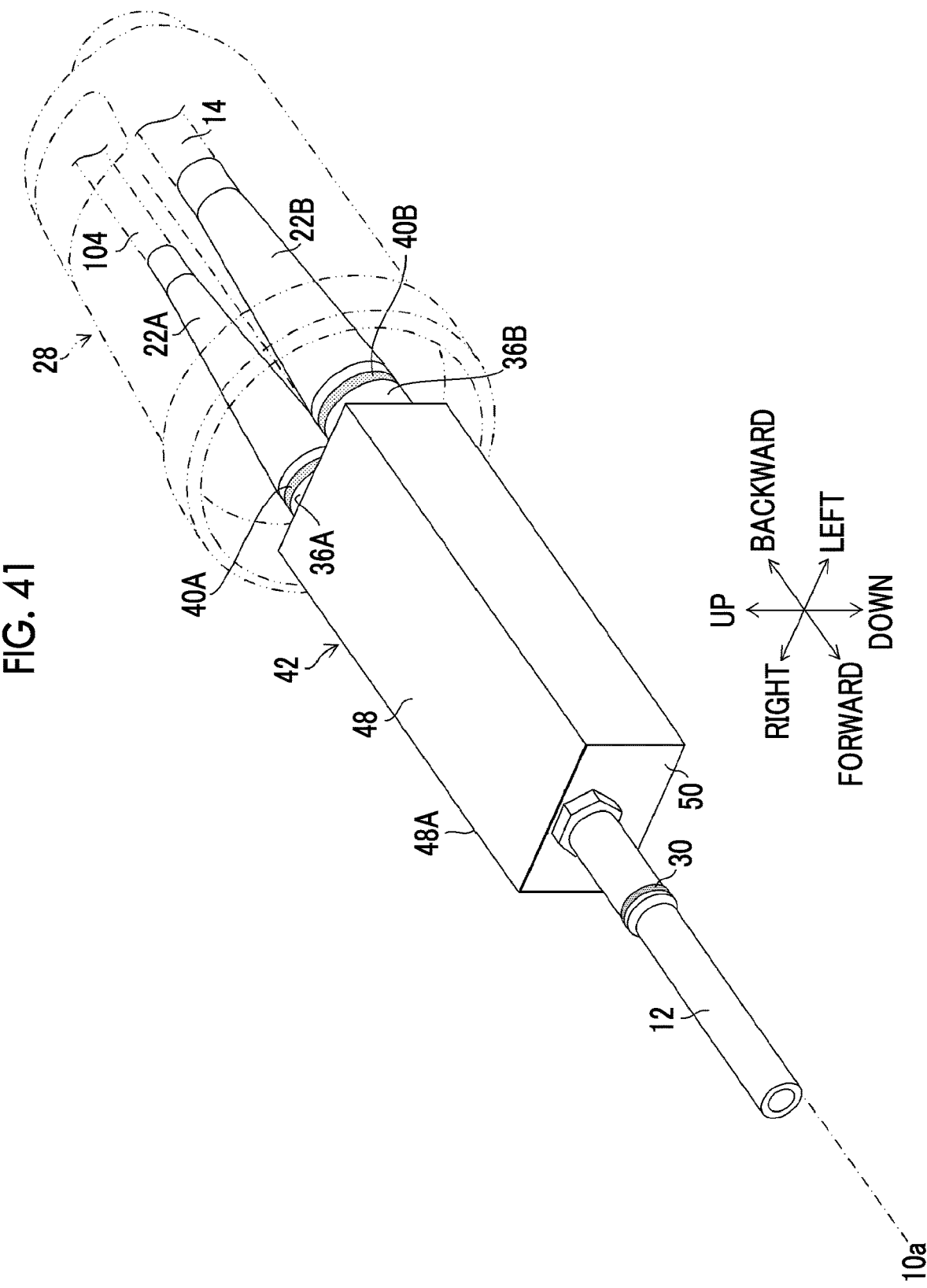
FIG. 41 is a perspective view illustrating a metal internal member to which the light guide rod and a fixing base are connected.

FIG. 41 is a perspective view illustrating a metal internal member 42 to which the light guide rod 12 and the fixing bases 36A and 36B are connected. In FIG. 41, the tubular cover 22A is connected to the fixing base 36A, and the distal end part of the universal cable 104 is inserted into the cover 22A and is fixed to the fixing base 36A. Similarly, the tubular cover 22B is connected to the fixing base 36B, and a proximal end part of the video cable 14 is inserted into the cover 22B and is fixed to the fixing base 36B.

Figure 42:
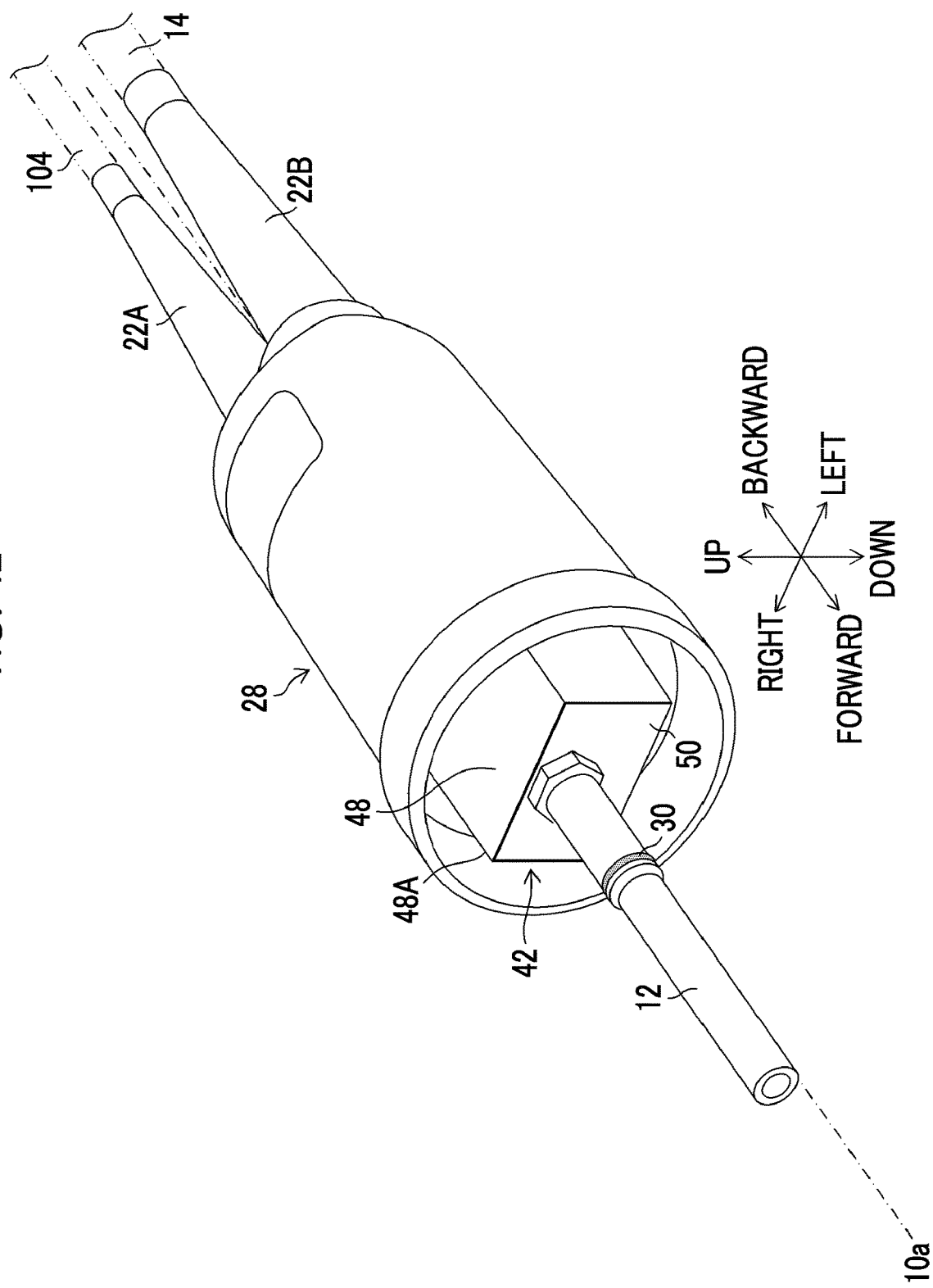
FIG. 42 is a perspective view of the connector sheathing case accommodating the internal member seen from an illumination light incidence end side.
Figure 44:
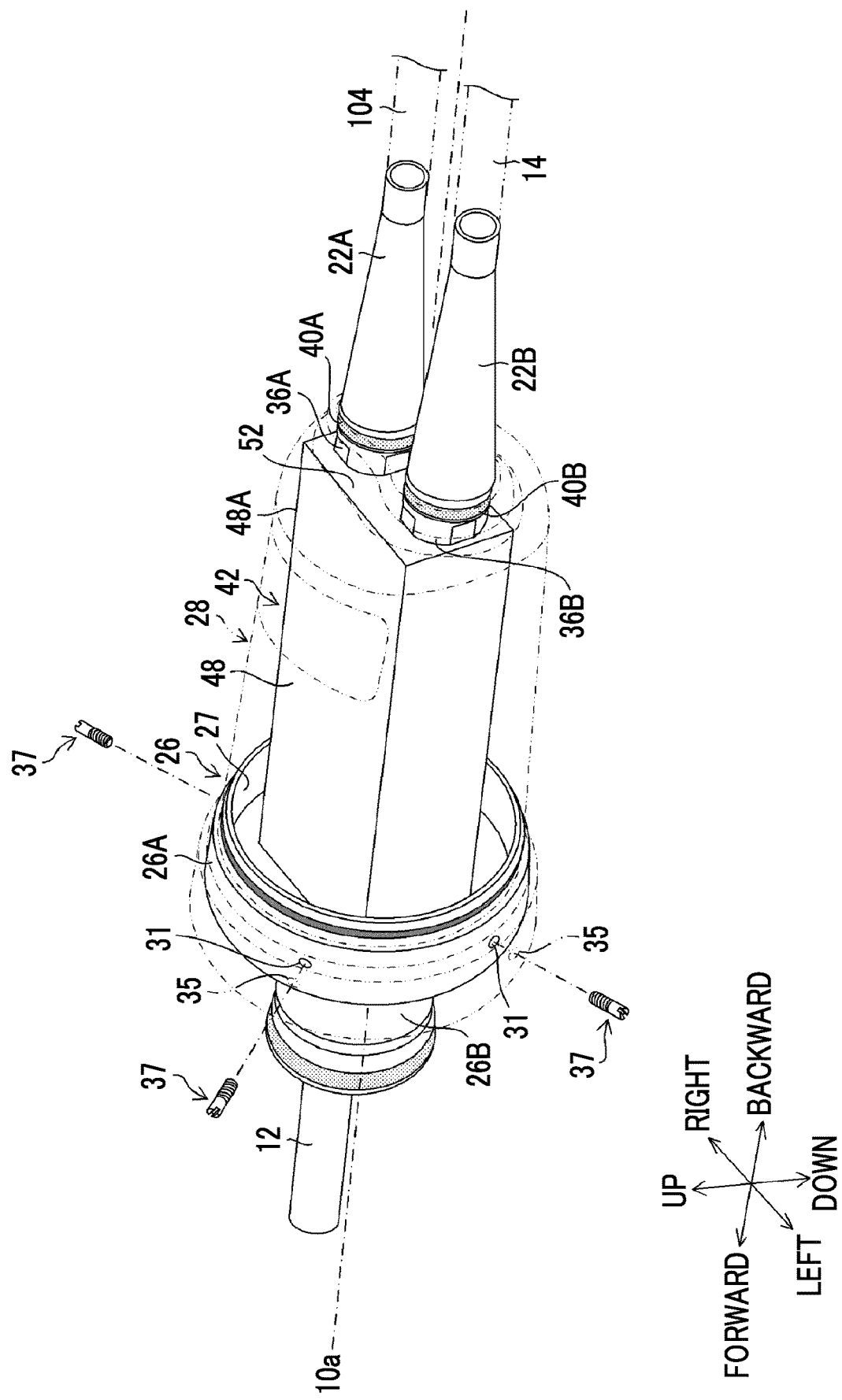
FIG. 44 is a perspective view of the connector device in which the plug is connected to the connector sheathing case shown with a two-dot chain line.

FIG. 42 is a perspective view of the connector sheathing case 28 accommodating the internal member 42 seen from an illumination light incidence end side. FIG. 43 is a perspective view illustrating a state where the internal member 42 excluding the light guide rod 12 is accommodated in the connector sheathing case 28. FIG. 44 is an external perspective view of the connector device 10 in which the plug 26 is connected to the connector sheathing case 28 shown with a two-dot chain line.

As illustrated in FIG. 44, the internal member 42 is accommodated inside the sheathing member 20 formed by the plug 26 and the connector sheathing case 28.

In addition, as illustrated in FIG. 41, the light guide rod 12 is connected to a fixing board 50 on a front end side, which is one end side of the internal member 42. As illustrated in FIG. 44, the fixing bases 36A and 36B are connected to a fixing board 52 on a rear end side, which is the other end side of the internal member. As described above, the light guide rod 12 is held by the plug 26 via only the O-ring 30, and the fixing bases 36A and 36B are held by the connector sheathing case 28 via only the O-rings 40A and 40B.

By such a holding structure, the internal member 42 is disposed to be spaced apart from an inner surface 27 of the plug 26 and an inner surface 29 of the connector sheathing case 28 as illustrated in FIGS. 43 and 44. In addition, in the connector device 10 of the embodiment, water tightness inside the sheathing member 20 is secured by the three O-rings 30, 40A, and 40B holding the internal member 42 inside the sheathing member 20.

As illustrated in FIG. 43, the internal member 42 is configured by a metal substrate 44, a metal shield case 46 in which the substrate 44 is disposed, and a metal case member 48 accommodating the shield case 46 therein. The case member 48 is configured in a rectangular parallelepiped shape. The case member 48 comprises the fixing boards 50 and 52.

In addition, as illustrated in FIGS. 41 to 44, the case member 48 is accommodated in the connector sheathing case 28 in a posture where a long side 48A of the case member 48 follows the longitudinal axis 10a, which corresponds to the axis of the cylindrical connector sheathing case 28. Although the internal member 42 having the shield case 46 is illustrated in an example of FIG. 43, even an internal member that does not comprise the shield case 46 and directly accommodates the substrate 44 inside the case member 48 can be applied.

Next, assembling procedures of the connector device 10 of the embodiment will be described.

First, a task of connecting the universal cable 104 and the fixing base 36A to each other and connecting the video cable 14 and the fixing base 36B to each other is performed. That is, in a case of connecting the universal cable 104 and the fixing base 36A to each other, the distal end part of the universal cable 104 is inserted into the connector sheathing case 28 from the leading-out hole 38A of the connector sheathing case 28, and the distal end part of the universal cable 104 is connected to the fixing base 36A (refer to FIG. 41). Similarly, also in a case of connecting the video cable 14 and the fixing base 36B to each other, the proximal end part of the video cable 14 is inserted into the connector sheathing case 28 from the leading-out hole 38B of the connector sheathing case 28, and the proximal end part of the video cable 14 is connected to the fixing base 36B (refer to FIG. 41).

Next, the connector sheathing case 28 is slid in a state where the universal cable 104 and the video cable 14 are pulled out, the fixing base 36A is fitted to the leading-out hole 38A via the O-ring 40A, and the fixing base 36B is fitted to the leading-out hole 38B via the O-ring 40B. Accordingly, as in FIG. 42, the internal member 42 is accommodated inside the connector sheathing case 28.

Next, as in FIG. 44, the plug 26 is connected to the connector sheathing case 28 from the front of the connector sheathing case 28. At this time, the light guide rod 12 is inserted into the leading-out hole 26C of the plug 26 of FIG. 37, and the positioning pin 32 is inserted into the through hole 26D of the plug 26. After then, the plug 26 is fixed to the connector sheathing case 28 by using the four screws 37 described above. The description above is the assembling procedures of the connector device 10.

Next, the working of the connector device 10 of the embodiment, which is configured as described above, will be described.

The connector device 10 of the embodiment comprises the metal internal member 42, the metal light guide rod 12 and the metal fixing bases 36A and 36B, which are connected to the internal member 42, and the resin sheathing member 20 that accommodates the internal member 42 and comprises the leading-out holes 26C, 38A, and 38B that lead the light guide rod 12 and the fixing bases 36A and 36B to the outside. In addition, the connector device 10 comprises the fluoro rubber O-rings 30, 40A, and 40B, which are provided on the light guide rod 12 and the fixing bases 36A and 36B, the O-rings 30, 40A, and 40B being respectively placed in the gaps between the light guide rod 12 and the fixing bases 36A and 36B and the leading-out holes 26C, 38A, and 38B and sealing the inside of the sheathing member 20.

Infiltration of moisture into the sheathing member 20, which occurs due to a difference in a thermal expansion factor between the resin sheathing member 20 and the metal light guide rod 12 and the metal fixing bases 36A and 36B, can be prevented in the connector device 10 having such a configuration. Hereinafter, specific description will be given.

In a case where sterilization processing is performed onto the connector device 10 of the embodiment together with the endoscope 100 by a high-pressure steam sterilizer, the gaps between the light guide rod 12 and the fixing bases 36A and 36B and the leading-out holes 26C, 38A, and 38B minutely widen due to a difference in a linear expansion coefficient between the resin sheathing member 20 and the metal light guide rod 12 and the metal fixing bases 36A and 36B. However, in an elastically deformed state at room temperature, the elastic fluoro rubber O-rings 30, 40A, and 40B are fitted to the gaps. For this reason, even in a case where the gaps are widened due to the difference in a linear expansion coefficiency described above, the O-rings 30, 40A, and 40B deform so as to follow the widening of the gaps. That is, by the O-rings 30, 40A, and 40B deforming so as to return to original shapes, sealed states of the gaps described above are maintained by the O-ring 30, 40A, and 40B.

Hence, even in a case where the gaps between the light guide rod 12 and the fixing bases 36A and 36B and the leading-out holes 26C, 38A, and 38B are widened when performing sterilization processing, water tightness inside the sheathing member 20 can be maintained by the O-rings 30, 40A, and 40B. Accordingly, the infiltration of moisture into the sheathing member 20, which occurs due to a difference in a thermal expansion factor between the resin sheathing member 20 and the metal light guide rod 12 and the metal fixing bases 36A and 36B, can be prevented in the connector device 10 of the embodiment.

In addition, in the connector device 10 of the embodiment, the internal member 42 is disposed to be spaced apart from the inner surface 27 of the plug 26 and the inner surface 29 of the connector sheathing case 28 by being held by the sheathing member 20 via only the O-rings 30, 40A, and 40B. With this configuration, the connector device 10 of the embodiment can obtain effects below.

In a case where the endoscope comprising the connector device is taken out from the high-pressure steam sterilizer, a temperature of the connector device heated by the high-pressure steam sterilizer gradually declines due to outside air. Herein, for example, in a case where a configuration, in which the shield case of the internal member is in contact with or has approached the sheathing member, in particular, the inner surface of the connector sheathing case, is adopted, a temperature difference between the connector sheathing case and the shield case is less likely to occur in the process of temperature decline after sterilization processing. Thus, there is a problem in which moisture in the air inside the connector sheathing case attaches to the inner wall of the shield case and the substrate, condensation occurs, and the substrate is adversely affected. That is, condensation occurs also on the inner wall of the connector sheathing case. Simultaneously or without a time gap with this condensation, condensation occurs on the inner wall of the shield case and the substrate.

On the contrary, in the connector device 10 of the embodiment, an outer surface of the internal member 42 is disposed to be spaced apart from the inner surface 27 of the plug 26 and the inner surface 29 of the connector sheathing case 28 by the sheathing member 20 holding the internal member 42 via only the O-rings 30, 40A, and 40B. In addition, in the connector device 10 of the embodiment, a sufficient space can be secured between an inner surface of the sheathing member 20 and an outer surface of the case member 48 by disposing the rectangular parallelepiped case member 48 inside the cylindrical connector sheathing case 28. Hence, since a temperature of the sheathing member 20 starts to decline first in the process of temperature decline described above, condensation occurs on the inner surface of the sheathing member 20 in the connector device 10 of the embodiment. After then, condensation occurs on the outer surface of the case member 48 after a predetermined time elapses. Accordingly, condensation onto the substrate 44 disposed inside the case member 48 can be prevented in the connector device 10 of the embodiment.

In addition, since the internal member 42 is not fixed to the connector sheathing case 28, internal stress caused by a temperature difference between the connector sheathing case 28 and the internal member 42 can be reduced in the connector device 10 of the embodiment. Accordingly, heat cycle resistance caused by steam sterilization improves.

In addition, since a sufficient space is secured between the inner surface of the sheathing member 20 and the outer surface of the internal member 42 in the connector device 10 of the embodiment, a time constant (relaxation time) at which heat from the high-pressure steam sterilizer is transmitted to electrical parts of the substrate 44 increases. Accordingly, heat stress to an electrical equipment can be reduced.

In the connector device 10 of the embodiment, the internal member 42 is provided with a damper part that absorbs a thermal expansion difference between the connector sheathing case 28 and the case member 48. Hereinafter, a configuration and working of the damper part will be described based on the drawings.

Figure 45:
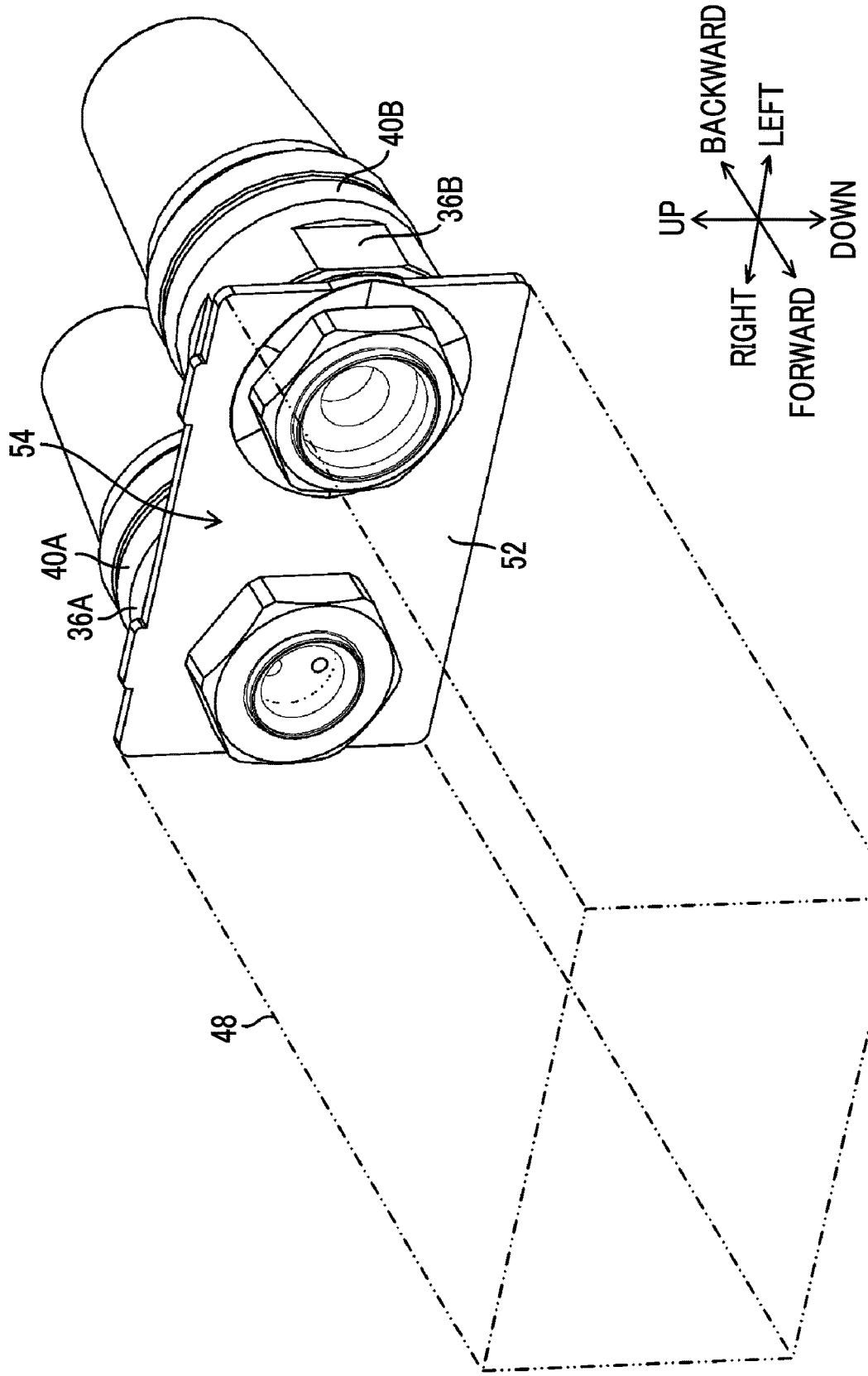
FIG. 45 is a perspective view illustrating a structure of a fixing part of the fixing base with respect to a fixing board of a case member.
Figure 46:
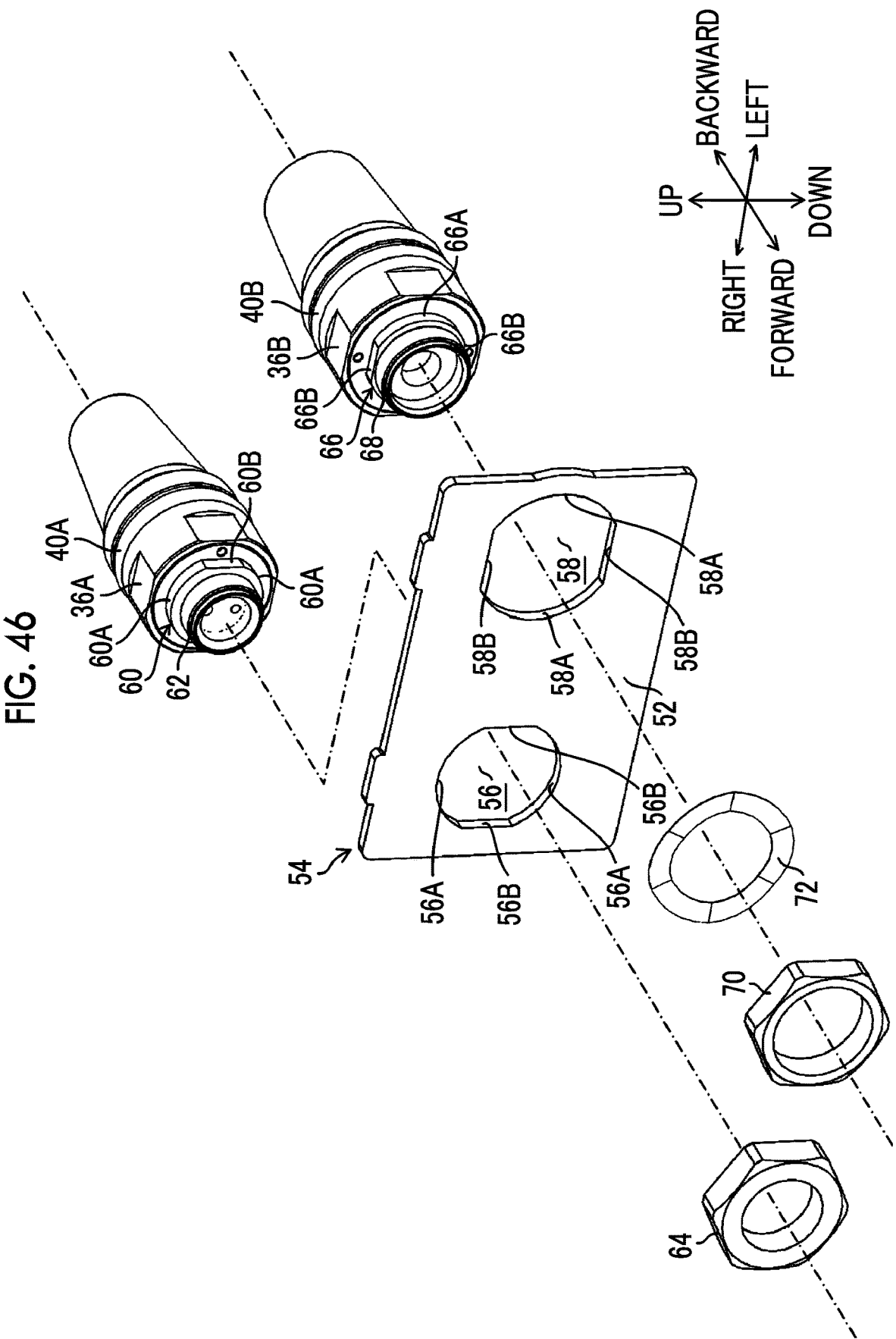
FIG. 46 is an assembly perspective view of the fixing part.

FIG. 45 is a perspective view illustrating a structure of a fixing part 54 of the fixing base 36A and 36B with respect to the fixing board 52 of the case member 48. FIG. 46 is an assembly perspective view of the fixing part 54.

As illustrated in FIGS. 45 and 46, the case member 48 comprises the fixing board 52 that fixes the fixing bases 36A and 36B. The fixing board 52 comprises a through hole 56 that is a first attaching hole to which the fixing base 36A is attached and a through hole 58 that is a second attaching hole to which the fixing base 36B is attached. In the embodiment, the fixing base 36B corresponds to one fixing base according to the embodiment of the present invention, and the through hole 58 corresponds to one attaching hole according to the embodiment of the present invention.

Amount part 60 fitted to the through hole 56 and a male screw part 62 protruding forward from the mount part 60 are formed on a front end surface of the fixing base 36A.

Figure 47:
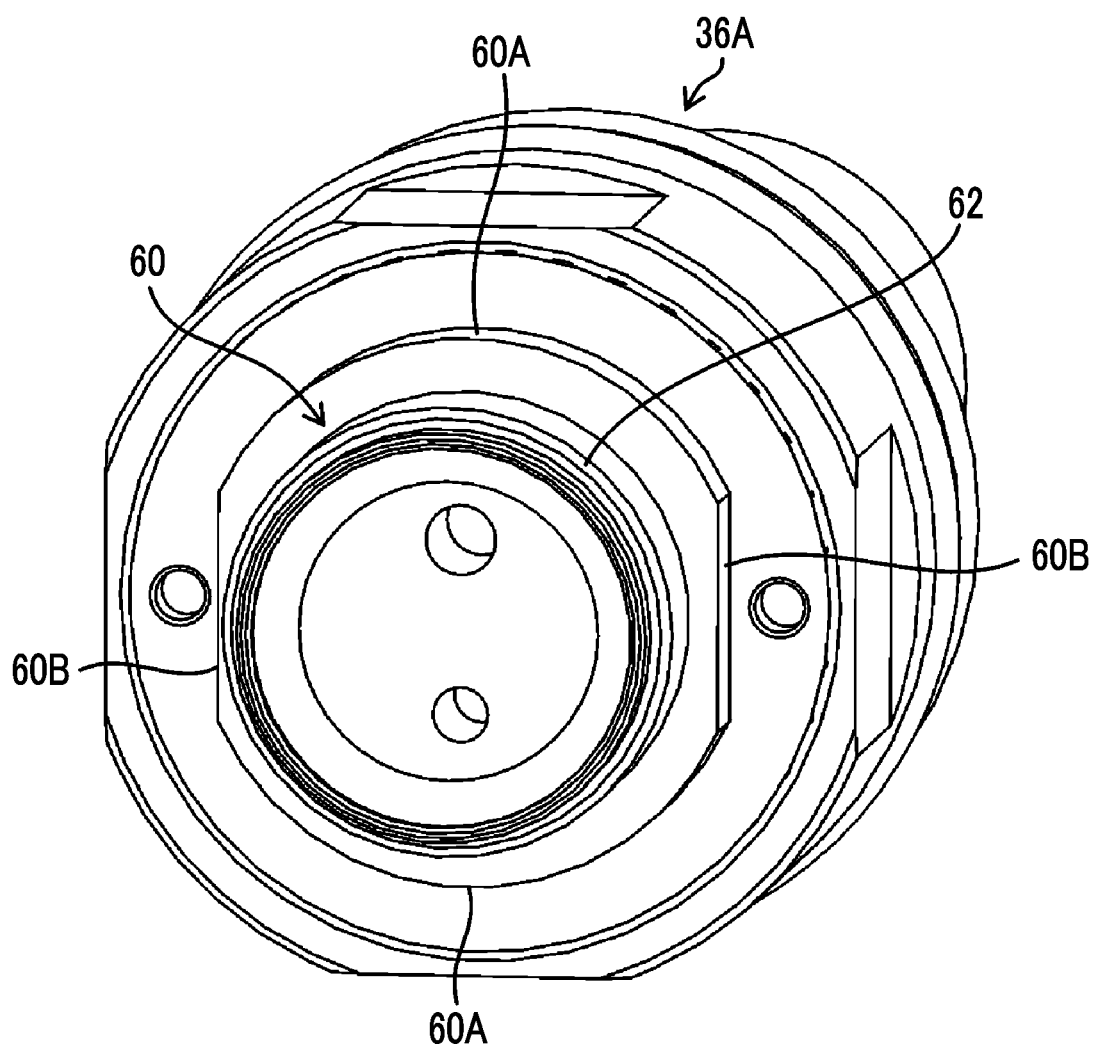
FIG. 47 is a view of a front end surface of a first fixing base seen from the front toward the rear of the fixing base.

FIG. 47 is a front view of the front end surface of the fixing base 36A. An outer surface of the mount part 60 of the fixing base 36A has two arc portions 60A and 60A facing each other and two straight line portions 60B and 60B that are provided to face each other so as to connect the arc portions 60A and 60A. Referring back to FIG. 46, an inner surface of the through hole 56 of the fixing board 52 has two arc portions 56A and 56A that receive the arc portions 60A and 60A and two straight line portions 56B and 56B that receive the straight line portions 60B and 60B. In the fixing part of the fixing base 36A with respect to the fixing board 52, a length between the straight line portions 56B and 56B and a length between the straight line portions 60B and 60B are formed to be the same. By fitting the straight line portions 60B and 60B to the straight line portions 56B and 56B, the fixing base 36A is attached to the fixing board 52 without an upward, downward, right, or left positional shift. As illustrated in FIG. 46, by fastening a nut 64 to the male screw part 62 protruding forward from the through hole 56, the fixing base 36A is fixed to the fixing board 52.

Next, the fixing base 36B will be described. A mount part 66 fitted to the through hole 58 and a male screw part 68 protruding forward from the mount part 66 are formed on a front end surface of the fixing base 36B.

Figure 48:
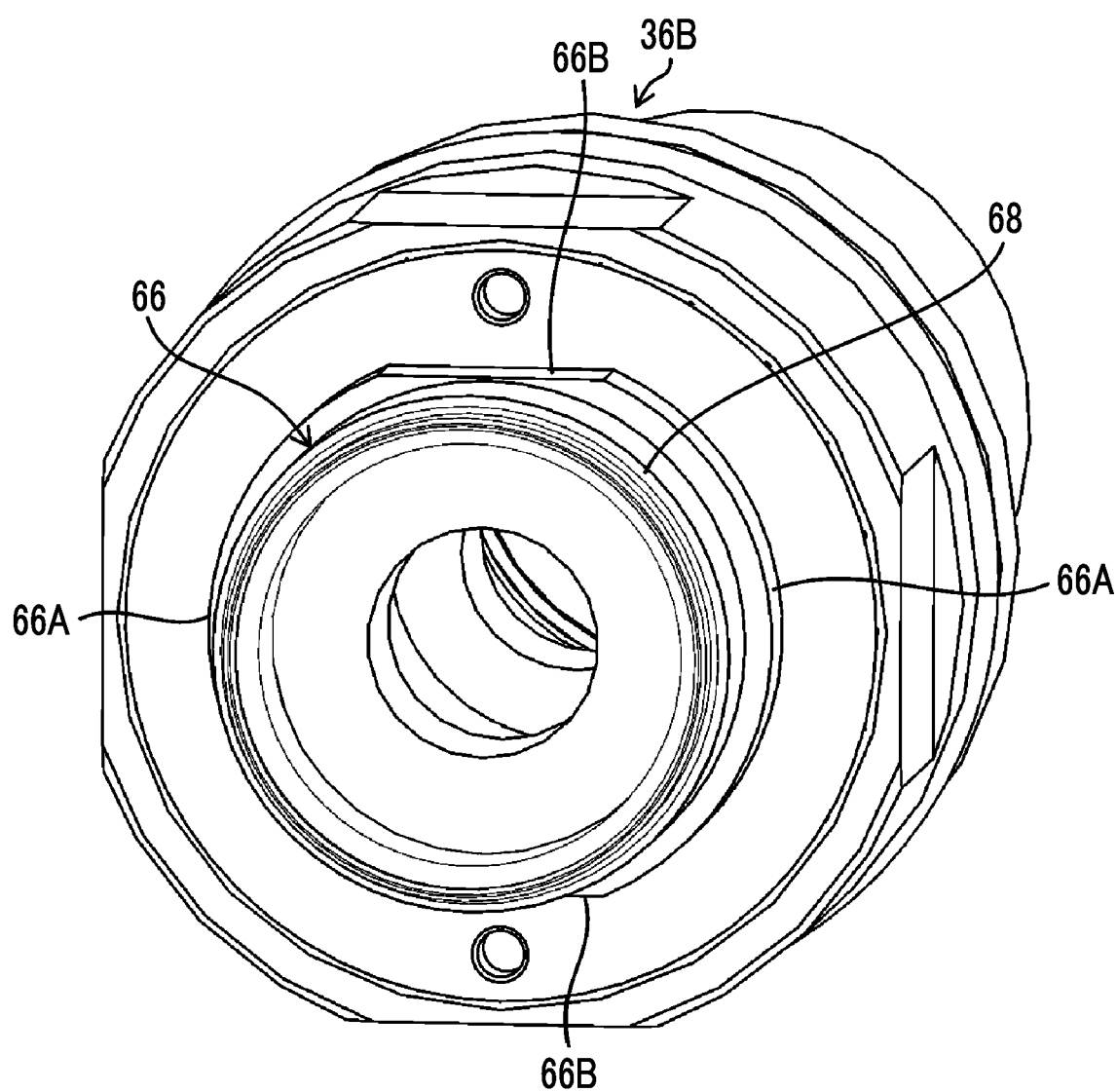
FIG. 48 is a view of a front end surface of a second fixing base seen from the front toward the rear of the fixing base.

FIG. 48 is a front view of the front end surface of the fixing base 36B. An outer surface of the mount part 66 of the fixing base 36B has two arc portions 66A and 66A facing each other and two straight line portions 66B and 66B that are provided to face each other so as to connect the arc portions 66A and 66A. Referring back to FIG. 46, an inner surface of the through hole 58 of the fixing board 52 comprises two arc portions 58A and 58A that receive the arc portions 66A and 66A and two straight line portions 58B and 58B that receive the straight line portions 66B and 66B.

Figure 49:
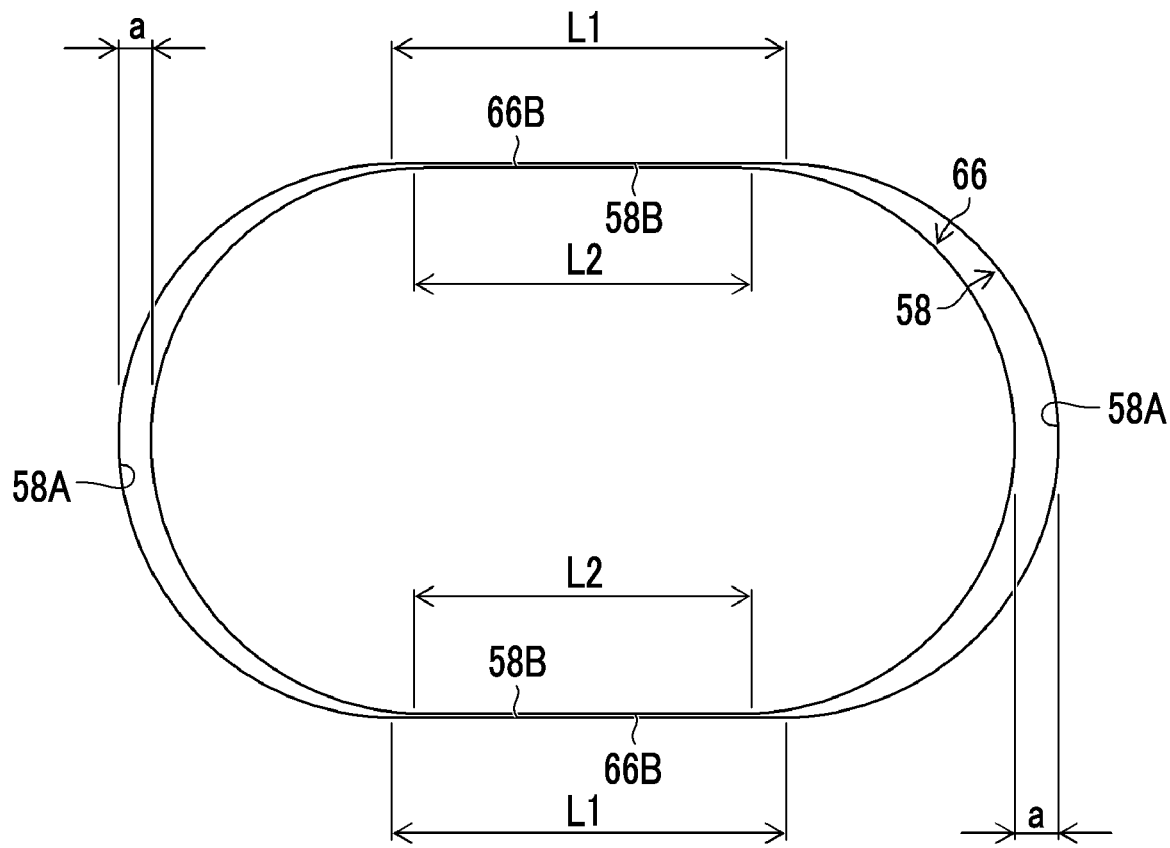
FIG. 49 is an explanatory view illustrating a length relationship between a straight line portion of a through hole and a straight line portion of the fixing base.

FIG. 49 is an explanatory view illustrating a length relationship between the straight line portions 58B and 58B of the through hole 58 and the straight line portions 66B and 66B of the fixing base 36B. As illustrated in FIG. 49, the straight line portions 58B and 58B each having the length L1 are formed to be longer than the straight line portions 66B and 66B each having the length L2. Accordingly, the fixing base 36B is attached to the through hole 58 so as to be movable in the leftward-rightward direction along the straight line portions 66B and 66B by an illustrated dimension a. As illustrated in FIG. 46, by fastening a nut 70 to the male screw part 68 protruding forward from the through hole 58 via a wave washer 72, the fixing base 36B is fixed to the fixing board 52.

In the fixing part 54 configured as described above, the fixing part that fixes the fixing base 36B to the fixing board 52 functions as the damper part described above. That is, in a case where a thermal expansion difference between the connector sheathing case 28 and the case member 48 occurs, the fixing base 36B held by the connector sheathing case 28 moves in the leftward-rightward direction along the straight line portions 66B and 66B with respect to the through hole 58 of the fixing board 52. Accordingly, the thermal expansion difference between the connector sheathing case 28 and the case member 48 can be absorbed. Although the male screw part 68 of the fixing base 36B is fixed to the fixing board 52 by the nut 70, the fixing base 36B can move in the leftward-rightward direction by the thermal expansion difference without the movement of the fixing base 36B with respect to the fixing board 52 in the leftward-rightward direction being restricted since the wave washer 72 is placed between the fixing board 52 and the nut 70.

As described above, even in a case where a thermal expansion difference between the connector sheathing case 28 and the case member 48 occurs, the thermal expansion difference can be absorbed since the fixing part of the fixing base 36B functions as the damper part in the connector device 10 of the embodiment. Accordingly, internal stress caused by a temperature difference between the connector sheathing case 28 and the internal member 42 can be further reduced.

Although the fixing part of the fixing base 36A may be provided with the damper part described above, the vulnerable glass fiber light guide 118 is inserted into the fixing base 36A. For this reason, the fixing base 36A is fixed to the internal member 42 without movement. On the contrary, since a bendable signal line is inserted and disposed in the fixing base 36B, the signal line is not affected even in a case where the fixing base 36B moves with respect to the internal member 42. From this point of view, the fixing base 36B is provided with the damper part.

In addition, the connector device 10 of the embodiment can also be applied to a flexible endoscope without being limited to a hard endoscope.

In general laparoscopic surgery, first, in a state where an inner needle is inserted in a trocar, a distal end of the trocar is inserted into a patient's body wall, and the inner needle is removed from the trocar. Next, a pneumoperitoneum gas such as a carbon dioxide gas is injected into a body cavity via the trocar to fill the body cavity with the pneumoperitoneum gas, thereby securing a space for surgery. After then, an endoscope (rigid endoscope) insertion part is inserted from an introduction port on a proximal end of the trocar, a distal end of the endoscope insertion part is introduced into an abdominal cavity, and the laparoscopic surgery starts. The introduction port of the trocar comprises a valve body. By the valve body being closely attached to an outer peripheral surface of the endoscope insertion part, the leakage of the pneumoperitoneum gas from the abdominal cavity via the trocar is prevented, and a state of pneumoperitoneum is maintained.

Herein, the endoscope insertion part 102 used in the overtube 300 of FIG. 1 is configured such that an outer diameter thereof is smaller than an outer diameter of the endoscope insertion part generally used in laparoscopic surgery. For that reason, in a case where the endoscope insertion part 102 is inserted into a trocar generally used in laparoscopic surgery, a gap is generated between the outer peripheral surface of the endoscope insertion part 102 and the valve body, or sealing becomes insufficient. Thus, a defect in which the pneumoperitoneum gas leaks from the abdominal cavity via the trocar occurs.

Thus, in order to prevent such a defect, by sheathing a tubular sheath to the endoscope insertion part 102, an outer diameter of the endoscope insertion part 102 is increased to match an outer diameter of the sheath.

Figure 50:
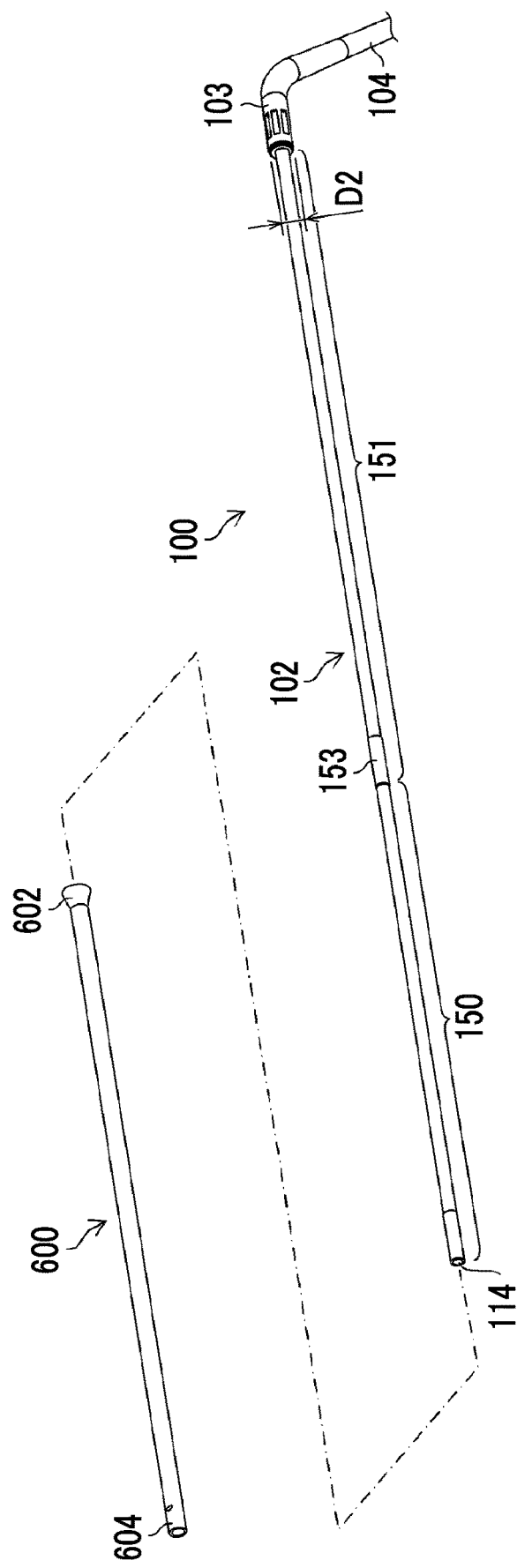
FIG. 50 is an explanatory view of a sheath sheathed to the endoscope insertion part.
Figure 51:
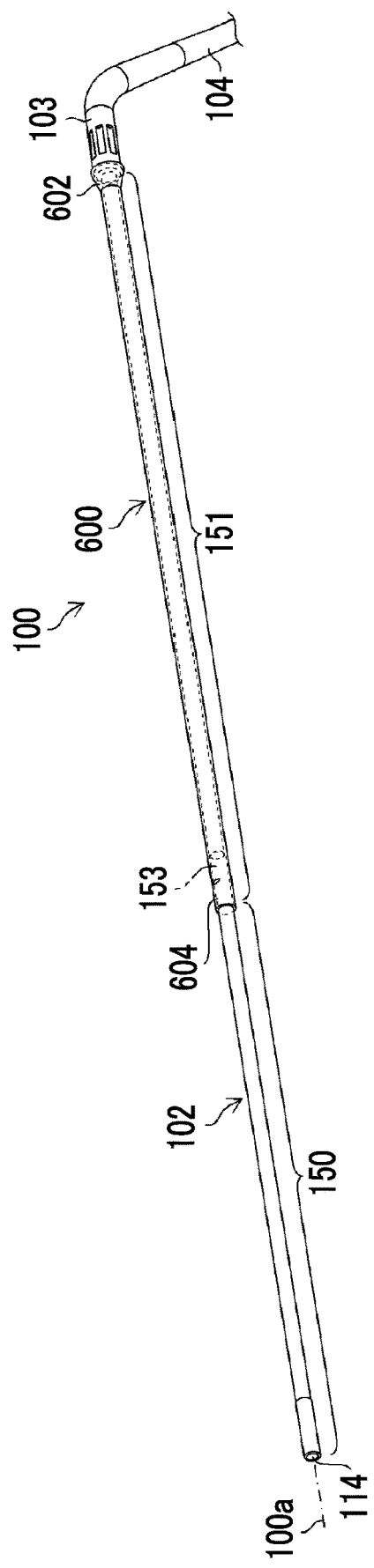
FIG. 51 is an explanatory view of the endoscope to which the sheath is sheathed.

FIG. 50 illustrates a sheath 600 sheathed to the endoscope insertion part 102. In addition, FIG. 51 illustrates the endoscope 100 to which the sheath 600 is sheathed.

The sheath 600 is configured to have a length that allows the sheath to cover from the proximal end part of the endoscope insertion part 102 to the held part 153. The length of the sheath 600 may be a length corresponding to a full length of the endoscope insertion part 102 (refer to FIG. 54). In addition, an outer diameter of the sheath 600 is configured to be 4.5 mm to 5.5 mm, an inner diameter of the sheath 600 is configured to be 3.7 mm to 4.0 mm so as to correspond to the outer diameter of the endoscope insertion part 102 (the outer diameter R1 of the first insertion part 150: 3.7 mm and the outer diameter R2 of the second insertion part 151: 3.8 mm). As a material for the sheath 600, an electrically insulating and extrudable material is preferable. A polyether block amide (nylon-based thermoplastic elastomer) (thermoplastic polyamid elastomer (TPAE)) can be given as an example. In addition, as another material for the sheath 600, a fluorine resin, such as a tetrafluoroethylene/perfluoalkylvinylether copolymer (PFA) and a tetrafluoroethylene/hexafluoropropylene copolymer (4.6 fluorination) (fluorinated ethylene propylene (FEP) copolymer) can be given as an example. In addition, polycarbonate (PC) or an acrylonitrile butadiene styrene resin (acrylonitrile butadiene styrene (ABS) copolymer) can be given as an example.

Figure 52:
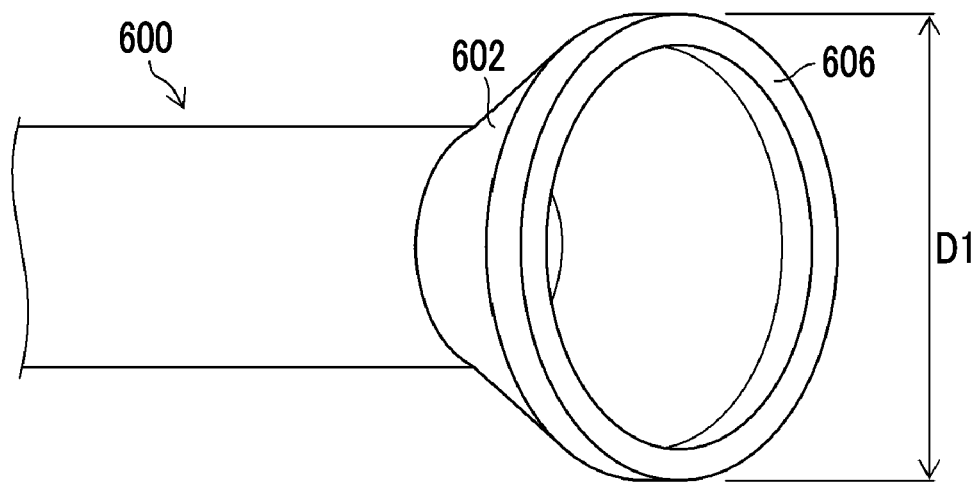
FIG. 52 is an enlarged perspective view illustrating a proximal end part of the sheath.

The sheath 600 has a proximal end part 602 and a distal end part 604. FIG. 52 is an enlarged perspective view illustrating important parts of the proximal end part 602 of the sheath 600. The proximal end part 602 comprises a tapered portion 606 having a large diameter, and has a structure that allows inserting of the endoscope insertion part 102 from the proximal end part 602 easier. In addition, the largest outer diameter D1 of the tapered portion 606 is configured to be substantially the same as the outer diameter D2 of a distal end surface of the grip part 103 of the endoscope 100 of FIG. 50. Accordingly, when the tapered portion 606 has abutted against the distal end surface of the grip part 103, the grip part 103 and the tapered portion 606 are connected to each other without a step.

Figure 53:
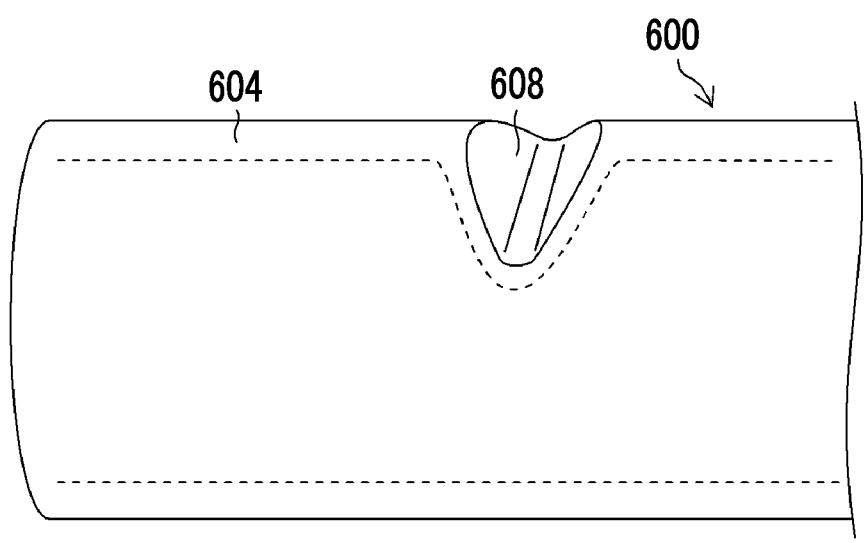
FIG. 53 is an enlarged perspective view illustrating a distal end part of the sheath.

FIG. 53 is an enlarged perspective view illustrating important parts of the distal end part 604 of the sheath 600. A recessed neck part 608 is formed in the distal end part 604. A configuration where resistance is applied to insertion and extraction of the endoscope insertion part 102 by an outer diameter and an inner diameter of the distal end part 604 being reduced at a position where the neck part 608 is formed and the outer peripheral surface of the endoscope insertion part 102 inserted into the sheath 600 coming into contact with the neck part 608 is adopted.

Figure 54:
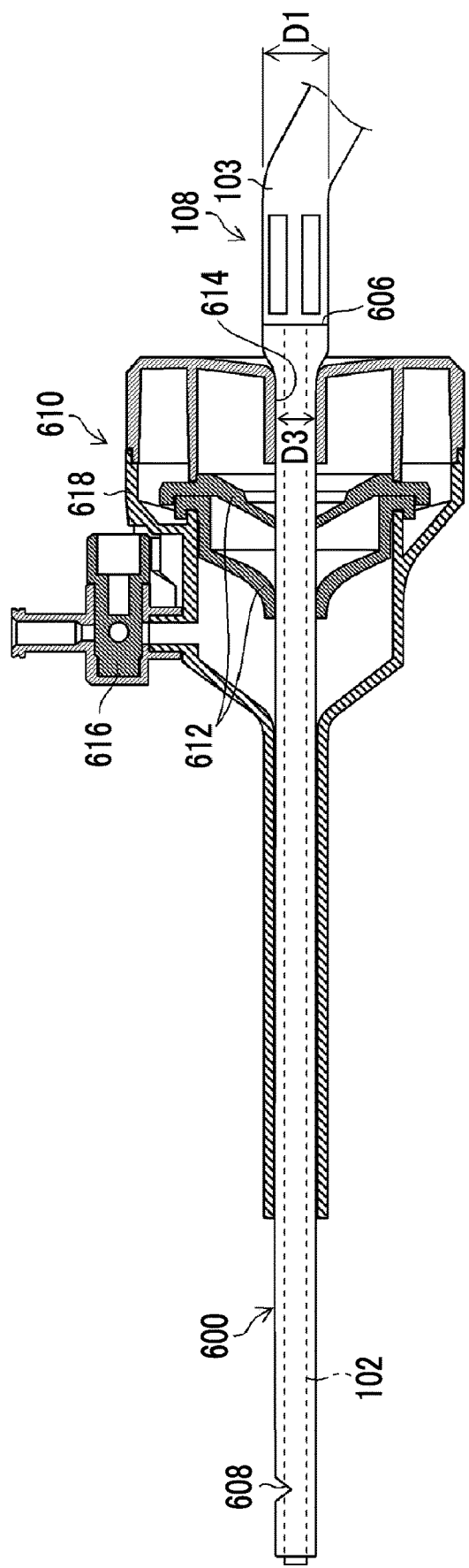
FIG. 54 is a cross-sectional view of important parts of a trocar in which the endoscope insertion part, to which the sheath is sheathed, is inserted.

FIG. 54 is a cross-sectional view of a trocar 610 generally used in laparoscopic surgery, that is, the trocar 610 into which the endoscope insertion part 102, to which the sheath 600 is sheathed, is inserted. In FIG. 54, the outer diameter of the endoscope insertion part 102 can be increased to match the outer diameter of the sheath 600 by sheathing the sheath 600 to the endoscope insertion part 102. Accordingly, in a case where the endoscope insertion part 102 to which the sheath 600 is sheathed is inserted into the trocar 610, a sealing effect can be secured since gaps are not generated between valve bodies 612 and 612 of the trocar 610 and an outer peripheral surface of the sheath 600. Accordingly, a problem of leakage of a pneumoperitoneum gas from an abdominal cavity via the trocar 610 can be solved.

Hence, by using such a sheath 600, the endoscope 100 can be applied to the trocar 610 generally used in laparoscopic surgery. In addition, the largest outer diameter D1 of the tapered portion 606 is formed to be larger than an inner diameter D3 of an introduction port 614 on a proximal end of the trocar 610. Due to such a configuration, the sheath 600 can prevent itself from entering the trocar 610 when the endoscope insertion part 102 has fallen out from the sheath 600. In FIG. 54, the sheath 600 having a length corresponding to the full length of the endoscope insertion part 102 is applied. In addition, the trocar 610 of FIG. 54 comprises a valve 616. The valve 616 is provided in a base part 618 in which the introduction port 614 is formed. The valve 616 is configured to be opened such that a pneumoperitoneum gas is supplied to the trocar 610.

Explanation of References
  1: surgical system
  10: connector device
  10a: longitudinal axis
  12: light guide rod
  14: video cable
  16: flat connector
  20: sheathing member
  22A: cover
  22B: cover
  26: plug
  26A: annular part
  26B: tubular shape part
  26C: leading-out hole
  26D: through hole
  27: inner surface
  28: connector sheathing case
  28A: annular part
  29: inner surface
  30: O-ring
  31: nut
  33: thick part
  34: O-ring
  35: through hole
  36A: fixing base
  36B: fixing base
  37: screw
  37A: screw groove
  37B: portion
  38A: leading-out hole
  38B: leading-out hole
  40A: O-ring
  40B: O-ring
  42: internal member
  44: substrate
  46: shield case
  48: case member
  48A: long side
  50: fixing board
  52: fixing board
  54: fixing part
  56: through hole
  56A: arc portion
  56B: straight line portion
  58: through hole
  58A: arc portion
  58B: straight line portion
  60: mount part
  60A: arc portion
  60B: straight line portion
  62: male screw part
  64: nut
  66: mount part
  66A: arc portion
  66B: straight line portion
  68: male screw part
  70: nut
  72: wave washer
  100: endoscope
  102: endoscope insertion part
  102A: distal end surface
  103: grip part
  103A: body
  103B: cover
  104: universal cable
  105A: annular part
  105B: tubular shape part
  107: groove
  108: processor device
  110: light source device
  112: monitor
  114: observation part
  116: observation window
  118 light guide
  118A: emission end
  120: image pick-up lens group
  122: prism
  124: solid image pickup element
  126: signal line
  126A: output signal line
  128: base substrate
  129: polyimide adhesive tape
  130: circuit substrate
  132: flexible cable
  134: lens barrel 134A: body part
134B: holding part
134C: holding part
135: silicon tube
136: bracket
138: terminal part
138A: fitted part
140: spiral tube
142: net
144: skin
146: tube
148: net
149: tube
150: first insertion part
150a: tubular body
150b: longitudinal axis
151: second insertion part
151a: tubular body
153: held part
155: tubular body
156: pipe-like member
200: treatment tool
202: treatment tool insertion part
204: operating part
206: treatment part
250: airtight casing
250b: longitudinal axis
250A: distal end
250B: proximal end
250C: fitting part
252: first tubular body
254: second tubular body
300: overtube
300a: longitudinal axis
302: proximal end surface
304: distal end surface
306: endoscope insertion passage
306a: endoscope insertion axis
308: treatment tool insertion passage
308a: treatment tool insertion axis
310: first proximal end opening
312: first distal end opening
314: second proximal end opening
316: second distal end opening
320: overtube long tubular part
322: long tubular body
324: partition wall member
326: endoscope guide groove
328: treatment tool guide groove
340: proximal end cap
360: distal end cap
400: slider
402: coupling ring
404: ring part
404A: first engaging part
406: arm part
408: rear restriction end
408A: opening
410: front restriction end
410A: opening
412: engagement hole
420: endoscope coupling part
422: treatment tool coupling part
430: endoscope fixing tool
432: holding frame
434: endoscope elastic holding body
434a: endoscope holding surface
436: protrusion
422: treatment tool coupling part
450: treatment tool fixing tool
452: frame
454: treatment tool elastic holding body
454a: treatment tool holding surface
500: outer sheath
500a: distal end opening
500b: proximal end opening
504: vertical groove
520: horizontal groove
600: sheath
602: proximal end part
604: distal end part
605: distal end surface
606: tapered portion
608: neck part
610: trocar
612: valve body
614: introduction port
616: valve
618: base part

What is claimed is:

1. An endoscope connector device comprising:
a metal internal member;
a metal extension member that is connected to the internal member;
a resin sheathing member that accommodates the internal member and comprises a leading-out hole which leads the extension member to an outside; and
an elastic sealing member that is directly fitted to an outer peripheral surface of the extension member, and sealed in a gap between the extension member and the leading-out hole to seal the inside of the sheathing member,
wherein the extension member is held by the resin sheathing member via only the elastic sealing member without going through a member other than the elastic sealing member,
wherein the internal member has a case member accommodating a substrate or a shield case in which the substrate is disposed,
wherein the sheathing member comprises a plug that holds a light guide rod, and a connector sheathing case that is connected to the plug and accommodates the case member,
wherein the connector sheathing case is formed in a cylindrical shape,
the case member is formed in a rectangular parallelepiped shape, and
the case member is accommodated in the connector sheathing case in a posture where a long side of the case member follows an axis of the cylindrical connector sheathing case.

2. The endoscope connector device according to claim 1, wherein the internal member is disposed to be spaced apart from an inner surface of the sheathing member by being held by the sheathing member via only the sealing member.

3. The endoscope connector device according to claim 1, wherein the sealing member is an O-ring fitted to the outer peripheral surface of the extension member.

4. The endoscope connector device according to claim 1, wherein the endoscope connector device further comprises the light guide rod and a first fixing base for a universal cable connected to an endoscope as the extension member.

5. The endoscope connector device according to claim 4, further comprising:
- a second fixing base for a video cable connected to an electrical connector as the extension member.

6. The endoscope connector device according to claim 5, wherein the light guide rod is connected to one end of the case member, and
the first fixing base and the second fixing base are connected to the other end of the case member.

7. The endoscope connector device according to claim 5, wherein the sheathing member comprises
- the sealing member, comprising
  - a first sealing member that causes the plug to hold the light guide rod,
  - a second sealing member that causes the connector sheathing case to hold the first fixing base, and
  - a third sealing member that causes the connector sheathing case to hold the second fixing base.

8. The endoscope connector device according to claim 5, wherein the case member comprises a fixing board that fixes the first fixing base and the second fixing base,
the fixing board comprises a first attaching hole to which the first fixing base is attached and a second attaching hole to which the second fixing base is attached, and
in one fixing base of the first fixing base or the second fixing base and one attaching hole of the first attaching hole or the second attaching hole, to which the one fixing base is attached,
- an outer surface of the one fixing base has two straight line portions provided to face each other,
- an inner surface of the one attaching hole has two straight line portions provided to face each other so as to receive the two straight line portions of the one fixing base, and
- the straight line portions of the one attaching hole are longer than the straight line portions of the one fixing base.

9. The endoscope connector device according to claim 8, wherein the outer surface of the one fixing base has two arc portions provided to face each other so as to connect the two straight line portions of the one fixing base, and
the inner surface of the one attaching hole has two arc portions provided to face each other so as to receive the two arc portions of the one fixing base.

10. The endoscope connector device according to claim 8, wherein the one fixing base is the second fixing base.

\* \* \* \* \*